US006967102B1

(12) United States Patent (10) Patent No.: US 6,967,102 B1
Anderson (45) Date of Patent: Nov. 22, 2005

(54) NITRIC OXIDE MANIPULATION OF MUSCLE SATELLITE CELL ACTIVATION

(75) Inventor: Judy E. Anderson, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 09/936,609

(22) PCT Filed: Mar. 10, 2000

(86) PCT No.: PCT/CA00/00255

§ 371 (c)(1),
(2), (4) Date: Jan. 7, 2002

(87) PCT Pub. No.: WO00/53191

PCT Pub. Date: Sep. 14, 2000

Related U.S. Application Data

(60) Provisional application No. 60/123,895, filed on Mar. 11, 1999.

(51) Int. Cl.$^7$ ............................................. G01N 33/48
(52) U.S. Cl. ........................................ 436/63; 514/753
(58) Field of Search ........................... 436/63; 514/753

(56) References Cited

U.S. PATENT DOCUMENTS 5,583,101 A 12/1996 Stamler et al.
6,444,642 B1 * 9/2002 Sklar et al. .................... 514/8

FOREIGN PATENT DOCUMENTS

WO 9733173 9/1997

OTHER PUBLICATIONS

Ulibarri et al. Medicine and Science in Sports and Exercise, vol. 29, No. 5 suppl. (1997), p. S228, XP000961780, 44$^{th}$ Annual Meeting of the American College of Sports Medicine; Denver, Colorado, USA; May 28-31, 1997, abstract.
Database Biosis [Online] Biosciences Information Service, Philadelphia, PA, US1993, Baek Mi-Yeong et al., Database accession No. PREV199396097003, XP002154299, abstract.
Bredt, David S., Proceedings of the National Academy of Sciences of the United States, vol. 95, No. 25, Dec. 1998, pp. 14592-14593, XP000960480.
Sarkar, Rajabrata et al., Surgery (St. Louis), vol. 118, No. 2 (1995) pp. 274-279, XP 000961764.
Database WPI, Section Ch, Week 199831 Derwent Publications Ltd., London, GB; AN 1998-350696, XP002154301.
Database Biosis [Online] Biosciences Information Service, Philadelphia, PA, UA, Nov. 1997, Lamosova D et al., Database accession No. PREV199800098087, XP002154300, abstract.

Azzena et al., Neuroscience Letters, Limerick, IE, vol. 261, No. 1/02 (1999) pp. 9-12, XP000879028.
Lee Kun Ho et al., Journal of Biological Chemistry, vol. 269, No. 20 (1994) pp. 14371-14374, XP002154298.
Yan, Zhong-Qun et al., Circulation Research, vol. 82, No. 1, pp. 21-29, XP000961767.
Haycock et al., Neuroreport, GB, Rapid Communications of Oxford, Oxford, vol. 8, No. 1 (1996) pp. 357-361, XP000879014.
Chao, Daniel S. et al., Journal of Experimental Medicine, vol. 184, No. 2 (1996) pp. 609-618, XP000961763.
Azzena, Gian Battista et al., Neuroscience Letters, vol. 261, No. 1-2 Feb. 12, 1999, pp. 9-12, XP000961771.
Sohn, Yoon K. et al., Journal of the Neurological Sciences, vol. 162, No. 2, Jan. 15, 1999, pp. 133-151, XP000961766.
Kaliman, Perla et al., J. Biol. Chem. (1999), 274(25), 17437-17444, XP000960874.
El-Dada, Manar D. et al., J. Pharmacol. Exp. Ther. (1997), 281(3), pp. 1463-1470, XP000972194.
Allen, Ronald E. et al., Muscle Biology Group, Methods in Cell Biology, Skeletal Muscle Satellite Cell Cultures, vol. 52, 1998, pp. 155-176.
Alway, Stephen E., Journal of Gerontology: Biological Sciences, Overload-Induced C-Myc Oncoprotein Is Reduced in Aged Skeletal Muscle, 1997, vol. 52A, No. 4, pp. B203-B211.
Anderson, Judy E., Molecular Biology of the Cell, A Role of Nitric Oxide in Muscle Repair: Nitric Oxide-mediated Activation of Muscle Satellite Cells, vol. 11, pp. 1859-1874, May 2000.
Anderson, Judy E., Biochemistry Cell Biology, Studies of the dynamics of skeletal muscle regeneration: the mouse came back!, vol. 76, (1998), pp. 13-26.
Anderson, Judy E. et al., Muscle & Nerve, Dystrophy and Myogenesis in mdx Diaphragm muscle, 1998, vol. 21, pp. 1153-1165.
Anderson, Judy E. et al., Muscle & Nerve, Deflazacort But Not Prednisone Improves Both Muscle Repair and Fiber Growth in Diaphram and Limb Muscle in Vivo in the Mdx Dystrophic Mouse, 1996, vol. 19, pp. 1576-1585.

(Continued)

Primary Examiner—Jean C. Witz

(57) ABSTRACT

The present invention is directed to methods, pharmaceutical compositions and kits for modulating skeletal muscle precursor cell activation. Modulation is effected through the use of nitric oxide (NO), donors of NO, inhibitors of NO activity (NO inhibitor) or regulators of NO production, either locally or systemically. The invention further teaches the use of NO, an NO donor, an NO inhibitor or a regulator of NO production to modulate the effects of steroid hormone on skeletal muscle. The invention further provides a method for identifying a compound which effects a change in activation state of muscle precursor cells. A number of advantages is evident. By allowing skeletal muscle precursor cells to be manipulated directly, the invention enables specific treatments to regenerate and repair muscle.

28 Claims, 24 Drawing Sheets

OTHER PUBLICATIONS

Anderson, Judy E. et al., Experimental Cell Research, The Time Course of Basic Fibroblast Growth Factor Expression in Crush-Injured Skeletal Muscle of SJL/J and BALB/c Mice, (1995), vol. 216, pp. 325-334.

Anderson, Judy E. et al., Cell Transplantation, Deflazacort Increases Laminin Expression and Myogenic Repair, and Induces Early Persistent Functional Gain in mdx Mouse Muscular Dystrophy, vol. 9, 2000, pp. 551-564.

Appell, H.-J et al., Int. J. Sports Med., Satellite Cell Activation in Human Skeletal Muscle After Training: Evidence for Muscle Fibre Neoformation, vol. 9, (1998), pp. 297-299.

Balon, Thomas W. et al., J. Appl. Physiol., Nitric oxide release is present from incubated skeletal muscle preparations, vol. 77(6), 1994, pp. 2519-2521.

Beckman, Joseph S. et al., Nitric oxide, superoxide, and peroxynitrite: the good, the bad, and the ugly. Am. J. Physiol, vol. 271 (Cell Physiol. 40), 1996, pp. C1424-C1437.

Beesley, Julian E., Histochemical Journal, Histochemical methods for detecting nitric oxide synthase, vol. 27, (1995), pp. 757-769.

Bischoff, Richard., Developmental Biology, A Satellite Cell Mitogen from Crushed Adult Muscle, vol. 115, (1986), pp. 140-147.

Bischoff, Richard., Developmental Biology, Proliferation of Muscle Satellite Cells on Intact Myofibers in Culture, vol. 115, (1986), pp. 129-139.

Bischoff, Richard., The Journal of Cell Biology, Cell Cycle Commitment of Rat Muscle Satellite Cells, vol. 111, Jul. 1990, pp. 201-207.

Bischoff, Richard., Development, Interaction between satellite cells and skeletal muscle fibers, vol. 109, (1990), pp. 943-952.

Blandino, G. et al., J. Exp. Clin. Cancer Research., BCL-2: the Pendulum of the Cell Fate, vol. 16, 1997, pp. 3-10.

Brenman, Jay E., et al., Cell, Interaction of Nitric Oxide Synthase with the Postsynaptic Density Protein PSD-95 and α1-Syntrophin Mediated by PDZ Domains, vol. 84, Mar. 8, 1996, pp. 757-767.

Brenman, Jay E., et al., Cell, Nitric Oxide Synthase Complexed with Dystrophin and Absent from Skeletal Muscle Sarcolemma in Duchenne Musclar Dystrophy, vol. 82, Sep. 8, 1995, pp. 743-752.

Buonanno, Andres, et al., Nucleic Acids Research, The MyoD family of myogenic factors is regulated by electrical activity: isolation and characterization of a mouse Myf-5 cDNA, vol. 20, No. 3, 1991, pp. 539-544.

Busse, Rudi et al., J Vasc Res, Pulsatile Stretch and Shear Stress: Physical Stimuli Determining the Production of Endothelium-Derived Relaxing Factors, vol. 35, 1998, pp. 73-84.

Capanni, Cristina et al., Biochemical and Biophysical Research Communications, Increase ofNeuronal Nitric Oxide Synthase in Rat Skeletal Muscle during Ageing, vol. 245, (1998), pp. 216-219, Article No. RC988404.

Chambers, Rebecca L. et al., Can. J. Appl. Physiol., Molecular Basis of Skeletal Muscle Regeneration, vol. 21 (3), 1996, pp. 155-184.

Chang, Wen-Jinn, et al., Proc. Natl. Acad. Sci. USA, Neuronal nitric oxide synthase and dystrophin-deficient muscular dystrophy, vol. 93, Aug. 1996, pp. 9142-9147.

Chao, Daniel S. et al., J. Exp. Med, Selective Loss of Sarcolemmel Nitric Oxide Synthase in Becker Muscular Dystrophy, vol. 184. Aug. 1996, pp. 609-618.

Chen, Long-En et al., Am J. Physiol., Effects of S-nitroso-N-acetylcysteine on contractile function of reperfused skeletal muscle, vol. 274 (Regulatory Integrative Comp. Physiol. 43), 1998, pp. R822-R829.

Chien, Shu, et al., Hypertension, Effects of Mechanical Forces on Signal Transduction and Gene Expression in Endothelial Cells, 1998, vol. 31[part 2], pp. 162-169.

Cornelison D.D.W. et al., Developmental Biology, Single-Cell Analysis of Regulatory Gene Expression in Quiescent and Activated Mouse Skeletal Muscle Satellite Cells, vol. 191, (1997), pp. 270-283, Article No. DB978721.

Crosbie, Rachelle H. et al., Human Molecular Genetics, mdx muscle pathology is independent of nNOS perturbation, vol. 7, 1998, pp. 823-829.

Darr, Kevin C. et al., J. Appl. Physiol., Exercise-induced satellite cell activation in growing and mature skeletal muscle, vol. 63(5), 1987, pp. 1816-1821.

Darr, Kevin C. et al., J. Appl. Physiol., Hindlimb suspension suppresses muscle growth and satellite cell proliferation, vol. 67(5), 1989, pp. 1827-1834.

Decary, Stephanie et al., Human Gene Therapy, Telomere Length as a Tool to Monitor Satellite Cell Amplification for Cell-Mediated Gene Therapy, vol. 7, (Jul. 10, 1996), pp. 1347-1350.

Decary, S. et al., Human Gene Therapy, Replicative Potential and Telomere Length in Human Skeletal Muscle: Implications for Satellite Cell-Mediated Gene Therapy, vol. 8, (Aug. 10, 1997), pp. 1429-1438.

Decrouy, A. et al., Gene Therapy, Mini- and full-length dystrophin gene transfer induces the recovery of nitric oxide synthase at the sarcolemma of mdx4$^{cv}$ skeletal muscle fibres, vol. 5, (1998), pp. 59-64.

Graaf, J.C. de et al., Circulation, Nitric Oxide Functions as an Inhibitor of Platelet Adhesion Under Flow Conditions, vol. 85, 1992, pp. 2284-2290.

Dimmeler, Stephanie et al., Nature, Activation of nitric oxide synthase in endothelial cells by Akt-dependent phosphorylation, Jun. 1999, vol. 399, pp. 601-605.

Evan, Gerard et al., Science, A Matter of Life and Cell Death, vol. 281, Aug. 1998, pp. 1317-1326.

Floss, Thomas et al., Genes & Development, A role for FGF-6 in skeletal muscle regeneration, vol. 11, 1997, pp. 2040-2051.

Gal-Levi, Ronit et al., Biochimica et Biophysica Acta, Hepatocyte growth factor plays a dual role in regulating skeletal muscle satellite cell proliferation and differentiation, vol. 1402, (1998), pp. 39-51.

Garthwaite, J. et al., Annu. Rev. Physiol., Nitric Oxide Signaling in the Central Nervous System, vol. 57, 1995, pp. 683-706.

Gossrau, Reinhart, Acta Histochem., Caveolin-3 and nitric oxide synthase I in healthy and diseased skeletal muscle, vol. 100, (1998), pp. 99-112.

Grounds, Miranda D. et al., Cell Tissue Research, Identification of skeletal muscle precursor cells in vivo by use of MyoD1 and myogenin probes, vol. 267, (1992), pp. 99-104.

Grounds, Miranda D. et al., Cell Tissue Research, A model of myogenesis in vivo, derived from detailed autoradiographic studies of regenerating skeletal muscle, challenges the concept of quantal mitosis, vol. 250, (1987), pp. 563-569.

Grounds, Miranda D. et al., Cell Tissue Research, A comparison of muscle precursor replication in crush-injured skeletal muscle of Swiss and BALBc mice, vol. 255, (1989), pp. 385-391.

Grozdanovic, Zarko et al., Acta histochemica, Nitric oxide synthase I (NOS-I) is deficient in the sarcolemma of striated muscle fibers in patients with Duchenne muscular dystrophy, suggesting an association with dystrophin, vol. 98, (1996), pp. 61-69.

Grozdanovic, Z. et al., Histology and Histopathology, Nitric oxide synthase in skeletal muscle fibers: a signaling component of the dystrophin-glycoprotein complex, vol. 14, (1999), pp. 243-256.

Hemler, Martin E., Cell, Dystroglycan Versatility, vol. 97, May 28, 1999, pp. 543-546.

Huang, Paul L. et al., Cell, Targeted Disruption of the Neuronal Nitric Oxide Synthase Gene, vol. 75, Dec. 31, 1993, pp. 1273-1286.

Irintchev, A. et al., Developmental Dynamics, Expression Pattern of M-Cadherin in Normal, Denervated, and Regenerating Mouse Muscles, vol. 199, (1994), pp. 326-337.

Ishikawa, Harunori, Zeitschrift fur Anatomie und Entwicklungsgeschichte, Electron Microscopic Observations of Satellite Cells with Special Reference to the Development of Mammalian Skeletal Muscles, vol. 125, (1966), pp. 43-63.

Joyner, Michael J. et al., J. Appl. Physiol., Nitric oxide and vasodilation in human limbs, vol. 83(6), 1997, pp. 1785-1796.

Kami, Katsuya, Cell Tissue Research, Localization of myogenin, c-fos, c-jun, and muscle-specific gene mRNAs in regenerating rat skeletal muscle, vol. 280, (1995) pp. 11-19.

Kanner, Joseph et al., Archives of Biochemistry and Biophysics, Nitric Oxide as an Antioxidant, vol. 289, No. 1, Aug. 15, 1991, pp. 130-136.

Kapur, Sonia et al., Diabetes, Expression of Nitric Oxide Synthase in Skeletal Muscle, vol. 46, Nov. 1997, pp. 1691-1700.

Kleinogus, Catherine et al., Cell Tissue Research, Preliminary observations of satellite cells in undamaged fibres of the rat soleus muscle assaulted by a snake-venon toxin, vol. 230, (1983), pp. 671-676.

Kobzik, Lester et al.; Nature, Nitric oxide in skeletal muscle, vol. 372, Dec. 8, 1994, pp. 546-548.

Kroncke, Klaus-D. et al., Nitric Oxide: Biology and Chemistry, Nitric Oxide: Cytotoxicity versus Cytroprotection-How, Why, When, and Where?, vol. 1, No. 2, Apr. 1997, pp. 107-120, Article No. NO970118.

Kubes, P. et al., Proc. Natl. Acad. Sci. USA, Nitric oxide: An endogenous modulator of leukocyte adhesion, vol. 88, Jun. 1991, pp. 4651-4655.

Lancaster, J.R. Jr., Nitric Oxide: Biology and Chemistry, A tutorial on the Diffusibility and Reactivity of Free Nitric Oxide, vol. 1, No. 1, Feb. 1997, pp. 18-30.

Lancaster, J.R. Jr., Proc. Natl. Acad Sci. USA, Simulation of the diffusion and reaction of endogenously produced nitric oxide, vol. 91, Aug. 1994, pp. 8137-8141.

Landauer, JA et al., Aviation, Space, and Environmental Medicine, A Proposed Cause for and Prevention of Bone and Muscle Wasting in Microgravity, vol. 69, No. 7, Jul. 1998, pp. 699-702.

Li, Zhenlin et al., The Journal of Cell Biology, Desmin Is Essential for the Tensile Strength and Integrity of Myofibrils but Not for Myogenic Commitment, Differentiation, and Fusion of Skeletal Muscle, vol. 139, No. 1, Oct. 6, 1997, pp. 129-144.

Lowenstein, Charles J. et al., Cell, Nitric Oxide, A Novel Biologic Messenger, vol. 70, Sep. 4, 1992, pp. 705-707.

Lowenstein, Charles J. et al., Ann Intern Med., Nitric Oxide, A Physiologic Messenger, vol. 120, 1994, pp. 227-237.

Mauro, ALexander, J. Biophys Biochem cytol, Satellite Cell of Skeletal Muscle Fibers, vol. 19, 1961. pp. 493-495.

McCall, Therese B. et al., Eur. J. Immunol., Induction of nitric oxide synthase in rat peritoneal neutrophils and its inhibition by dexamethasone, vol. 21, 1991, pp. 2523-2527.

McIntosh, L.M., et al., Biochemistry Cell Biology, Hypothyroidism prolongs and increases mdx muscle precursor proliferation and delays myotube formation in normal and dystrophic limb muscle, vol. 73, 1995, pp. 181-190.

McIntosh, Laura M. et al., The Anatomical Record, Regeneration and Myogenic Cell Proliferation Correlate With Taurine Levels in Dystrophin- and MyoD-Deficient Muscles, vol. 252, 1998, pp. 311-324.

McIntosh, L.M. et al., Muscle & Nerve, The Effects of Altered Metabolism (Hypothyrodism) on Muscle Repair in the mdx Dystrophic Mouse, vol. 17, 1994, 444-453.

Megeney, Lynn A., Genes & Development, MyoD is required for myogenic stem cell function in adult skeletal muscle, vol. 10, 1996, pp. 1173-1183.

Miyazawa, Keiji et al., The Journal of Biological Chemistry, Proteolytic Activation of Hepatocyte Growth Factor in Response to Tissue Injury, vol. 269, No. 12, Issue of Mar. 25, 1994, pp. 8966-8970.

Moor, A.N. et al., Microscopy Research and Technique, Cell Cycle Behavior and MyoD Expression in Response to T3 Differ in Normal and mdx Dystrophic Primary Muscle Cell Cultures, vol. 48, (2000), pp. 204-212.

Moore, Robert et al., Development, The Cell adhesion molecule M-cadherin is specifically expressed in developing and regenerating, but not denervated skeletal muscle, vol. 117, (1993), pp. 1409-1420.

Nakane, Masaki, et al., Federation of European Biochemical Societies, Cloned human brain nitric oxide synthase is highly expressed in skeletal muscle, vol. 316, No. 2, 1993, pp. 175-180.

Nathan, Carl et al., Cell, Nitric Oxide Synthases: Roles, Tolls, and Controls, vol. 78, Sep. 23, 1994, pp. 915-918.

Palmer, Richard M.J., Arch Surg., The Discovery of Nitric Oxide in the Vessel Wall, vol. 128, Apr. 1993, pp. 396-401.

Pernitsky, A.N. et al., Experimental Cell Research, Differential Effects of 3,5,3'-Triiodothyronin on Control and mdx Myoblasts and Fibroblasts: Analysis by Flow Cytometry, vol. 227, (1996), pp. 214-222, Article No. 0270.

Pernitsky, A.N., et al., Biochemistry Cell Biology, Hyperthyroidism impairs early repair in normal but not dystrophic mdx mouse tibialis anterior muscle. An in vivo study, vol. 74, (1996), pp. 315-324.

Reid, M.B., Acta Physiol Scand, Role of nitric oxide in skeletal muscle: synthesis, distribution and functional importance, vol. 162, 1998, pp. 401-409.

Ribera, Joan et al., Journal of Neuroscience Research, Nitric Oxide Synthase in Rat Neuromuscular Junctions and in Nerve Terminals of Torpedo Electric Organ: Its Role as Regulator of Acetylcholine Release, vol. 51, (1998), pp. 90-102.

Rong, Sing et al., Proc. Natl. Acad. Sci. USA, Invasiveness and metastasis of NIH 3T3 cells induced by Met-Hepatocyte growth factor/ scatter factor autocrine stimulation, vol. 91, May 1994, pp. 4731-4735.

Rose, Olaf et al., Developmental Dynamics, Expression of M-Cadherin Protein in Myogenic Cells During Prenatal Mouse Development and Differentiation of Embryonic Stem Cells in Culture, vol. 201, (1994), pp. 245-259.

Rubanyi, Gabor M. et al, Am. J. Physiol., Flow-induced release of endothelium-derived relaxing factor, vol. 250 (Heart Circ. Physiol. 19), 1986, pp. H1145-H1149.

Rubinstein, Irit et al., J. Clin. Invest., Involvement of Nitric Oxide System in Experimental Muscle Crush Injury, vol. 101, No. 6, Mar. 1998, pp. 1325-1333.

Rudnicki, Michael A. et al., BioEssays, The MyoD family of transcription factors and skeletal myogenesis, vol. 17, No. 3, 1995, pp. 203-209.

Schmidt, Harald H.H. W. et al., Cell, NO at Work, vol. 78, Sep. 23, 1994, pp. 919-925.

Schultz, Edward, Am. J. Anat., Fine Structure of Satellite Cells in Growing Skeletal Muscle, vol. 147, 1976, pp. 49-70.

Schultz, Edward et al., The Journal of Experimental Zoology, Satellite Cells are Mitotically Quiescent in Mature Mouse Muscle: an EM and Radioautographic Study, vol. 206, No. 3, Dec. 1978, pp. 451-456.

Schultz, Edward et al., Muscle & Nerve, Response of Satellite Cells to Focal Skeletal Muscle Injury, vol. 8, 1985, pp. 217-222.

Schultz, Edward et al., Rev. Physiol. Biochem. Pharmacol., Skeletal Muscle Satellite Cells, vol. 123, 1994, pp. 213-257.

Shen, Weiqun et al., Medicine and Science in Sports and Exercise, Nitric oxide production and NO synthase gene expression contribute to vascular regulation during exercise, vol. 27, No. 8, 1995, pp. 1125-1134.

Silvagno, Francesca et al., The Journal of Biological Chemistry, Neuronal Nitric-oxide syntahse-$\mu$, an Alternatively Spliced Isoform Expressed in Differentiated Skeletal Muscle, vol. 271, No. 19, Issue of May 10, 1996, pp. 11204-11208.

Snow, Mikel, H., Cell and Tissue Research, The Effects of Aging on Satellite Cells in Skeletal Muscles of Mice and Rats, vol. 185, (1977), pp. 399-408.

Snow, Mikel H., The Anatomical Record, Satellite Cell Response in Rat Soleus Muscle Undergoing Hypertrophy Due to Surgical Ablation of Synergists, vol. 227, 1990, pp. 437-446.

Tatsumi, Ryuichi, et al., Developmental Biology, HGF/SF Is Present in Normal Adult Skeletal Muscle and Is Capable of Activating Satellite Cells, vol. 1994, (1998), pp. 114-128.

Tews, Dominique S. et al., Clinical Immunology and Immunopathology, Cell Death and Oxidative Damage in Inflammatory Myopathies, vol. 87, No. 3, Jun. 1998, pp. 240-247.

Tews, Dominique S. et al., Journal of Neuropathology and Experimental Neurology, Expression of Different Isoforms of Nitric Oxide Synthase in Experimentally Denervated and Reinnervated Skeletal Muscle, vol. 56, No. 12, Dec. 1997, pp. 1283-1289.

Tews, Dominique S. et al., Experimental Neurology, Expression Profile of Stress Proteins, Intermediate Filaments, and Adhesion Molecules in Experimentally Denervated and Reinnervated Rat Facial Muscle, vol. 146, (1997), pp. 125-134.

Tidball, James G. et al., Am, J. Physiol., Mechanical loading regulates NOS expression and activity in developing and adult skeletal muscle, vol. 275(Cell Physiol. 44), 1998, C260-C266.

Traub, Oren, et al., Arterioscler Thromb Vasc Biol., Laminar Shear Stress Mechanisms by Which Endothelial Cells Transduce an Atheroprotective Force, vol. 18, 1998, pp. 677-685.

Wakayama, Yoshihiro et al., Acta Neuropathol, Ultrastructural localization of $\alpha$1-syntrophin and neuronal nitric oxide synthase in normal skeletal myofiber, and their relation to each other and to dystrophin, vol. 94, (1997), pp. 455-464.

Wang, Helen H. et al., Can. J. Physio. Pharmacol., Evidence of nitric oxide, a flow-department factor, being a trigger of liver regeneration in rats, vol. 76, 1998, pp. 1-8.

Wang, Ti et al., Nature, Nitric oxide mediates activity-dependent synaptic suppression at developing neuromuscular synapses, vol. 374, Mar. 16, 1995, pp. 262-266.

Weis, Joachim, Acta Neuropathol, Jun, Fos, MyoD1, and Myogenin proteins are increased in skeletal muscle fiber nuclei after denervation, vol. 87, (1994), pp. 63-70.

White, Timothy P. et al., Medicine and Science in Sports and Exercise, Satellite Cell and Growth Factor Involvement in Skeletal Muscle Growth, vol. 21, No. 5 (Supplement), 1989, pp. S158-S163.

Winchester, P.K. et al., Am. J. Physiol., Satellite cell activation in the stretch-enlarged anterior latissimus dorsi muscle of the adult quail, vol. 260 (Cell Physiol. 29), 1991, pp. C206-C212.

Young, M. E., et al., Biochem. J., Evidence for altered sensitivity of the nitric oxide/cGMP signalling cascade in insulin-resistant skeletal muscle, vol. 329, (1998), pp. 73-79.

Yun, Kyuson, Current Opinion in Cell Biology, Skeletal muscle determination and differentiation: story of a core regulatory network and its context, vol. 8, 1996, pp. 877-889.

Zacharias, J.M. et al., Journal of the Neurological Sciences, Muscle regeneration after imposed injury is better in younger than older mdx dystrophic mice, vol. 104, 1991, pp. 190-196.

* cited by examiner

FIG. 4B
FIG. 4D
FIG. 4A
FIG. 4C

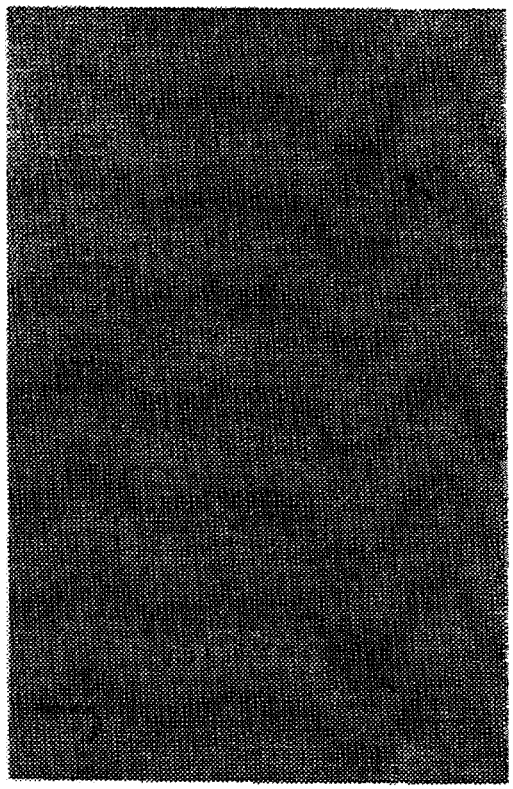
FIG. 6J
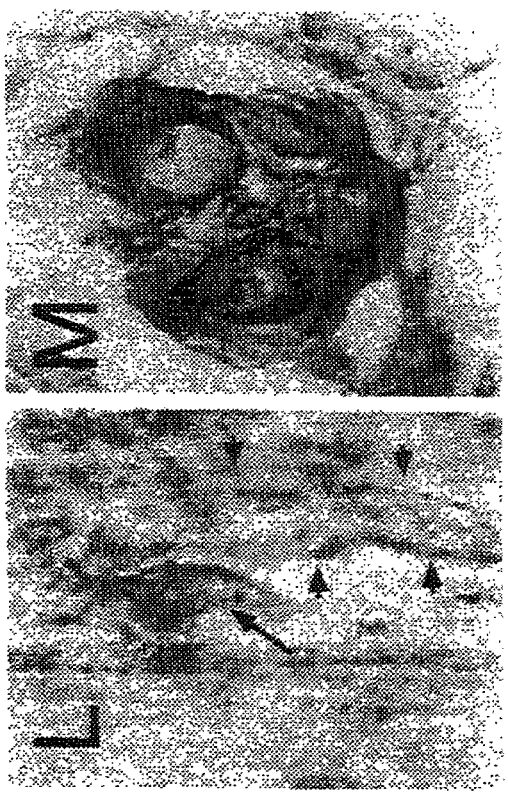
FIG. 6M
FIG. 6L
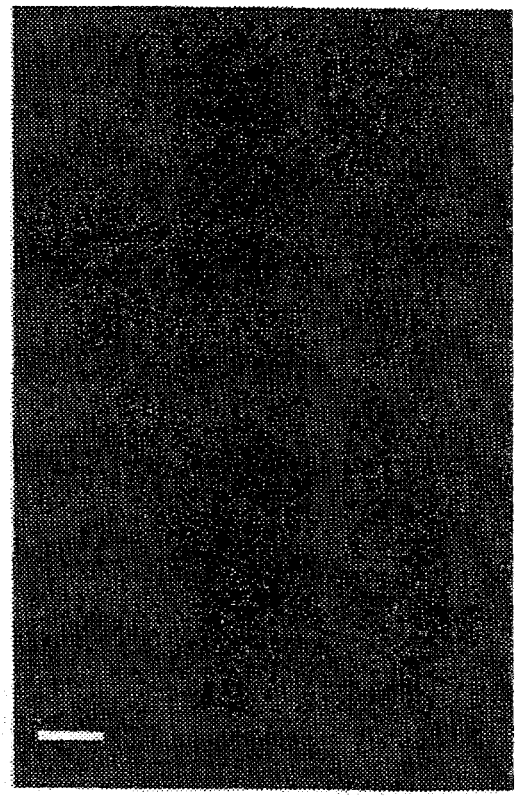
FIG. 6I
FIG. 6K

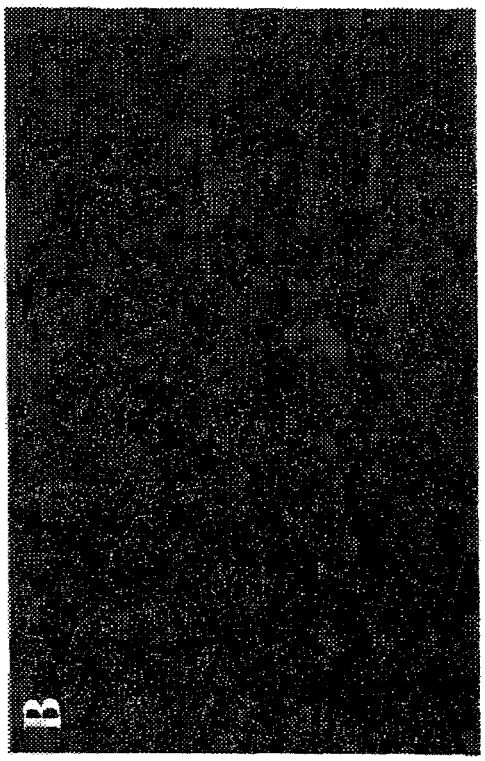
FIG. 12B
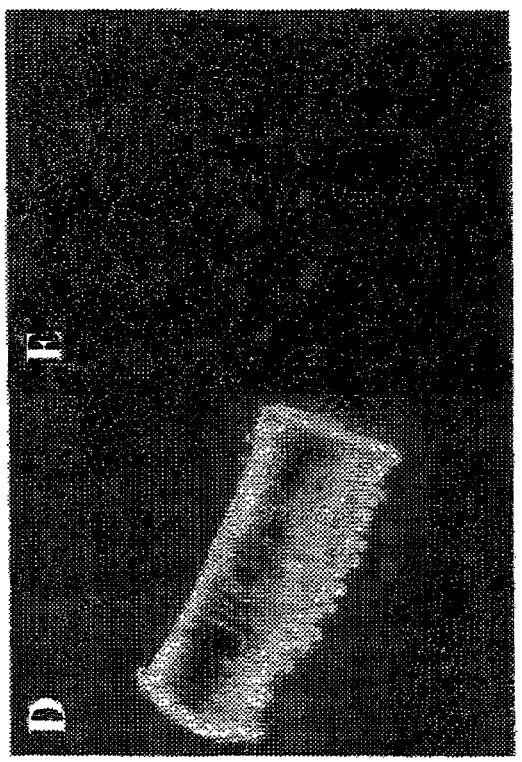
FIG. 12E
FIG. 12D
FIG. 12A
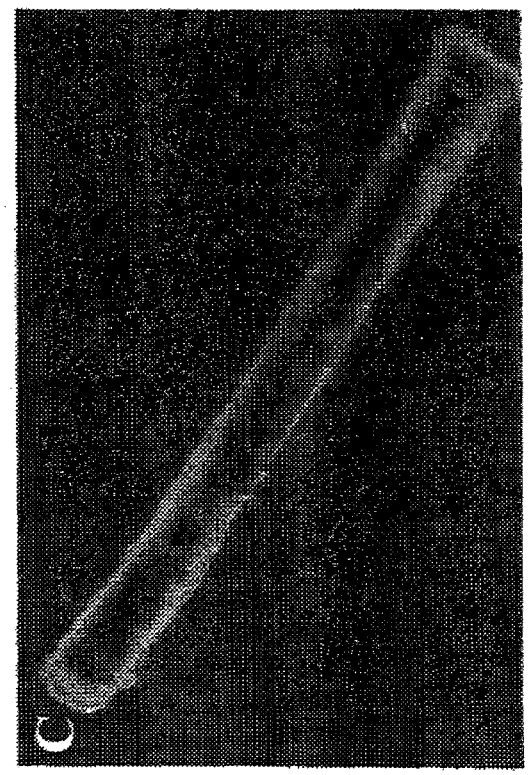
FIG. 12C

NITRIC OXIDE MANIPULATION OF MUSCLE SATELLITE CELL ACTIVATION

This application claims the benefit of U.S. Provisional Application No. 60/123,895, filed Mar. 11, 1999.

FIELD OF INVENTION

The present invention relates generally to skeletal muscle proliferation. More specifically, the invention relates to nitric oxide as a modulator of skeletal muscle precursor cell activation, and to uses of nitric oxide to improve muscle formation and repair in normal and disease states.

BACKGROUND OF THE INVENTION

Skeletal muscle arises after the induction of the mesoderm. After differentiation of the mesoderm into dorsal, intermediate, and lateral mesoderm, the dorsal mesodermal mesenchyme differentiates to form myotomes which, in turn, differentiate to give rise to the myogenic precursor cells which ultimately form skeletal muscle. Unlike the myogenic precursor cells of the heart, the skeletal muscle precursors fuse side-to-side to form unbranched, multinucleated myofibers. Some of the skeletal myogenic precursor cells do not differentiate and fuse into myocytes (also called myofibers) but, rather, attach to the outside of the plasmalemma of the myocytes. These cells participate in muscle growth during maturation and typically thereafter will remain, throughout adulthood, as largely undifferentiated, quiescent skeletal muscle "satellite cells." Upon injury of a skeletal muscle, these satellite cells are revealed to be myogenic precursor cells, or muscle "stem cells," which proliferate and differentiate, again by fusion, into new and functional skeletal muscle. Even after injury, some of the proliferated satellite cells remain undifferentiated and attach to the newly formed myofibers. Thus, the satellite cells of skeletal muscle provide a constant and renewable source myogenic precursor cells which allows for skeletal muscle repair and regeneration throughout mammalian life.

The proliferation and differentiation of skeletal muscle satellite cells has been extensively studied in vitro. For example, a simple saline extract of skeletal muscle has been shown to cause satellite cells to proliferate in culture (Bischoff (1989) in Myoblast Transfer Therapy, Griggs and Karpati, eds., pp. 147–158). Similarly, it has been shown that chick embryo extract or the conditioned medium of differentiated myotubes from young mice exhibits a strong mitogenic effect on satellite cells, but that conditioned medium from older murine myotubes has a lesser effect (Mezzogiorno et al. (1993) Mech. Ageing & Develop. 70:35–44). In addition, a number of hormones and growth factors have ben found to enhance satellite cell proliferation, including FGF, PDGF, ACTH, LIF, IGF (Bischoff (1989); Mezzogiorno et al. (1993)) and HGF (Tatsumi et al., (1998) Dev Biol 194: 114–128). Conversely, TGF-$\beta_1$ is widely believed to inhibit satellite cell proliferation, as does contact with the myofiber plasmalemma, but not the basal lamina (Bischoff (1989); but see Hathaway et al. (1991) J. Cell Physiol. 146:435–441).

After muscle injury, satellite cells are activated and recruited to cycle as precursors for new muscle formation. Between injury and proliferation in vivo, satellite cells express immediate early genes after 3–6 hr., (Weiss, (1994) Acta Neuropathol. 87: 63–70; Kami, K., Noguchi, K., and Senba, E., (1995) Cell Tissue Res. 280: 11–19) and muscle regulatory genes after 6 hr. (Grounds, M. D., Garrett, K. L., Lai, M. C. Wright, W. E., and Bielharz, M. W. (1992) Cell Tissue Res. 267: 99–104) in concert with proliferating cell nuclear antigen (Chambers, R. L., and McDermott, J. C., (1996) Can. J. Appl. Physiol. 21: 155–184). The expression of these genes, release of growth factors like bFGF and DNA synthesis 24–30 hr. later are used to characterize muscle regeneration in injured and dystrophic muscle (Grounds, M. D., and McGeachie, J. K. (1989) Cell Tissue Res. 255: 385–391; Anderson, J. E., et al. (1995) Exp. Cell Res. 216: 325–334; Anderson, J. E. et al. (1998) Muscle Nerve 21: 1153–1165; Floss, T., Arnold, H.-H., and Braun, T., (1997) Genes Dev. 11: 2040–2051). The timing and sequence of events are specific to repair (Megeney, L. A., Kablar, B., Garrett, K., Anderson J. E., and Rudnicki, N. A., (1996) Genes Dev. 10: 1173–1183; Li, Z., Mericskay, M., Agbulut, O., Butler-Browne, G. Carlsson, L., Thronell, L. E., Babinet, C., and Paulin, D., (1997) J. Cell Biol. 139: 129–144; McIntosh, L. M., Garrett, K. L., Megeney L., Rudnicki, M. A., and Anderson, J. E., (1998b) Anat. Rec. 252: 311–324) although similar to development (Rudnicki, M. A., and Jaenisch, R., (1995) Bioessays 17: 203–209; Yun, K., and Wold, B. (1996) Current Opinion Cell Biol. 8: 877–889).

The fine structure of satellite cells, positioned intimately between the fiber sarcolemma and external lamina (Mauro, A. (1961) J. Biophys. Biochem. Cytol. 87: 225–251; Ishikawa, H. (1966) Z. Anat. Entwicklungsgesch 125: 43–63) changes during their transition from quiescence to activation. Nuclei enlarge and become euchromatic. The typical attenuated organelle-poor cytoplasm expands and organelles such as mitochondria and rough endoplasmic reticulum hypertrophy (Schultz (1976) Am. J. Anat. 147: 49–70; Snow (1977) Cell Tissue Res. 185, 399–408; Schultz et al. (1978) J. Exp. Zool. 206: 451–456; Schultz et al. (1985) Muscle Nerve 8: 217–222). However, while activation is recognised as essential to repair and defined as precursor stimulation and recruitment to cycle (Bischoff, R. (1990a). J. Cell Biol. 111: 201–207), the initial signal, timing and character of activation are not known (Schultz and McCormick (1994) Rev. Physiol Biochem. Pharmacol. 123: 213–257).

To date, the earliest indicator of satellite cell transformation during activation is the co-localization of hepatocyte growth factor (also called scatter factor, HGF/SF) with its receptor c-met shortly after injury in normal rat muscle (Tatsumi et al. (1998) Dev. Biol. 194: 114–128). In normal and regenerating muscle, satellite cells express c-met (Cornelison and Wold (1997) Dev. Biol. 19: 270–283; Tatsumi et al. (1998) Dev. Biol. 194: 114–128) and m-cadherin (Moore and Walsh (1993) Development 110: 1409–1420; Irinchev et al. (1994) Dev. Dynamics 199: 326–337; Rose et al. (1994) Dev. Dynamics 201: 245–259). While HGF/SF also plays a role in differentiation (Gal-Levi et al. (1998) Biochim. Biophys. Acta. 1402: 39–51.), it is the activating agent in extracts from crushed muscle (Tatsumi et al. (1998) Dev. Biol. 194: 114–128). Thus, the shift of HGF/SF from the periphery of the intact fiber to satellite cells means that activation follows soon after muscle damage.

Other observations indicate that the activation signal is transmitted along fibers from the site of direct injury. After segmental damage, satellite cells proliferate and fuse to form new myotubes both adjacent to the injury (Grounds and McGeachie (1987) Cell Tissue Res. 250: 563–569) and also at some distance from the injury near the ends of fibers (Klein-Ogus and Harris (1983) Cell Tissue Res. 230: 671–676; Schultz et al. (1985) Muscle Nerve 8: 217–222; Bischoff (1990) Development 109: 943–952; Grounds et al. (1992) Cell Tissue Res. 267: 99–104; McIntosh et al. (1994) Muscle Nerve 17: 444–453; McIntosh and Anderson (1995)

Biochem. Cell Biol. 73: 181–190). Satellite cells are activated without trauma and make DNA after exercise, training, stretch, cold, compression, hypertrophy, suspension and denervation (Bischoff (1986a) Dev. Biol. 115: 140–147; Bischoff (1986) Dev. Biol. 111: 129–139; Bischoff (1990b) Development 109: 943–952; Darr and Schultz: (1987) J. Appl. Physiol. 63: 1816–1821; Darr and Schultz (1989) J. Appl. Physiol. 67: 1827–1834; Appell et al. (1988) Int. J. Sports Med. 9: 297–299; White and Esser (1989) Med. Sci. Sports Exerc. 21: S158–S16; Snow (1990) Anat. Rec. 227: 437–446; Winchester et al. (1991) Am. J. Physiol 260 (Cell Physiol 29): C206–C212; Buonanno et al. (1992) Nucleic Acids Res. 20: 539–544; Always (1997) J. Gerontol. A. Biol. Sci. Med. Sci. 52: B203–B211). Therefore, multiple signals initiate or mediate activation. Nonetheless, it is clear that DNA synthesis some 24–30 hr after injury is a delayed index of prior and completed satellite cell activation.

From the above description of the art, it is clear that muscle repair and formation are enabled by satellite cell activation and recruitment to cycle. However, the immediate chemical signal that triggers such activation and recruitment has not been identified. Consequently, current treatments aimed at improving muscle repair and formation in both normal and disease states have been limited to physical therapy treatments, non-specific treatments, such as the use of hormones, that affect multiple metabolic systems, treatments which involve transplantation of muscle cells, and treatments based on gene therapy. Other treatments to improve the state of muscle health have been directed to the modulation of muscle contraction (U.S. Pat. No. 5,583,101), rather than to the crucial initial activation events that enable the regeneration of healthy muscle. Notably, transplantation and gene therapy treatments are both at early experimental stages and their use requires a high level of expertise to perform.

One treatment aimed at muscle repair and formation is the use of hormones. It is known in the art that growth hormones promote increase in muscle mass. Such hormones (including the class of anabolic androgenic steroids) have been used in farm animals under experimental conditions. Glucocorticoids (e.g. deflazacort and prednisone) have been prescribed to Duchenne muscular dystrophy patients. However, because hormones tend to be involved in multiple physiological processes, their beneficial effects are often accompanied by many dose-limiting side-effects. The glucocorticoids, in particular, possess anti-inflammatory and immunomodulatory activities. The major side effects of the glucocorticoids are hypertension, peptic ulcers, increased susceptibility to infections, osteoporosis, hyperglycemia, and vascular occlusion (WO97/41144).

Another treatment aimed at muscle repair and formation involves the transfer of muscle cells (myoblasts) to the injured site. Autologous mouse skeletal muscle cells have been explanted from a healthy muscle, proliferated in vitro, and then implanted into a necrotized skeletal muscle site (Alameddine and Fardeau (1989) in Myoblast Transfer Therapy, Griggs and Karpati, eds., pp. 159–166). It was shown that the transplanted satellite cells were able to populate the necrotized area and differentiate into functional myotubes which then mature into fully functional myofibers. Similarly, PCT Publication WO 96/28541 discloses that histocompatible donor mouse myoblasts can be implanted into the weakened muscle of a mouse model of muscular dystrophy and differentiate into myofibers. In addition, it is shown that growth of the myoblasts in bFGF results in significantly more new myofibers at the implant site. In humans, clinical trials of myoblast transplantation have had limited or disappointing results (Karpati, G. et al. Clin. Genet (1999) 55: 1–8). Thus, skeletal muscle satellite cells, proliferated in vitro, may be able to serve as a source of myogenic precursor cells for muscle restoration or regeneration therapy.

The ability of skeletal muscle satellite cells to restore or regenerate injured skeletal muscle has led some researchers to test whether myogenic precursor cells could be used to replace lost or damaged myocardial muscle. For example, mouse fetal cardiomyocytes, which are not terminally differentiated and retain the ability to divide, have been directly injected into the myocardium of a syngeneic adult mouse, and have been shown to form new and apparently functional myocardium (Soonpaa et al. (1994) Science 264: 98–101). Significantly, it has been shown that skeletal muscle satellite cells, explanted from adult canine skeletal muscle can be proliferated in vitro and implanted into a site of myocardial cryoinjury, where they appear to differentiate into "cardiac-like" muscle cells, possibly in response to morphogenic signals present in the myocardium (Chiu et al. (1995) Ann. Thorac. Surg. 60:12–18).

Although myoblast transfer is a promising treatment, it is still not effective in restoring adequate numbers of functional fibers to a diseased muscle. Transfer of myoblasts collected from a donor and amplified in culture may allow sufficient quantity, but involves immune rejection and suppression problems. Morphogens that induce proliferation of myogenic precursor cells have been used to treat damage to the myocardium (WO 98/27995).

As an alternative treatment to cell-based therapies to deliver dystrophin, gene therapy has been used to provide, on an experimental basis, the active counterpart of the missing or mutated protein to the muscle precursor cells prior to injection of the precursor cells into the muscle (e.g. WO 91/12329). However, gene transfer in mammals has only limited success due to low level expression of the therapeutic protein in vivo (Partridge et al. (1991) Muscle Nerve 14: 197–212; Partridge et al. Nature Medicine (1998) 4: 1208–1209), difficulties with delivery of the gene to targetted myogenic cells (Feero WG et al. (1997) Gene Therapy 4: 664–674), and immune responses (Partridge TA. Myoblast transplantation. In: Lanza RP et al., (eds) Yearbook of Cell and Tissue Transplantation 1996/1997. Kluwer Academic Publications (1996) p 53–59, Netherlands; Guerette B. et al. (1997) Cell Transplantation 6: 101–107).

Accordingly, there exists a need for treatments that enable muscle repair and formation based on the innate ability of muscle to regenerate new muscle after injury.

SUMMARY OF THE INVENTION

The present invention is directed to methods, pharmaceutical compositions and kits, for modulating skeletal muscle precursor cell activation. Modulation is effected through the use of nitric oxide (NO), donors of NO, inhibitors of NO activity (NO inhibitor) or regulators of NO production.

It is a feature of the present invention to modulate skeletal muscle precursor cell activation by nitric oxide.

According to one aspect, the invention provides a use of NO, an NO donor, an NO inhibitor, or a regulator of NO production to modulate activation of muscle precursor cells. Local or systemic activation is further provided.

According to one aspect, the invention provides a use of NO, an NO donor, or a regulator of NO production to increase activation of muscle precursor cells, thereby improving muscle regeneration and/or repair. Local or systemic activation is further provided.

According to another aspect, the invention provides use of an inhibitor of NO activity or an inhibitor of NO production to decrease activation of skeletal muscle precursor cells, thereby limiting proliferation of skeletal muscle precursor cells. Local or systemic decrease is further provided.

According to another aspect, the invention provides a method of amplifying muscle cells in culture, comprising placing NO, an NO donor, or a regulator of NO production into contact with muscle cells.

According to another aspect, the invention provides a method for obtaining a muscle cell population in culture, comprising use of NO, an NO donor, or a regulator of NO production.

According to another aspect, the invention provides a composition comprising muscle cells and a compound selected from the group consisting of NO, an NO donor and a regulator of NO production.

According to another aspect, the invention provides use of NO, an NO donor, an NO inhibitor or a regulator of NO production to modulate the effects of steroid hormone on skeletal muscle. Notably, NO has been used as "an agent to enhance the action of corticosteroids in the treatment of various diseases" (WO 98/41144). However, the use disclosed therein has been directed exclusively to treatment of anti-inflammatory, autoimmune or cardiovascular disease.

According to another aspect, the invention provides a composition comprising any one of the group consisting of NO, an NO donor, an NO inhibitor and a regulator of NO production, and a diluent or carrier suitable for use in muscle, for modulating activation of muscle precursor cells.

According to another aspect, the invention provides a composition comprising a compound selected from the group consisting of NO, an NO donor, an NO inhibitor and a regulator of NO production, and a component suitable for increasing concentration of the compound in muscle, for modulating activation of muscle precursor cells.

According to another aspect, the invention provides a commercial package containing as an active ingredient NO, an NO donor, an NO inhibitor or a regulator of NO production, together with instructions for its use for modulating activation of muscle precursor cells.

According to another aspect, the invention provides a method for validating a test wherein a change in activation state of muscle precursor cells is determined, comprising use of a DNA intercalator to determine that fibers associated with the precursor cells are intact.

According to another aspect, the invention provides a method for validating a test wherein a fiber hypercontraction-dependent change in activation state of muscle precursor cells is determined, comprising use of a myotoxin and a DNA intercalator to determine fiber membrane damage.

According to another aspect, the invention provides a method for identifying a compound which effects a change in activation state of muscle precursor cells, comprising: determining that fibers associated with the precursor cells are intact; determining the activation state of precursor cells in the absence of the compound; and determining the activation state of precursor cells treated with the compound; wherein the difference between the two activation states identifies the compound as a compound which effects a change in activation state of muscle precursor cells.

According to another aspect, the invention provides a method for identifying a compound which effects a fiber hypercontraction-dependent change in activation state of muscle precursor cells, comprising: treating an intact fiber containing precursor cells with a myotoxin and a DNA intercalator to effect fiber hypercontraction; determining the activation state of precursor cells in the absence of the myotoxin, DNA intercalator and the compound; and determining the activation state of precursor cells treated with the compound in the absence of the myotoxin and DNA intercalator; wherein the difference between the two activation states identify the compound as a compound which effects a fiber hypercontraction-dependent change in activation state of muscle precursor cells.

The present invention offers a number of advantages. By allowing skeletal muscle precursor cells to be manipulated directly, the invention enables specific treatments to make more new muscle more quickly and avoid extensive use of immunosuppressive drugs for myoblast transfer. The present invention also complements myoblast transfer protocols by reducing the need for an industrial tissue culture facility to amplify muscle precursors prior to transfer. The present invention further extends the beneficial effects of glucocorticoid treatments by providing maximally available and activated precursor cells for the proliferative and fusion-promoting effects mediated by glucocorticoid drugs. Treatments of normal muscle by physical therapy (e.g. in aging persons, after a stroke or coma, post-surgery recovery, physical training in preparation for spaceflight and during weightlessness) can also be supplemented by the present invention. From an agricultural perspective, promotion and acceleration of muscle growth by manipulating precursor cell activation could be of economic benefit.

BRIEF DESCRIPTION OF THE DRAWINGS

The invention is described with reference to the drawings as follows.

Figure 1A:
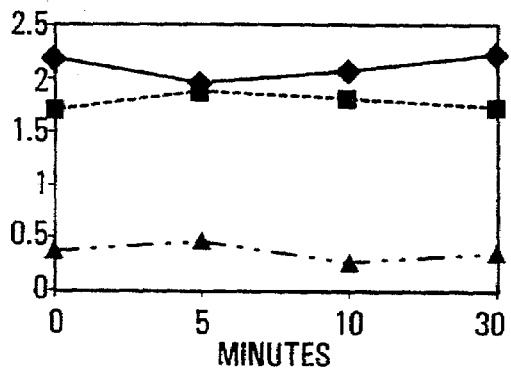
FIG. 1: Representative graphs from one experiment each on normal control (C57BL/6, A–H) and mdx mice (I–L). Panels show the time course of changes in muscle weight to body weight (mg/g) (A–D, I, J) and cell yields (cells/muscle×$10^5$) (E–H, K, L) in three muscles (RTA (♦), LTA(■) and RSOL (▲)) for groups of mice treated 30 min. before injury with saline (A, E, I, K), (Nω-nitro-L-arginine methyl ester (L-NAME) (B, F, J, L), L-Arg (C, G) and L-NAME plus L-Arg (D, H). Data from the same animals are represented for muscle weight and cell yield. In normal mice, the immediate rise in RTA yield in saline-treated animals was absent after L-NAME, and the transient rise in LTA yield at 10 min. was reduced by L-NAME treatment. In mdx mice, there was no immediate rise in RTA yield above the LTA basal level after injury, while at 10 min. RTA was increased. L-NAME treatment in mdx mice prevented the increased RTA yield at 10 min.
Figure 1B:
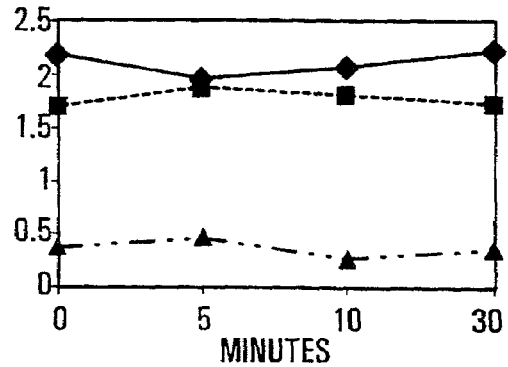
Figure 1C:
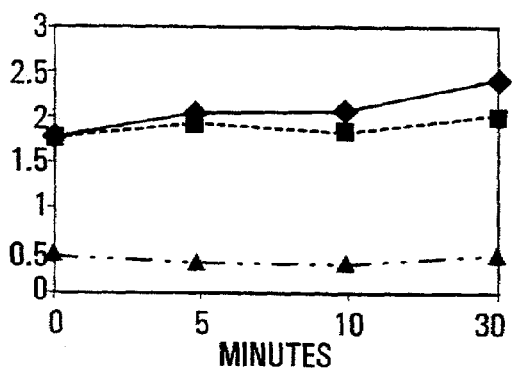
Figure 1D:
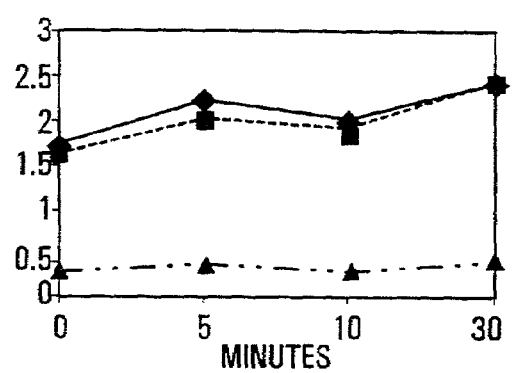
Figure 1E:
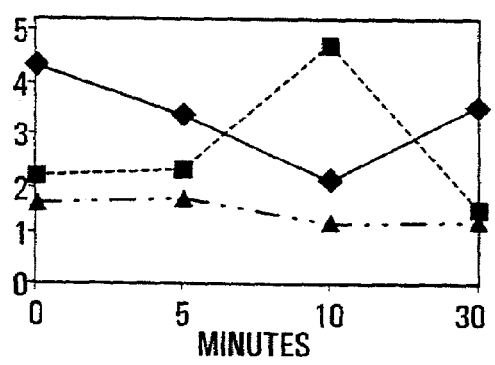
Figure 1F:
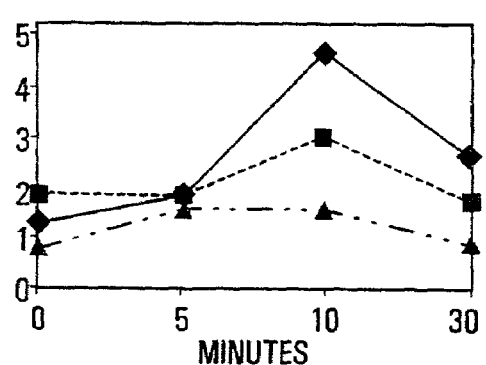
Figure 1G:
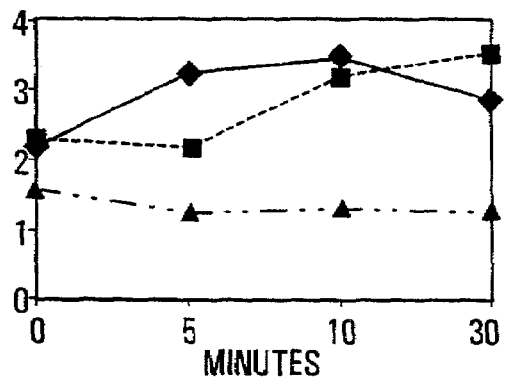
Figure 1H:
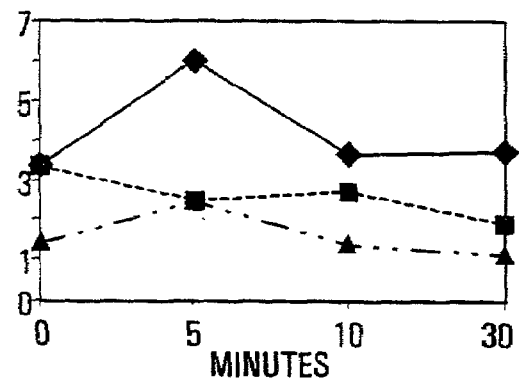

(I) After L-NAME, m-cadherin stains an attenuated satellite cell at 0 min. in RTA (J) Satellite cells are not prominent by H&E-staining of RTA at 0 min. (K) Thin strips of cytoplasm and a contoured nucleus are probable satellite cells (between arrowheads) at the fiber periphery in resin sections. (L) At high magnification, a myonucleus in a resin section from RTA 10 min. after injury shows a folded upper membrane near the contracted fibrilis. (M) 10 min. after injury, large m-cadherin-positive satellite cells are adjacent to an unstained fiber. (N) At 0 min. after injury, c-met (FITC) in satellite cells is not co-localized with HGF/SF (red). (O) A large satellite cell at 10. Min. after injury shows co-localization (yellow) of c-met (FITC) and HGF/SF (red) fluorescence. (P) A hypertrophic satellite cell (between arrowheads) is partly separated from an RTA fiber 10 min. after injury. Original magnification X330 except C&J, X132.

FIG. 5: L-NAME treatment over 6 days reduces normal muscle regeneration. (A) At low magnification (H&E) normal muscle repair after saline pretreatment includes a small necrotic crushed region (right of panel A), a region of adjacent mononuclear cells and myotubes (arrows) and surviving fiber segments (at the left). (B) New myotubes in the adjacent region contain many central nuclei and eosinophilic sarcoplasm after 6 days of regeneration. (C) New myotubes (arrows) are also present among surviving fibers. (D) After continuous L-NAME treatment for 6 days, the necrotic area (to the left) and adjacent region of mononuclear cells are enlarged, and few myotubes (arrow) are present. (E) Among mononuclear cells in the adjacent region, new myotubes (arrows) are thin and contain immature, basophilic cytoplasm. (F) Very few myotubes are found between surviving fiber segments at the ends of the RTA. Original magnification: A&D, X13; B, C, E, F, X132.

FIG. 6: A single L-NAME injection before injury affects myogenic repair in normal muscle. (A) At low magnification (H&E), the RTA 6 days after injury shows a large necrotic region (to the right), an adjacent area of mononuclear cells and small new myotubes (arrows), and surviving fiber segments (to the left). (B) At high magnification a myotube (arrow) extends between mononuclear cells and a fiber segment. (C) A very thin intensely eosinophilic myotube originates immediately beside a surviving fiber segment. (D) At higher magnification, the same myotube has formed from the satellite cell position apparently inside the external lamina. (E) An eosinophilic satellite cell (arrow) is elongated into a thin myotube. (F) A column of apparently unfused centrally-nucleated cells with granular cytoplasm makes up a myotube. (G) A BrdU-positive nucleus adjacent to a new myotube. (H&I) Thin new myotube segments are positive for devMHC (Texas red florescence) whether they extend from a larger myotube (H) or are located among mononuclear cells near the crush (I). (J) A crimson satellite cell (arrow) on an EDL fiber. (K) A large satellite cell (arrow) with crimson cytoplasm on a SOL fiber. (L) M-cadherin is present between a satellite cell (arrow) and a small new myotube (arrowheads). (M) M-cadherin staining is intense on satellite cells located on the four intrafusal muscle fibers in a spindle complex. Original magnification: A, X13; C, X33; B, E, M, X132; D, F-L, X330.

FIG. 7: A single treatment with L-NAME 30 min. before injury affects dystrophic muscle regeneration. (A) At low magnification (H&E) shows a large crush region (just at the left), an adjacent region of new myotubes (arrows) and surviving fiber segments (to the right). (B) Many large new myotubes adjacent to the crush. (C) Elongated mononuclear cells and myotubes are m-cadherin+. (D) An elongated crimson cell is binucleate and located in the satellite position on a surviving fiber segment. (E) A new myotube extends from a surviving segment and contains devMHC (Texas red fluorescence). (F) A BrdU-positive nucleus next to new myotubes with unstained central nuclei. (G) A new myotube contains apoptotic BrdU+ nuclear fragments. (H) Large c-met+satellite cells (FITC) on HGF/SF+fibers (Texas red) in LTA. (I) A large satellite cell (arrow) with granular cytoplasm (H&E) on an LEDL fiber less prominent margins than in undamaged normal muscles (FIG. 5J, K). Original magnification: A, X13; B, X130; C-I, X330.

FIG. 8: A model for the process of shear-induced, NO-mediated events that activate satellite cells after skeletal muscle injury. (A) In undamaged muscle with normal contraction and relaxation, thin quiescent satellite cells are demarcated by m-cadherin and contain few organelles. They are interposed between the overlying external lamina and the sarcolemma of a subjacent fiber, and are subject to pulsatile NO released from NOS-I$\mu$ that is anchored to syntrophin. Normally, NO diffuses cylindrically out from the fiber to act on cells and enzymes in the interstitium or is neutralized by red cell hemoglobin in the vessels that wrap each fiber. (B) After sarcolemmal injury, depolarization is not followed by repolarization. A single large contraction produces intense shear between the fiber membrane and external lamina. Shear induces a bolus release of NO that diffuses down its concentration gradient through the satellite cells hugging the fiber. (C) Satellite cells are becoming activated, and begin to enlarge as organelles such as mitochondria hypertrophy. HGF/SF from the damaged fiber is activated and shifts to the c-met receptor on satellite cells. Fibrils hypercontract and damaged segments retract within the external lamina, maintaining shear and NO release and activating cells along the fiber length. The adhesiveness of m-cadherin decreases and the damaged fiber releases proteins including HGF/SF to the interstitium. A released factor like HGF/SF, enters the circulation and can transiently activate distant satellite cells on undamaged muscles, although normal pulsatile NO release will mostly attenuate that response. Capillaries dilate and blood cells extravasate into the interstitium. (D) Fiber segments fully retract and satellite cells become motile precursors as HGF/SF binds to c-met. The external lamina remains as a scaffold for the satellite cells, now surrounded by less adhesive m-cadherin. The precursors may leave the fiber as the sequential expression of early immediate genes, muscle regulatory genes, proliferating cell nuclear antigen and later DNA synthesis begin prior to proliferation.

Figures 9A, 9B:

FIG. 9: Low magnification view of a representative muscle fiber and attached satellite cells from flexor digitorum brevis muscle of C57 mice after complete dissection (phase contrast×420; bar=50 μm). Connective tissue, nerves and vessels are absent. A) Live fiber—nuclei are observed in and on the fiber, and some appear bulging from fiber contour. B) Live and hypercontracted fibers. The hypercontracted fiber was damaged during the isolation procedure and is approximately ⅕$^{th}$ the size of the live fiber. These figures show that satellite cells cannot be identified by phase contrast.

Figures 10A, 10B, 10C:
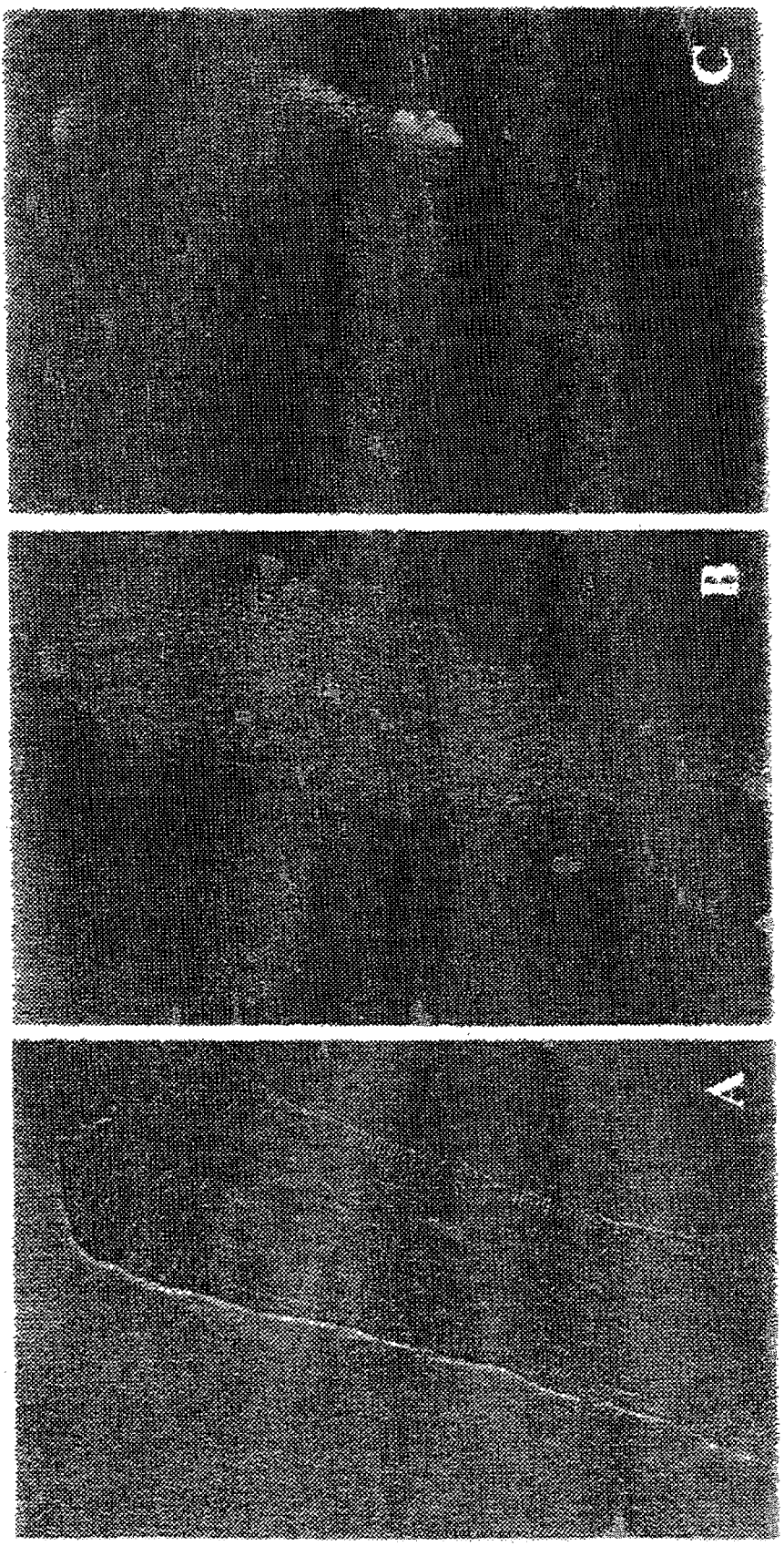
Figure 11B:
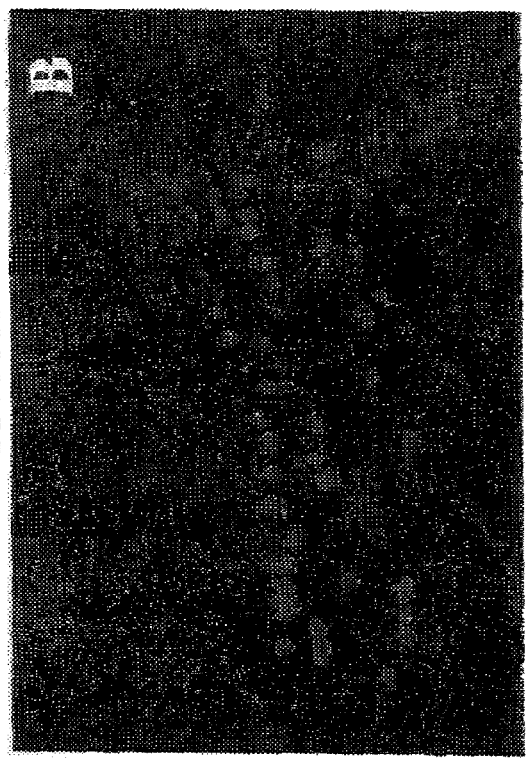
Figure 11D:
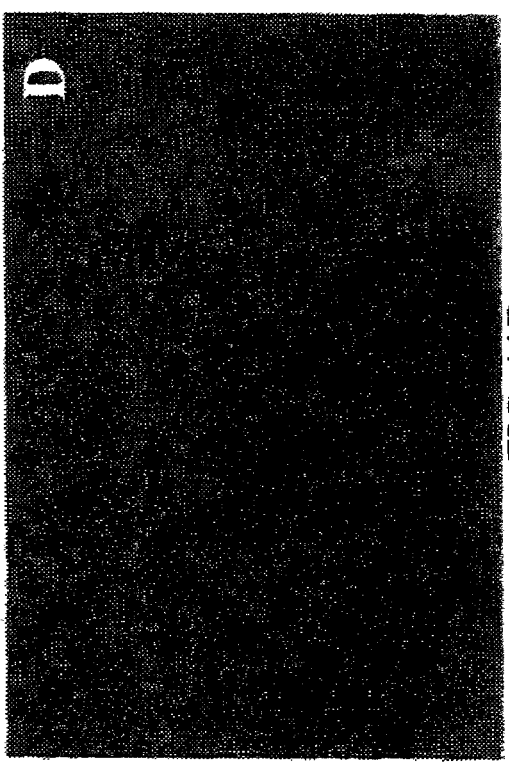
Figure 11A:
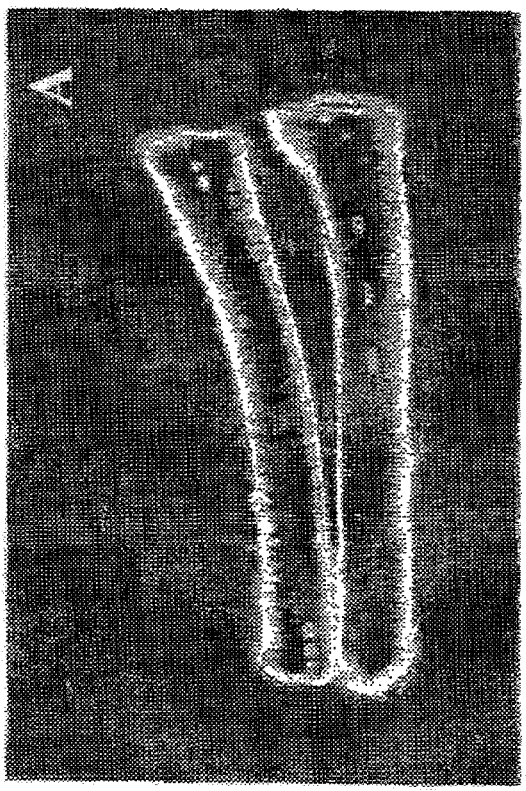
Figure 11C:
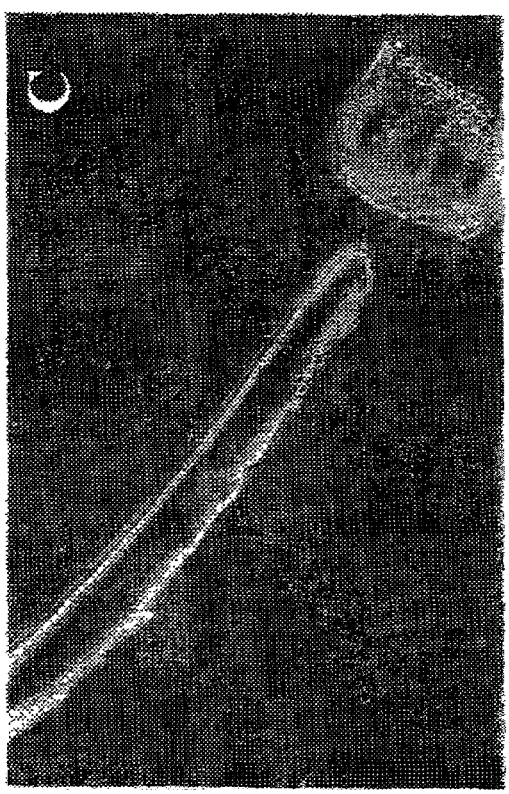

FIG. 10: Identification of satellite cells on muscle fibers. A) Fixed muscle fiber (phase contrast×520; bar=50 μm) B) Bis-benzimide stain under UV light showing both myonuclei and satellite cell nuclei. C)C-met immunostaining of the muscle fiber distinguishes between satellite cells and myonuclei by staining the cytoplasm of satellite cells, but not nuclei of satellite cells or myonuclei within the fiber or fiber sarcoplasm. Negative control fibers lacking primary antibody did not stain satellite cells.

FIG. 11: Staining of fiber nuclei using ethidium bromide. A) 2 fibers fixed using methanol immediately after plating and coverslipping (phase contrast×285; bar=50 μm). Membrane blebs appear on and close to the fiber due to hypotonic conditions during incubation in this experiment. B) The nuclei in these fixed fibers were stained immediately after the addition of EtBr (2.5 μg/ml; positive control). C) Unfixed live and hypercontracted fibers. (phase contrast×260; bar= 50 μm) D) Nuclei in the hypercontracted fiber stained red immediately after EtBr was added to the dish, but fiber nuclei on the live fiber did not stain, even after this 30 minute incubation.

FIG. 12: Addition of Marcaine+EtBr to fibers. A) Unfixed live fiber (phase contrast×260; bar=50 μm) B) Live fiber 90 seconds after the addition of Marcaine and EtBr. The fiber has yet to hypercontract but the nuclei are stained positive, indicating that Marcaine allows EtBr to permeate into the fiber. C) Unfixed live fiber. D) Same fiber as C four minutes after Marcaine+EtBr were added to the dish. The fiber has hypercontracted. E) Nuclei in the hypercontracted fiber also stained red. Note that processes bulging from fiber surfaces in D all contain a nucleus, but that satellite cell nuclei cannot be distinguished from myonuclei by this method.

Figure 13A:
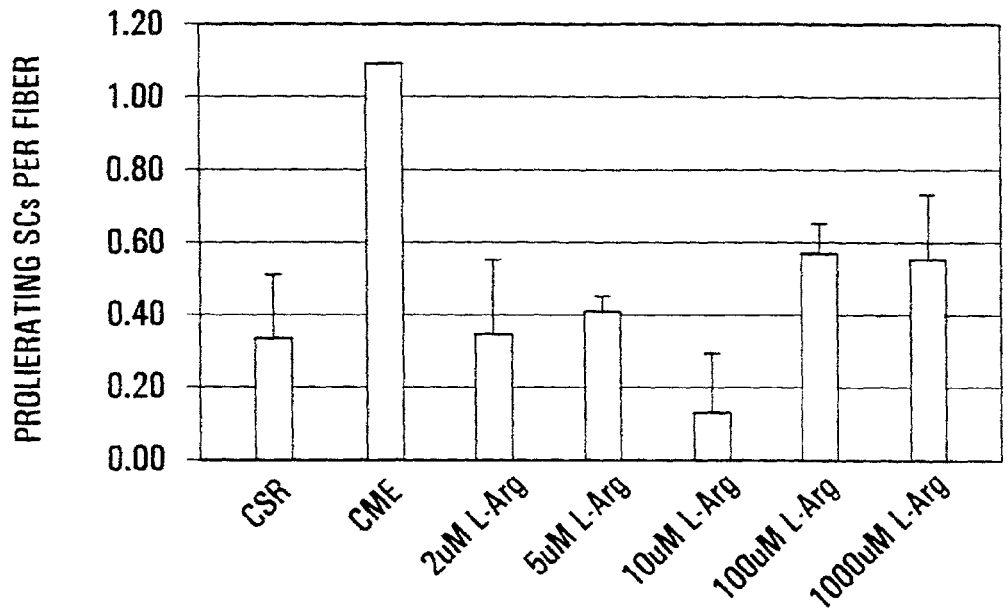
Figure 13B:
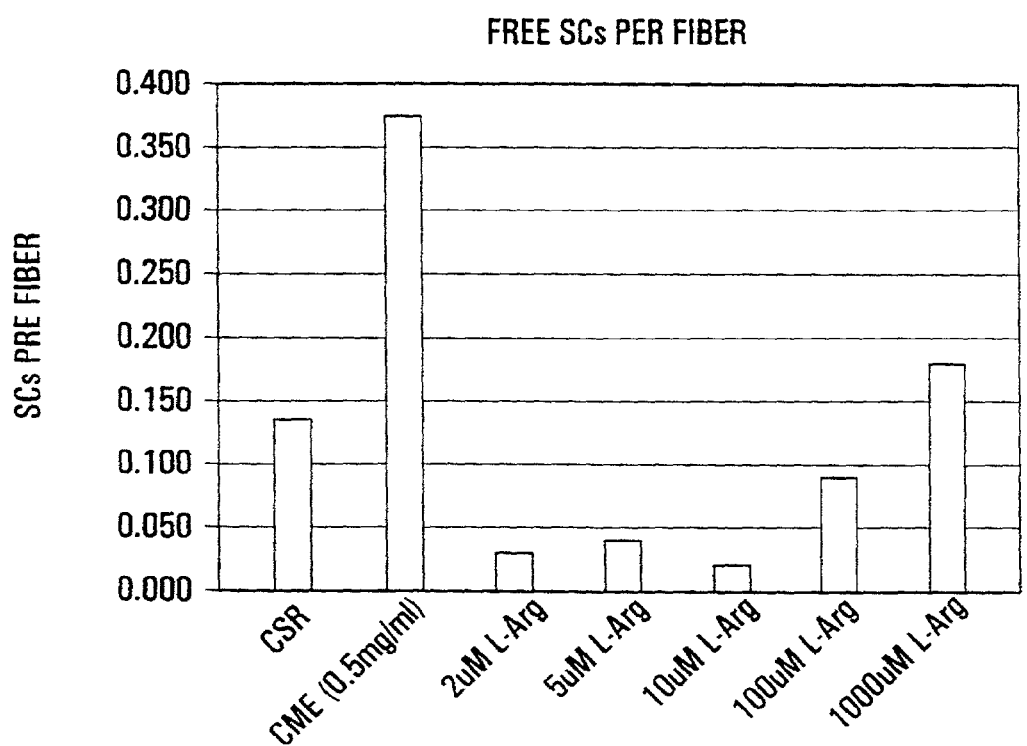

FIG. 13: Single fiber experiments to test the effects of L-Arginine at various concentrations on: A) proliferating satellite cells per fiber, and B) free satellite cells per fiber in culture after 48 hr. CSR is serum replacement medium; CME is crushed muscle extract.

Figure 14:
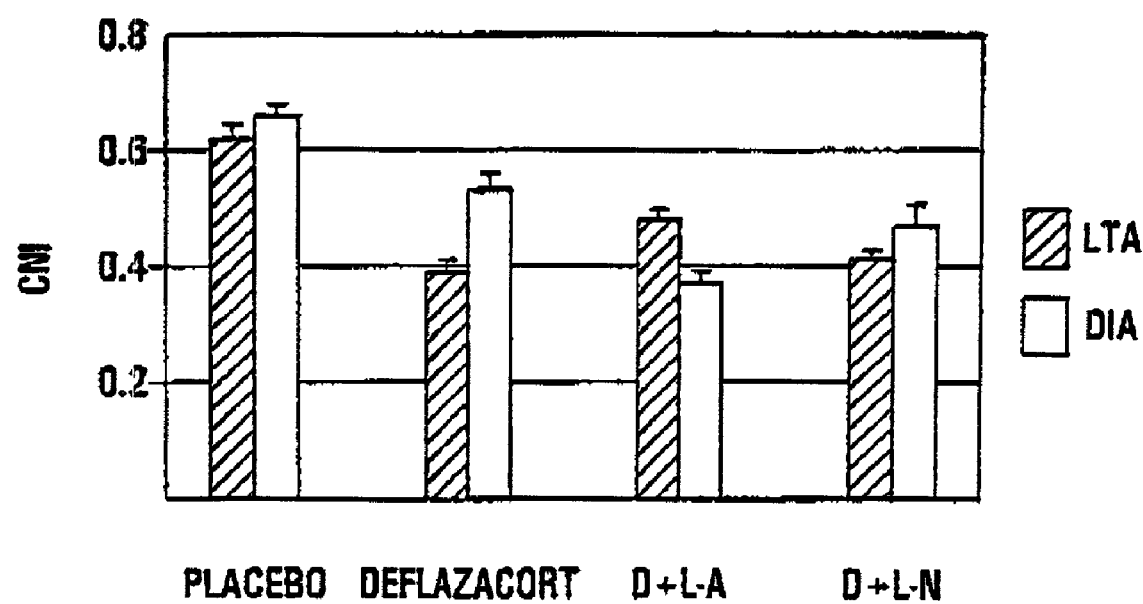

FIG. 14: Manipulation of NO augments deflazacort effects. CNI: central nucleaction index; LTA: left tibialis anterior muscle; DIA: diaphragm.

DETAILED DESCRIPTION OF THE INVENTION

I. GENERAL

As used herein, the term "myogenic precursor cells" refers to cells capable of myogenesis, or the process of proliferation and differentiation into new and functional muscle when present in a morphogenically permissive environment. Myogenic precursor cells are variously referred to as "myoblasts," "muscle stem cells" or "satellite cells".

The present invention derives from, but is not limited to, the unexpected result that NO mediates satellite cell activation. Without being bound by theory, a model is presented in FIG. 8 which broadens the field of NO signalling in muscle (reviewed by Grozdanovic and Baumgarten (1999) Histol. Histopathol. 14: 243–256) and hypothesizes that NO release mediates satellite cell activation by being responsive to shear. In this model, normal cyclic loading of muscle produces pulsatile NO release (Tidball et al. (1998) Am. J. Physiol. 275: C260–C266) by rapid diffusion of NO down its concentration gradient, and maintains satellite cell quiescence. By contrast a large release of NO would move as a wave front across the narrow clefts between a fiber and its satellite cells, the following lapse in pulsatile or bolus NO release would constitute the second phase of a powerful primary signal, a "nitric oxide transient" in physiological terms. Teleologically, the external lamina wrapping fibers may provide the potential for satellite cells to respond to shear between the sarcolemma and lamina. Satellite cells hug fibers across an even 15 nm cleft without obvious junctional complexes, and they associate closely with external lamina (Bischoff (1990) J. Cell Biol. 111: 201–207; Schultz and McCormick (1994) Rev. Physiol. Biochem. Pharmacol. 123: 213–257). Thus satellite cells have ideal topography to detect a rapid peak of NO release from underlying fibers after shear and also to be kept quiescent by normally continuous small pulses of NO from the fiber. The speed of the NO-mediated signal for activation suggests that an initiating event such as mechanical shear forces acts on constitutive nitric oxide synthase (NOS-I), since the response time is too short to induce expression or increase activity (McCall et al. (1991) Eur. J. Immunol. 21:2523–2527; Rubinstein et al. (1998) J. Clin. Invest. 101:1325–1333). A large release of NO is thus the primary signal that mediates or directly signals satellite cell activation. Other secondary signals such as HGF/SG or other factors are then needed to maintain or complete activation. Such secondary signals or the pathways that induce/initiate the secondary signals may become activated themselves, and circulate from the initiating site to initiate activation of satellite cells located outside the damaged muscle. Without the NO-mediated signal, however, normal fibers would repress activation and their satellite cells would return to quiescence. By contrast, satellite cells in damaged muscles, having received the secondary circulating signal or signals in addition to the primary signal, would complete the activation sequence. Experimental evidence consistent with the above model is presented in detail in Examples 1 to 8 and Example 10.

Shear produced by layers that shift laterally against each other would be strong during segmental retraction within the external lamina. Compared to myoblast transfer and according to the model, intramuscular injection of muscle fibers and their adherent satellite cells is a form of shear which could maximize shear-induced satellite cell activation and supply crushed muscle extract containing (HGF) directly to the site of fiber implantation. This hypothesis therefore can integrate diverse topics of NO physiology, mechanical force transduction, cell signalling, dystrophy and repair. In that context, NO manipulation of satellite cell activation can dramatically improve muscle repair using fiber injection compared to that achieved to date using myoblast transfer therapies. Transient precursor proliferation in denervation, and persistent proliferation after trauma or segmental disease can be explained by applying the idea of NO-mediated, shear-induced satellite cell activation upon total synchronized nerve and fiber depolarization and then loss of membrane potential. Interestingly, intense m-cadherin+satellite cells in muscle spindles suggest high shear responsiveness may accompany the spindle function as a length-tension receptor. There is also a potential for NO interaction with m-cadherin in mediating loss of adhesion during activation and the ratio of RTA/LTA less than one at 0 min during NOS inhibition or decreased NOS-I expression (FIG. 2) suggests that reduced NO may mediate an increase in satellite cell adhesion to the fiber-lamina complex.

Until now, satellite cell activation was defined structurally as cytoplasmic and organelle hypertrophy and dynamically as recruitment to cycle. The close adherence of satellite cells to parent fibers must decrease during activation for satellite cells to move through the external lamina to form new fibers. Therefore the loss-of-adhesion feature was used as a simple index of activation. The ability to isolate myogenic cells after brief standard digestion was a conservative estimate of available satellite cells and not an estimate of total myogenic cells. (Additional myogenic cells are found in the material collected on the Nitex filter during cell isolations). NO is known to modulate leukocyte and platelet adhesion (Kubes et al. (1991) Proc. Natl. Acad. Sci. USA 88: 4651–4655; de Graaf et al. (1992) Circulation 85: 2284–2290) and m-cadherin mediates muscle precursor adhesion to fibers. So it is also possible that changes in adhesion and m-cadherin in repair (Moore and Walsh (1993) Development 110: 1409–1420; Irintchev et al. (1994) Dev. Dynamics 199: 326–337) may be affected by NO. Specific manipulation of satellite cell activation via changes in NOS-1$\mu$ activity or shear, rather than giving systemic alkali dietary supplements to stimulate bone formation and indirectly stimulate muscle fibers (Landauer and Burke (1998) Aviat. Space Environ. Med. 69: 699–702) could directly prevent muscle atrophy in microgravity.

Accordingly, one aspect of the present invention provides use of NO, an NO donor, an inhibitor of NO activity or a regulator of NO production to increase activation of skeletal muscle precursor cells, thereby improving muscle regeneration and/or repair. Localized, in situ or systemic activation is further provided. The present invention further provides use of NO, an NO donor, an inhibitor of NO activity or a regulator of NO production to amplify populations of muscle cells in culture. In a specific embodiment, alteration of NO production is effected via changing NOS activity.

The present invention also has applications in the treatment of muscle dystrophic or degenerative disorders. One such disorder is Duchenne muscular dystrophy (DMD), an X-linked recessive disorder characterized by progressive and lethal muscle weakness. The absence of the cytoskeletal protein dystrophin, and dystrophin-associated glycoproteins which are normally complexed with laminin across the sarcolemma, are seen in DMD and in its genetic homologue the mdx mouse (Matsumura, Campbell (1994) Muscle Nerve 17: 2–15). The deficiencies essentially weaken the fiber sarcolemma, increasing its susceptibility to contraction-induced fiber damage (Petrof et al. (1993) Proc. Natl. Acad. Sci. USA 90: 3710–3714), which initiates segmental (Anderson et al. (1987) Anat. Rec. 219: 243–257) fiber necrosis and focal inflammation. Sequential regeneration processes result, which are either effective in nearly restoring muscle funtion, as in the mdx limb muscles, (Anderson et al. (1987) Anat. Rec. 219: 243–257; Anderson et al (1988) J Muscle Res. Cell Motil. 9: 499–515; Coulton et al. (1988) Neuropathol. Appl. Neurobiol. 14: 299–314; Dangain et al. (1984) Muscle Nerve 7: 700–704) or less successful, as in mdx diaphragm and in DMD (Dupont-Versteegden et al (1992) Muscle Nerve 15: 1105–1110; Sklar RM (1991) J. Neurol. Sci. 101: 73–81).

According to the present invention, in relation to muscle dystrophy, cytoplasmic NOS-I in mdx muscle would act as a diffuse areal source of NO rather than the nearby linear source, subjacent and parallel to satellite cells found in normal muscle. The normally steep NO gradient across the cleft between fiber and satellite cell would therefore be more shallow, diffuse more slowly, and the small NO transient would show attenuated responsiveness to shear forces. If normal pulsatile NO acts to maintain quiescence, a smaller gradient from pulsatile NO of cytoplasmic origin in dystrophy, could release mdx satellite cells from what is normally full quiescence, and account for the greater proliferative activity and larger satellite cells in mdx muscle and primary cultures (McIntosh, et al. (1995) Biochem. Cell Biol. 73: 181–190; Permitsky, A. N., and Anderson, J. E. (1996) Exp. Cell Res. 22: 214–222; Moor, A. N. et al. (2000) Microsc. Res. Tech). Rapid repair by mdx muscle is consistent with the notion that mdx satellite cells are partly activated or on 'stand-by.' As well, it would follow that acute injury would not necessarily augment immediate activation for mdx and NOS-I knockout mice, as reported here in cell yield studies. By that reasoning, repair after imposed injury in the NOS-I X mdx double mutant should be less effective and/or delayed compared to mdx muscle repair. As well, dystrophy in that double mutant may be more severe than in mdx mice if it were assessed in mice younger than 12 months, before the index of repair (central nucleation) has reached its theoretical plateau. Since human fibers are bigger than mdx fibers, cytoplasmic NOS-I in human fibers would serve as an even smaller non-linear NO source than in mdx muscle. The resulting very shallow gradient or physiological NO transient across satellite cells could partly account for the severity of Duchenne dystrophy, almost as if the standby activation (like a "hair trigger") contributes to overly enthusiastic successive repair events and resulting in premature senescence (Decary et al. (1996) Human Gene Therapy 7: 1347–1350; Decary et al. (1997) Human Gene Therapy 8: 1429–1438; Webster C and Blau H, (1990) Somatic Cell Molec Genet 16: 557–565; but see also Bockhold K J et al. (1998) Muscle Nerve 21: 173–183). It is now clear that satellite cell activation needs to be considered separately from dystrophy.

Accordingly, another aspect of the present invention provides use of an inhibitor of NO production to decrease activation of skeletal muscle precursor cells, thereby limiting proliferation of skeletal muscle precursor cells. Localized, in situ or systemic decrease is further provided. In a specific embodiment, inhibition of NO production is effected by changing NOS activity.

It is known that in DMD patients, deflazacort improves muscle strength (Markham A, and Bryson H M, (1995) Drug Eval. 50: 317–333; Reitter B. (1995) Brian Dev. 17 (suppl): 39–43) and delays loss of ambulation (Angelini C, Pegeraro E, Turella E, Intino M T, Pini A, and Costa C. (1994) Muscle Nerve. 17: 386–391) while increasing muscle mitochondria and oxidative metabolism (Khan MA. (1993) J. Neurol. Sci. 120: 8–14). Importantly it prevents loss of bone trabeculae in comparison to prednisone (LoCascio V, Ballanti P, Milani S, Bertoldo F, LoCascio C, Zanolin E M, and Bonucci E. (1998) Calci. Tissue Int. 62: 199–204). Deflazacort effects on muscular dystrophy and muscle repair were examined in mdx mice, genetically homologous to DMD. Early treatment reduced tissue inflammation and increased fiber size in limb and diaphragm muscles (Anderson J E, McIntosh L M, and Poettcker R. (1996) Muscle Nerve. 19: 1576–1585). In regenerating muscles (with repair synchronized by crush injury), the myoblast proliferation and fusion into new fibers were higher after deflazacort. Deflazacort also increased strength and laminin expression, advanced new fiber differentiation (marked by MM CK expression, Bischoff and Heintz, 1994) and increased the numbers of c-met+satellite cells in regenerating muscle.

The present invention demonstrates that manipulating NO-mediated activation can augment the beneficial effects of a steroid such as deflazacort (see Example 11). In a specific embodiment, manipulation is effected by changing NOS activity.

Accordingly, another aspect of the present invention provides use of NO, an NO donor, an inhibitor of NO activity or a regulator of NO production to modulate the effects of a steroid hormone on skeletal muscle. Localized, in situ or systemic modulation is further provided. As a specific embodiment, the steroid hormone is deflazacort. As a further specific embodiment, the treatment is most effectively achieved by application in situ of a compound for altering NO-mediated activation, or by delivering such a compound to specific tissue sites, since systemic treatment can affect to a different extent one muscle type or one phenotype of dystrophy, compared to another muscle phenotype.

Where a localized manipulation of NO level is to be achieved (e.g. localization to a particular skeletal muscle or group of skeletal muscles, or to skeletal muscle of a specific organ), the composition containing NO, an NO donor, an inhibitor of NO activity, a regulator of NO production or an inhibitor of NO production may include some component that is specific to the target tissue and organ, e.g. a muscle-targeting component.

The present invention further describes a technique for using isolated muscle fibers to monitor satellite cell activation and thereby identifying compounds that promote or decrease activation. This technique allows tracking of individual satellite cells, as well as populations of cells, under closely monitored conditions. The separation of satellite cells from fibroblasts and inflammatory cells is important since the latter cells are sources of cytokines and growth factors which also have a role in repair, and whose effects may interfere with effects of the compound to be identified.

Use of isolated muscle fibers to characterize activation involves (1) unambiguous distinction between precursor cells and myonuclei; and (2) determination of the time of fiber death under known conditions. Accordingly, one aspect of the present invention provides methods for monitoring the state of precursor cell activation and for determining whether a test compound effects activation. In one embodiment, the method of the invention is used to determine that the precursor cells are quiescent, i.e. in completely intact fibers without stimulus. In another embodiment, the method of the invention is used to determine that the precursor cells are in a state of activation which is independent of shear or hypercontraction. Accordingly, in another embodiment, the present method is used to determine whether a test compound affects hypercontraction-independent activation of the precursor cells. In another embodiment, the method of the invention is used to determine that the precursor cells are in a state of activation which is effected by shear-induced hypercontraction of the fiber. Accordingly, in another embodiment, the present method is used to determine whether a test compound affects activation which is effected by shear produced by hypercontraction of the fiber. Any compound of interest can be used as the test compound in this method.

In one embodiment, the method of the invention for monitoring the state of precursor cell activation and for determining whether a test compound effects or affects activation is as follows:

A. Fiber Isolation:

Fibers are isolated from muscles using a combination of fine dissection, enzyme digestion and physical disruption of a muscle cleaned of connective tissues, and are then plated on culture dishes coated in collagen (Vitrogen$^{RT}$ according to Yablonka-Reuveni Z and Rivera A. (1994) Dev Biol. 164: 588–603; Partridge TA (1997) Tissue Culture of skeletal muscle. From Methods in Molecular Biology, volume 75: 131–144, Humana Press, 1997). In one embodiment, the fibers may be isolated as detailed in Example 10. At least 16 dishes of fibers from a single experiment should be plated for culture.

B. Determination of Basal Activation Level (Control):

In one set of culture dishes, satellite cell-containing fibers in controlled serum replacement medium (non-stimulating basal medium) are incubated, typically for 30 minutes, then fixed in methanol/acetic acid and dried. The non-specific sites are blocked, typically in a 24 hr incubation, prior to immunostaining to identify muscle precursor satellite cells (according to published methods to identify c-met receptor in satellite cells or bcl-2 or CD-34 (also called Neural Cell Adhesion Molecule, N-CAM) in muscle stem cells), with and without counterstaining for m-cadherin, depending on the particular deficiency and nature of fibers.

The extent of proliferation activity by satellite cell nuclei can be examined using immunostaining procedures to localize Proliferating Cell Nuclear Antigen (PCNA) (Johnson and Allen, (1995) Exp. Cell Res.) or other molecules or epitopes which identify cell nuclei that are engaged in proliferation or DNA synthesis. Satellite cells can then be identified by microscopy using phase contrast optics and c-met or bcl-2, and the proliferation status assessed by the proportionate staining for PCNA in those cells. This proportion (either on a whole cell basis, or relative frequency distribution of the staining intensity in the population of nuclei examined in the satellite cells of a dish), serves as the basal level of activation, and is required for comparison between test situations (quality control) and serves as the negative control for the conditions in 3 and 4 below. This basal level of activation must be low, however, in comparison to either "test A" or "test B" levels of activation (below), in order for the test to be informative and meaningful.

C. Determination of the True Basal Activation Level:

In another set of culture dishes, satellite cell-containing fibers in controlled serum replacement medium containing a DNA intercalating substance (e.g. ethidium bromide or propidium iodide or other substances that intercalate into DNA of dead cells) are incubated typically for 30 min. This incubation is used to determine whether the sarcolemmal membranes of the fibers are intact (in which case the myonuclei inside such fibers will be non-fluorescent) or breached/porous (in which case the myonuclei, if ethidium bromide is used, will fluoresce red with the ethidium bromide having intercalated into the DNA). In either case, nuclei within satellite cells will be non-fluorescent, since their membranes, which are not typically thought to be subject to damage, exclude the DNA intercalator. Counter staining with antibodies specific to muscle precursor cells (e.g. c-met, bcl-2 or CD-34/N-CAM) serves to confirm the identity of satellite cells, alone or in combination with each other and with immunostaining for m-cadherin, as explained above. Proliferation status can be assessed by staining for PCNA or assaying other markers of proliferation as described above. Determination of fiber integrity and confirmation of proliferation status substantiate that the "basal level of activation" as determined above is the true basal level of activation.

D. Determination of Fiber Hypercontraction-Independent Activation (Test A):

Under certain conditions of fiber damage or stimuli, satellite precursor cells are activated without fiber hypercontraction (e.g. toxicity or stimulation by factors or proteins). Such conditions or stimuli, including treatment with a test compound, are determined by comparing the "true basal level of activation" in fiber cultures in the absence of the test compound or test condition, with the level of activation observed after treatment with the test compound or test condition. The difference in the levels of activation determines the level of hypercontraction-independent activation (Test A).

The compound or condition which produces activation of satellite precursor cells ultimately results in new DNA synthesis within the satellite cell nuclei. Thus, incorporation of bromodeoxyuridine (BrdU) or other non-isotopic or isotopic nucleotide analogues into DNA of satellite cell nuclei can be used to monitor the level of proliferation. After a pre-set labelling period (typically after 24–48 hours), the proportionate labelling of satellite cell nuclei (identified as above by the localization of marker proteins and the structural juxtaposition to fibers with or without the presence of m-cadherin), is determined by immunostaining or exposure of emulsion after fiber fixation and appropriate staining/photo-identification as required. In Test A, the difference between the proportionate labelling with the test compound or condition, and the proportionate labelling without the test compound or condition reflects the level of activation independent of fiber hypercontraction (shear) induced by the compound or condition.

E. Determination of Fiber Hypercontraction-Mediated Activation (Test B):

Under certain conditions or stimuli, satellite precursor cell activation is mediated by fiber hypercontraction or shear, either in addition to or distinct from activation mediated via hypercontraction-independent mechanisms (evidenced by "test A" above).

The compound or condition which produces activation of satellite precursor cells ultimately results in new DNA synthesis within the satellite cell nuclei. Accordingly, incorporation of bromodeoxyuridine (BrdU) or other non-isotopic or isotopic nucleotide analogues into DNA of satellite cell nuclei can be used to monitor the level of proliferation as described above in connection with Test A.

To determine the level of shear/hypercontraction mediated activation (Test B), fibers in another set of culture dishes are incubated in a medium containing a myotoxin (e.g. Marcaine) plus a DNA intercalator (e.g. ethidium bromide) until the myotoxin produces fiber membrane damage sufficient to allow fiber hypercontraction and fluorescence of the myonuclei. Satellite cells are resistant to the myotoxic effects of Marcaine and therefore their nuclei do not typically fluoresce.

Once fiber hypercontraction and fluorescent myonuclei are observed by visual inspection using a microscope, the medium containing Marcaine and the DNA intercalator is removed and replaced with a controlled serum replacement medium with and without the test compound. After a pre-set time (typically 24–48 hours, and importantly the same as established in section D above), the proportionate labelling of satellite cell nuclei (identified as above by the localization of marker proteins and the structural juxtaposition to fibers with or without the presence of m-cadherin) is determined by immunostaining or exposure of emulsion after fiber fixation and appropriate staining/photo-identification as required. In Test B, the difference between the proportionate labelling with the test compound, and the proportionate labelling without the test compound reflects effect of the test compound on the level of shear or hypercontraction-dependent activation. The proportionate labelling without the test compound reflects the basal level of shear or hypercontraction-dependent activation which characterizes the innate responsiveness of the fibers.

According to the above-described embodiment of the method, there are therefore four identifiable levels of activation which reflect the innate and the responsive activation states of skeletal muscle precursor cells.

In terms of innate states of activation, the states denoted as "true basal" and "basal shear or hypercontraction-dependent" levels together characterize and determine the activation state of precursor cells in a muscle fiber, as an innate feature of fiber character. Quantifying these levels is important for quality control, i.e. establishing inter-test variability.

In terms of responsive states of activation, the activation observed under conditions of "Test A" results from application of the test compound and is independent of shear or hypercontraction. The activation observed under conditions of "Test B" results from application of the test compound and is dependent on shear or hypercontraction. These two types of activation together characterize and determine the activation state of precursor cells in a muscle fiber treated with the test compound in single fiber culture.

A particular compound may have effects on satellite cell activation via mechanisms and pathways dependent and/or independent of fiber shear or hypercontraction. Either (or both) mechanisms are targets of treatment and are likely affected by pathophysiologic mechanisms of diseases which directly or indirectly involve skeletal muscle.

II. NITRIC OXIDE AND DONORS OF NITRIC OXIDE:

Nitric oxide (NO) is a major freely diffusible endogenous mediator involved in diverse developmental and physiological processes (Annu. Rev. Biochem. (1994) 63: 175–195). In addition to controlling diverse cellular processes, NO also participates in certain pathophysiological conditions. In skeletal muscle NO has been shown to depress the muscle contractile function (Nature (1994) 372: 546–548). In the brain, nitric oxide plays important physiological role in neurotransmission and synaptic modulation. In primary cortical cultures, NO mediates glutamate neurotoxicity (Proc. Nat. Acad. Sci. (1991) 88: 6368–6371). The effect of NO on skeletal muscle has been extensively reviewed (e.g. Kroncke et al. (1997) Nitric Oxide Biology and Chemistry 1(2): 107–120; Reid, M. (1998) Acta Physiol Scand. 162: 401–409).

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide (NO•) and charged nitric oxide species, particularly including nitrosonium ion (NO+) and nitroxyl ion (NO−). The nitric oxide releasing, delivering, or transferring compounds include any and all such compounds which provide nitric oxide to its intended site of action in a form active for their intended purpose. As used here, the term "NO" donor encompasses any of such nitric oxide releasing, delivering or transferring compounds. NO donors include organic nitrates (e.g., glyceryl trinitrate (GTN)), organic nitrites (e.g., iso amyl nitrite), inorganic nitroso compounds (e.g., sodium nitroprusside (SNP)), sydnonimines (e.g., molsidomine (SIN-1)), furoxans and S-nitrosothiols (RSNO) (e.g., S-nitrosoglutathione, (GSNO)). It is understood that the appropriate choice of NO donor may facilitate its transport, prolong its life in the target tissues, target its delivery to specific sites (e.g. skeletal muscle) and mitigate its potential cytotoxicity.

One group of such NO adducts is the S-nitrosothiols, which are compounds that include at least one —S—NO group. Such compounds include S-nitroso-polypeptides (the term "polypeptide" is contemplated to include proteins and also polyamino acids that do not possess an ascertained biological function, and derivatives thereof), S-nitrosylated amino acids (including natural and synthetic amino acids and their stereoisomers and racemic mixtures and derivatives thereof), nitrosated sugars, S-nitrosated oligonucleotides and derivatives thereof, S-nitrosated hydrocarbons where the hydrocarbon can be a branched or unbranched, saturated or unsaturated aliphatic hydrocarbon, or an aromatic hydrocarbon, S-nitroso hydrocarbons having one or more substituent groups in addition to the S-nitroso group, and heterocyclic compounds. S-nitrosothiols and the methods for preparing them are described in U.S. Pat. No. 5,380,758, filed Sep. 14, 1992; Oae et al. (1983) Org. Prep. Proc. Int. 15(3): 165–198; Loscalzo et al. (1989) J. Pharmacol. Exp. Ther. 249(3): 726–729 and Kowaluk et al. (1990) J. Pharmacol. Exp. Ther. 256: 1256–1264.

III INHIBITORS OF NO ACTIVITY;

Inhibitors of NO activity (NO inhibitors) contemplated for use in the invention are compounds which chemically reacts with NO, binds to NO, or otherwise interacting with NO in such a way that the effective concentration of NO is reduced. Such inhibitors of NO activity include, but are not limited to, NO scavengers such as membrane impermeable NO scavengers including MGD-FE (N-methyl-D-glucamine dithiocarbamate/ferrous sulfate mixture), carboxy PTIO (2-(4-carboxyphenyl) 4,4,5,5-tetra methylimidazoline-1-oxyl 3-oxide), calcium chelator BAPTA/AM, S-nitroso-N-acetyl-penicillamine (SNAP), 3-morpholino sydnonimine (SIN-1), diethyldithiocarbamate, melatonin and its precursors, superoxide dismutase, glutathione peroxidase, glutathione reductase, dimethyl sufoxide.

IV. REGULATORS OF NITRIC OXIDE PRODUCTION:

As an alternative to NO and NO donors, regulators of NO production may be used in the practice of the present invention. In a preferred embodiment, a regulator of NO production is the NOS I$\mu$ enzyme.

Because NO is a short-lived free radical, regulation of signaling occurs in vivo largely at the level of NO biosynthesis. Three mammalian nitric oxide synthase (NOS) genes have been identified; each forms NO from the guanidine nitrogen of L-arginine in a unique cytochrome P-450-type reaction that consumes reduced nicotinamide adenine dinucleotide phosphate. These three NOSs are endothelial (eNOS), neuronal NOS(nNOS) and inducible NOS (iNOS) also termed respectively NOS-III, NOS-I, and NOS-II. The nNOS and eNOS enzymes are discretely expressed in specific tissues and rapidly transduce signaling events in a calcium-dependent manner. eNOS activity accounts for endothelium-dependent blood vessel relaxation, while nNOS occurs discretely in a variety of cell types, including neurons, epithelial cells, mesangial cells, and skeletal muscle cells. Inducible iNOS is a calcium-independent form of NOS expressed at highest levels in immunologically activated cells.

NO is produced constitutively at high levels in skeletal muscle by an isoform of neuronal nitric oxide synthase, NOS-I$\mu$. NOS-I$\mu$ is linked via $\alpha$1-syntrophin to the dystroglycan complex especially in fast-twitch fibers. In DMD and mdx dystrophy NOS-I$\mu$ is expressed at low levels and displaced to the cytoplasm (Brenman J E, Chao D S, Xia H, Aldape K, and Bredt D S. (1995) Cell 82: 743–752; Grozdanovic Z, and Baumgarten H G. (1999) Histol. Histopathol. 14: 243–256). However, free radical NO injury in the cytosol as a mechanism of severe dystrophy was ruled out by studies in md X NOS knockout mutant mice (Crosbie R H, Straub V, Yun HY, Lee J C, Rafael J A, Chamberlain J S, Dawson V L, Dawson T M, and Campbell K P. (1998) Hum. Mol. Genet. 7: 823–829; Chao D S, Gorospe R M, Brenman J E, Rafael J A, Peters M F, Froehner S C, Hoffman E P, Chamberlain J S, and Bredt D S. (1996) J. Exp. Med. 184: 609 618). NOS activity converts the NO donor, L-arginine to NO and L-citrulline. Critical controls on NO action involve tissue biophysics and important mechanical forces like shear, produced by pressure in a structure when its layers shift laterally across one another (Busse R, and Fleming I. (1998) J. Vasc. Res. 35: 73–84), such as hypercontraction of a muscle fiber. Gradients and contours of NO concentration signal nearby cells (Lancaster JR. (1997) Nitric Oxide: Biol. Chem. 1: 18–30).

Regulators which increase NO production include, but are not limited to, the NOS enzyme or substances which result in an increase in NOS activity (e.g. sodium nitroprusside or SNP, SNAP, NOC 5, NOC 7 (1-hydroxy-2-oxo-3-[(methylamino)propyl)]-3-methyl-1-triazine), guanidinosuccinic acid, SIN-1, SIN-10), or an increase in NOS gene expression. Specifically, the scope of the present invention encompasses the use of gene therapy, pharmacologic and immunologic means to achieve systemic or local delivery of a product to target, produce and/or substantially result in increased local satellite cell activation (e.g. for muscle atrophy, muscle growth) via, e.g.

over-expression of the enhancer region of the gene encoding NOS-I$\mu$;

over-expression of a regulatory intronic region of the gene encoding NOS-I$\mu$;

over-expression of the promoter region of the gene encoding NOS-I$\mu$;

anti-sense oligonucleotides or transcriptional regulatory sequences which bind DNA and modulate expression of the NOS-I$\mu$ gene;

increasing production of NOS-I$\mu$ by satellite cells; manipulation of the 5' untranslated region upstream of the gene for NOS-I$\mu$;

S-nitrosomyoglobin (as an NO-donor);

increased binding or expression of proteins that bind NOS-I$\mu$;

(e.g. PDZ93 and PDZ95);

increasing the stabilization of NOS-I$\mu$ protein in the cytoskeleton structure in the absence of dystrophin (e.g. by synthetic linkage to a transmembrane protein like a calcium channel protein or to a costameric protein anchored between the sarcolemma and the myofilament (contractile) proteins).

Regulators which decrease NO production include inhibitors of the NOS enzyme. Suitable nitric oxide synthase inhibitors which may be employed include, but are not limited to, arginine-based analogues such as NG$^G$-monomethyl-L-arginine (NMA), nitro-arginine, N-nitro-L-arginine methyl ester (L-NAME), N-amino-L-arginine, and N-methyl-L-arginine; flavoprotein binders such as diphenylene iodonium and related iodonium derivatives, ornithine and ornithine derivatives such as N-iminoethyl-L-ornithine; redox dyes such as methylene blue; calmodulin binders such as trifluoropiperazine and calcinarin; heme binders; and depleters of biopterin such as methotrexate.

The scope of the present invention encompasses the use of gene therapy, pharmacologic and immunologic means to achieve decreased local satellite cell activation (e.g. in muscle that is excessively activated as in genetic disease like DMD, and the diaphragm of mdx mice) via, e.g.

anti-sense oligonucleotides and transcriptional regulatory sequences which bind polynucleotides encoding NOS-Iμ and inhibiting its production;

decreasing production of NOS-Iμ by satellite cells;

antibodies which bind and inhibit NOS activity.

Increased systemic satellite cell activation (e.g. for widespread growth of muscle as in agriculture, chronic wasting diseases and athletic interests may be achieved via, e.g.

analogues or homologues of NOS-Iμ, transfections of replication-defective adenoviral or retroviral vectors with a sequence that would substitute for NOS-Iμ activity and bind to the cytoskeleton inside skeletal muscle fibers without affecting the vasculature or neuronal NOS or inducible NOS expression or activity;

activation of NOS-Iμ protein or its analogues or homologues that could substitute for NOS-Iμ activity and bind to the cytoskeleton inside fibers without affecting vasculature or neuronal NOS, or inducible NOS expression or activity;

use of analogues or homologues of NOS which are active inside muscle fibers;

increasing NOS-Iμ production by satellite cells;

regulatory sequences or compounds (endogenous or exogenous) that increase HGF binding with c-met in satellite cells, to promote the cascade of steps downstream from NO-mediated satellite cell activation.

Decreased systemic satellite cell activation may be desired in certain circumstances. For example, a temporary halt in activation may be desired where the activation is a negative consequence of drug treatment inducing wasting by loss of the satellite cell or stem cell population in a skeletal muscle. A permanent halt may be desired in muscle-derived tumours, genetically altered muscle myogenic cells used to treat diabetes, short stature (due to loss of GH), pancreatic insufficiency, osteoporosis, liver disease, genetic and metabolic neurotrophic abnormalities. Such decreased activation may be effected via:

blocking NOS-Iμ activity;

blocking transcription of the NOS gene or inhibiting the activators of NOS-Iμ protein activity;

absorbing compounds which give rise to NO from the region between the muscle fiber sarcolemma and the satellite cells (e.g. proteins in the m-cadherin cleft or analogues/homologues of m-cadherin that could be resistant to NO-induced loss of satellite cell adhesion);

blocking binding of HGF with c-met in the satellite cell (preventing downstream effects of NO-mediated activation);

blocking the transcription of NOS-Iμ in satellite cells.

V. FORMULATIONS AND DELIVERY METHODS:

A. Formulations:

The NO, NO donor, inhibitor of NO activity or regulator of NO production of the present invention may be provided to precursor muscle cells by any suitable means, preferably directly (e.g., in vitro by addition to culture medium, or locally by injection or topical administration at a treatment site) or systemically (e.g., parenterally or orally). Preferably, the NO, NO donor, inhibitor of NO activity or regulator of NO production comprises part of a physiologically acceptable solution so that in addition to delivery of the desired agent to the target cells, the solution does not otherwise adversely affect the cells or subject's electrolyte and/or volume balance.

For systemic administration, the NO, NO donor, inhibitor of NO activity or regulator of NO production of the present invention may be administered by any route which is compatible with the particular NO, NO donor, inhibitor of NO activity or regulator employed. Where the agent is to be provided parenterally, such as by intravenous, subcutaneous, intramuscular intraorbital, ophthalmic, intraventricular, intracranial, intracapsular, intraspinal, intracisternal, intraperitoneal, buccal, rectal, vaginal, intranasal or by aerosol administration, the agent preferably comprises part of an aqueous solution. In addition, administration may be by periodic injections of a bolus of the NO, NO donor, inhibitor of NO activity or regulator of NO production, or may be made more continuous by intravenous or intraperitoneal administration from a reservoir which is external (e.g., an i.v. bag) or internal (e.g., a bioerodable implant, or implanted NO-producing cells either singly or in colonies).

If desired, a given NO donor or regulator of NO production or other agent may be adapted to different situations by association with a suitable molecule. For example, association or genetic fusion of NOS to another protein may improve NOS binding to the sarcolemma and/or cycloskeleton to effect increased NOS activity inside fibers in close proximity to the sarcolemma, NO donors or regulators may also be made more soluble or dispersible in physiological solutions than the corresponding original form.

Formulations for local or topical administration to a tissue or skin surface may be prepared by dispersing the NO, NO donor, inhibitor of NO activity or regulator of NO production with an acceptable carrier such as a lotion, cream, ointment or soap. Particularly useful are carriers without NO scavenging or producing actions of their own, that are also capable of forming a film or layer over the skin or tissue to localize application and inhibit removal. For local or topical administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

The pharmaceutical compositions comprising NO or NO donors, as utilized in this invention can be administered by intranasal, oral, enteral, topical, vaginal, sublingual, rectal, intramuscular, intravenous, or subcutaneous means.

The compounds of this invention can be employed in combination with conventional excipients; i.e., pharmaceutically acceptable organic or inorganic carrier substances suitable for parenteral, enteral or intranasal application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxilliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable vehicles consist of solutions, preferably oily or aqueous solutions, as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc, or slow-release polymers or other compounds formulated with or without inherent complementary or tissue-specific physical intervention capabilities.

It will be appreciated that the actual preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guide lines. See as a general guideline, Remington's Pharmaceutical Science, lath Edition, Mack (Ed.), 1980.

According to the present invention, a "therapeutically effective amount" of a pharmaceutical composition is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane. Carriers for use within such formulations are bio-compatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

It is contemplated that nitrated or nitrosylated polymers may be used as a source of NO (WO98/05689). In an embodiment wherein nitrated or nitrosylated polymers is used, it is contemplated that the polymer is used to coat a device for implanting, or is used as a bolus for injecting, at a skeletal muscle site so that local delivery of NO is achieved.

The NO, NO donor, inhibitor of NO activity or regulator of NO production of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants, vehicles and vectors. The compounds can be administered orally, subcutaneously or parenterally including intravenous, intraarterial, intramuscular, intraperitoneal, ophthalmic, intraocular and intranasal administration as well as intrathecal and infusion techniques. Implants of the compounds are also useful. The animal being treated is a warm-blooded animal or cold-blooded animal (e.g. fish) and, in particular, but not exclusively, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein. Accordingly, the length of the treatment generally may be proportional to the length of the disease or process, and may further depend on the animal species, drug effectiveness and degree of effect required or recommended. The doses may be single doses or multiple doses over a period of several days, but single doses are preferred.

When administering the compound of the present invention parenterally, it will generally be formulated in a unit dosage injectable form (solution, suspension, emulsion) The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, gylcerol, propylene glycol, liquid polyethylene glycol, and the like), suitable mixtures thereof, and vegetable oils, often but not always without any inherent effect on NO generation or action.

Proper fluidity can be maintained, for example, by the use of a coating such as lecithin, by the maintenance of the required particle size in the case of dispersion and by the use of surfactants. Non-aqueous vehicles such as cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, availability (e.g. binding to heparan-sulfate proteoglycans at the myofiber extracellular matrix), sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. Retention of bioavailability in a tissue may be influenced by co-injection or co-administration with a stabilizing agent that would localize the invention as treatment to the fiber sarcoplasm or to the extracellular matrix as desired. According to the present invention, however, any vehicle, diluent, or additive used would have to be compatible with the compounds.

Sterile injectable solutions can be prepared by incorporating the compounds utilized in practising the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, vectors, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those described in: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 $\mu$g/kg to mg/kg per day.

B. Targeting:

The compounds provided herein also may be associated with molecules capable of targeting the NO, NO donor, inhibitor of NO activity or regulator of NO production to the desired tissue. For example, an antibody, antibody fragment, or other binding protein that interacts specifically with a surface molecule on cells of the desired tissue may be used. Molecules that identify muscle cells include molecular markers for muscle precursor cells (e.g. Bcl-2, disclosed in WO 98/44142; c-met receptor) or muscle fiber extracellular matrix and external sarcolemma HGF, M-cadherin, HGF-activating enzyme or collagen IV. An antibody may be generated against such a marker for targeting NO, NO donor, inhibitor of NO activity or regulator of NO production to the desired treatment site. Useful targeting molecules may be designed, for example, using the single chain binding site technology disclosed, for example, in U.S. Pat. No. 5,091,513. Targeting molecules can be covalently or non-covalently associated with the NO, NO donor, inhibitor of NO activity or regulator or NO production.

A targeting agent may be associated with NO, NO donor, inhibitor of NO activity or regulator of NO production to facilitate targeting to one or more specific tissues. As used herein, a "targeting agent," may be any substance (such as a compound or cell) that, when associated with regulator of NO production enhances the transport of regulator of NO production to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. An antibody targeting agent may be an intact (whole) molecule, a fragment thereof, or a functional equivalent thereof. Examples of antibody fragments are F(ab')$_2$, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a regulator of NO production to a target tissue, thereby increasing the local concentration of the regulator. Such targeting may be achieved using well known techniques, including retroviral and adenoviral infection.

Antibody Production: Antibodies may either monoclonal, polyclonal or recombinant. Conveniently, the antibodies may be prepared against the immunogen or portion thereof for example a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, Antibodies: A Laboratory Manual, Cold Spring Harbor Laboratory, Cold Spring Harbor, N.Y., 1988 and Borrebaeck, Antibody Engineering—A Practical Guide, W.H. Freeman and Co., 1992. Antibody fragments may also be prepared from the antibodies and include Fab, F(ab')$_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens to that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh 1995), messenger RNAs from antibody producing B-lymphocytes of animals, or hybridomas are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties, see Johnstone & Thorpe, Immunochemistry in Practice, Blackwell Scientific Publications, Oxford, 1982.) The binding of antibodies to a solid support substrate is also well known in the art. (See for a general discussion Harlow & Lane, Antibodies: A Laboratory Manual, Cold Spring Harbor Laboratory Publications, New York, 1988 and Borrebaeck, Antibody Engineering—A Practical Guide, W. H. Freeman and Co., 1992.) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, green or other-coloured fluorescent protein, rhodamine, tritium, $^{14}C$, thallium, gadolinium and iodination.

Targeted delivery of the NO, NO donor, inhibitor of NO activity or regulator of NO production of this invention may be achieved in conjunction with liposomes, which are artificial lipid vesicles. The first consideration in the preparation of targeted liposomes is the design of the (non-protein-coupled) liposome itself. The properties of liposomes are determined by two parameters: the method of liposome preparation and its lipid composition. The former parameter determines liposome size and number of lamellae, whereas the latter determines a number of properties such as surface charge, fluidity, and in vivo stability.

Several methods exist for the preparation of liposome (reviewed in Szoka Jr., F. and Papahadjopoulos, D. (1980) Ann. Rev. Biophys. Bioeng. 9: 467–508). Resuspension of a dried lipid film in an aqueous buffer results in the formation of large vesicles (diameter on the order of $\mu$m) containing a number of concentric bilayers, and are therefore referred to as multilamellar vesicles (MLVs). MLVs have a considerable capacity for aqueous contents, however, their multilamellarity (and consequent multicompartment nature) can hinder efficient release of their entire contents in the 'target' cell or tissue. Sonication of MLVs results in the formation of small unilamellar vesicles (SUVs) with a single bilayer and a diameter of approximately 25 nm. The small size of SUVs has been shown to confer decreased rates of clearance in vivo (Liu, D. and Huang, L. (1992) J. Lipsome Res. 2: 57–66); however, their correspondingly small inner volume limits the practical use of SUVs for the delivery of encapsulated aqueous materials. They may, however, be utilized in applications that do not involve encapsulation, such as the delivery of liposome-associated nucleic acids (via electrostatic interactions with cationic liposomal lipids), commonly referred to as 'lipofection' (Felgner et al. (1987) Proc. Natl. Acad. Sci. U.S.A. 84: 7413–7417; Leventis, R. and Silvius, J. R. (1990) Biochim. Biophys. Acta 1023: 124–132). Large unilamellar vesicles (LUVs) are the optimal type of liposome for many delivery applications, due their large capacity to encapsulate materials combined with easy access to such materials at their destination. Such properties of LUVs may simply be referred to as a high 'encapsulated volume/lipid' ratio; a quantity which is smaller in value for MLVs and SUVs, and which provides a simple index indicating the ability of liposomes to encapsulate soluble materials. Various methods for the preparation of LUVs exist, including dialysis from detergent/buffer mixtures (Weder, H. G. and Zumbuehl, O. (1984) in Liposome Technology (Gregoriadis G., ed.), Vol. 1, pp. 79–108, CRC Press, Boca Raton, Fla.), solvent evaporation from organic/aqueous mixtures (Szoka et al. (1980) Biochim. Biophys Acta 601: 559–571), freeze/thawing of Suvs (MacDonald, R. C. and MacDonald, R. I. (1993) in Liposome Technology (Gregoriadis G., ed.) Vol. 1. pp. 209–228, CRC Press, Boca Raton, Fla.) and high-pressure extrusion of MLVs (or larger LUVs) through filters of defined pore size (MacDonald et al., (1991) Biochim. Biophys. Acta. 1061: 297–303). Solutes dissolved in the aqueous buffers used in the above methods become encapsulated upon liposome formation, which is often followed by gel filtration chromatography or dialysis to remove the unencapsulated 'free' solute. Vesicle 'sizing' by pressure-filtration is also often performed to optimize the cellular uptake of liposomes, which has been shown to occur primarily by clathrin-mediated endocytosis (Straubinger et al. (1983) Cell 32: 1069–1079), and therefore liposome size must not exceed that of a cell-surface coated pit for efficient uptake to occur. Consistent with this mode of uptake, liposomes with a diameter in the range of 50–100 nm have been reported to exhibit efficient cellular uptake in vivo, which decreased as liposome diameter increased above 200 nm (Allen et al. (1991) Biochim. Biophys. Acta 1061: 56–64). Large liposomes (>200 nm dia.) are also cleared more rapidly in vivo, where a size-dependent tissue distribution has also been observed since liposomes with a diameter of greater than 300 nm preferentially accumulate in the spleen due to the filtration capability of this organ (Liu et al., (1991) Biochim. Biophys Acta 1066: 159–165). Therefore, liposomes of ca. 100 nm diameter are often chosen for most applications since they combine sufficient levels of contents encapsulation with optimal cellular uptake and decreased rates of clearance in vivo.

Various other pharmacologically important properties of liposomes are determined by their specific lipid composition, which is selected with particular attention to the optimization of liposomal delivery to cells or tissues in vivo or in vitro. Liposome surface charge has also been shown to have effects on liposome-cell interactions both in vitro (Batzri, S. and Korn, E. D. (1975) J. Cell Biol. 66: 621–634; Lee et al., (1992) Biochim. Biophys. Acta. 1103: 185–197) and in vivo (Juliano, R. L. and Stamp, D. (1975) Biochem. Biophys. Res. Commun. 63: 651–658). 'Fluidity' of the liposome membrane, determined by the chain-melting transition temperature ($T_m$) of the component phospholipids and the liposomal cholesterol content, can affect liposomal integrity (i.e., resistance to leakage of encapsulated contents; (Kirby et al. (1980) Biochem. J. 186: 591–598), in vivo clearance rates (Allen et al., (1989) Biochem. Biophys. Acta 981: 27–35), and the cellular uptake of liposomes (Allen et al., (1991) Biochem. Biophys. Acta 1061: 56–64).

'Targeting' of liposomes refers to the attachment of a ligand (e.g., protein) to the liposome surface, which, due to its ability to recognize a specific cell-surface determinant(s), 'targets' the liposome to a specific tissue or cell type (reviewed in Papahadjopoulos, D. (1993) in Liposome Technology (Gregoriadis G., ed.), Vol. 3, pp. 1–14, CRC Press, Boca Raton, Fla.). Various types of liposome-attached targeting ligands have been exploited, ranging from small ligands such as folate to larger, protein ligands such as transferrin. Ligands such as those described, however, are typically limited to a single ligand-receptor system, and methods for efficient coupling of one such ligand may not be readily transferable to other, even related ligands. It is for this reason that antibodies (and their fragments) have been chosen as the liposome-attached 'targeting' ligand in many reports (reviewed in Papahadjopoulos (1993) in Liposome Technology (Gregoriadis G., ed.), Vol. 3, pp. 1–14, CRC Press, Boca Raton, Fla.), since a number of monoclonal and polyclonal antibodies exist against a variety of cell-surface proteins.

The coupling of antibodies to liposomes may be accomplished via the chemical and biosynthetic approaches noted above. The most common chemical method of antibody-liposome coupling involves the use of amine-reactive agents, which by modifying protein lysine residues, typically in a non-specific manner, can perturb antigen binding and/or create neoepitopes. Another concern in the use of intact antibodies is the presence of the Fc portion of the antibody, which contains regions involved in classical complement activation and Fc receptor-mediated clearance, both of which may enhance the rate of clearance of the liposome-antibody complexes in vivo. Such problems may be overcome by the use of anitbody Fab' fragments, which lack the antibody Fc region and are therefore less likely to be cleared by the above mechanisms. More importantly, Fab' fragments are ideal for chemical modification using thiol-specific reagents, since they contain a circumscribed coupling site consisting of antibody 'hinge'-derived cysteine residue(s), which is distant from the antigen-binding regions and therefore do not perturb the latter.

'Targeting' of liposomes via surface-coupled antibodies has proven an effective method to modify the biodistribution and/or the pharmacokinetic behaviour of liposomes in various applications (Wolff, B. and Gregoriadis, D. (1984) Biochim. Biophys. Acta 802: 259–273; Kalvakolanu, D. V. R. and Abraham, A. (1991) Biotechniques 11: 218–225; Storm et al., (1994) J. Liposome Res. 4: 641–666). A variety of techniques has been proposed and exploited for the covalent coupling of antibodies to liposomes (for reviews see Heath T. D., and Martin, F. J. (1986) Chem. Phys. Lipids 40: 347–358; Allen et al. J. Liposome Res. 4: 1–25.

Gene Therapy

By gene therapy as used herein refers to the transfer of genetic material (e.g. DNA or RNA) into a host to treat or prevent a genetic or acquired disease or condition phenotype. The genetic material of interest encodes a product (e.g. a protein, polypeptide, peptide, functional RNA, antisense) whose production in vivo is desired or which has the effect of increasing production of a second active product of interest. For example, the genetic material of interest can encode a hormone, receptor, gene sequence, virus (and other vectors), enzyme, polypeptide or peptide which affects the level of NO. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy, cells are removed from a host, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the host subject, rather the genetic material to be transferred is introduced into the cells (to the nucleus, cytoplasm or other organelles with DNA (e.g. mitochondria)), of the recipient organism in situ, that is within the recipient. In an alternative embodiment, if the host gene is defective, the gene is repaired in situ (Culver, (1998) Antisense DNA & RNA Based Therapeutics. Coronado, Calif. Abstract). These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible or promoter to allow selective transcription or a conditional promoter (e.g. under control of a tetracycline-responsive element and subject to on/off control by the use of tetracycline). Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature.

Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated or immune response-mediated events.

A specific example of DNA viral vector for introducing and expressing recombinant sequences is the adenovirus derived vector Adenop53TK. This vector expresses a herpes virus thymidine kinase (TX) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of an antibiotic or other formulations. Such protection ensures that if, for example, mutations arise that produce altered forms of the viral vector or recombinant sequence, cellular transformation will not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cyle of, for example, retrovirus and is the process by which a single infected cell produces many progeny virions that bud off and infect neighbouring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if DMD is to be treated then a vector specific for muscle cells could often but not exclusively be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site or sites. However, local aministration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of treatment or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

VI. STEROIDS:

The NO-related treatments of the present invention are applicable in conjunction with steroid hormone treatment.

The mechanisms underlying glucocorticoid effects (by deflazacort and prednisone) on skeletal muscle in muscular dystrophy are not known. Suggested mechanisms include motivation, increased muscle mass, immunosuppression, myoblast proliferation (Angelini et al., (1994) Muscle Nerve. 17: 386–391), or greater satellite cell recruitment and fatigue resistance (Khan M. A. (1993) J. Neurol. Sci. 120: 8–14). Other anti-inflammatory drugs do not improve muscle strength. Glucocorticoids can affect the expression of laminin and matrix proteins in non-muscle tissues (Lannes-Vieira et al., (1993) Int. Immunol. 5: 1421–1430; Ekblom et al., (1993) J. Cell Biol. 123: 1037–1045) and there are glucocorticoid response elements in the laminin gene (Vuolteenaho et al. (1990) J. Biol. Chem. 265: 15611–15616; Lee et al. (1994) J. Cancer Res. Clin. Oncol. 120: 513–518). Thus increased matrix laminin could mediate attachment (Simo et al., (1992) J. Cell Sci. 101 (pt 1): 161–171) of myoblasts prior to fusion and may stabilize the sarcolemma of fibers lacking dystrophin.

The muscle repair processes are affected by an increase or decrease in thyroid hormone, (Anderson J E et al. Muscle Nerve (1994) 17: 64–73; McIntosh L M et al. (1994) Muscle Nerve 17: 444–453.) likely in part through thyroid response elements on the muscle regulatory genes, myoD and myogenin. As well, experiments showed that anabolic steroids (Krahn M J et al. (1994) J Neurol. Sci. 125: 138–146) and cyclosporine therapy (Sharma KR et al. Neurology (1993) 43: 527–532) can positively affect muscle repair. Together these studies suggest that immunosuppression or lower rates or forces of contraction might decrease dystrophic damage in DMD.

Prednisone (PR) generally improves muscle strength in DMD (Brooke M H et al. (1987) Arch Neurol. 44: 812–817) and reduces cell death in human muscle cell cultures. Prednisone also enhances myogenesis (myotube formation) of mdx muscle cultures (Metzinger L et al. (1993) Neurosci Lett. 155: 171–174) and increases strength and endurance in mdx mice (Hudicki MS et al. Res Commun Chem Pathol Pharmacol (1993) 79: 45–60). The side effects of prednisone treatment include (Khan M A. (1993) J Neurol. Sci. 120: 8–14) Cushingoid appearance, irritability, and decreased bone density, and limit its therapeutic usefulness, especially in young people. Deflazacort, an oxazoline derivative of prednisone, has similar treatment effects to date in increasing muscle strength but fewer side effects (Angelini C et al (1994) Muscle Nerve 17: 386–391; Khan MA. (1993) J Neurol. Sci. 120: 8–14) than prednisone, although it is certainly not without important side effects that may cause discontinuation of treatment.

To date, deflazacort has shown dramatic benefits to dystrophic skeletal muscle in mice or DMD patients, a result matched by no other drug treatment. Deflazacort treatment on mdx mice produced a significant, 1.5–2 fold increase in precursor cell proliferation and formation of new muscle fibers. Deflazacort promotes muscle repair by actions: (a) on the cycling of proliferative myoblasts, (b) on the differentiation and attachment of newly formed muscle fibers, and (c) on secondary involvement of myofibers adjacent to sites of primary fiber injury. The three actions combine to improve muscle function and prevent fibrotic tissue overgrowth of skeletal muscles (particularly diaphragm) in the mdx dystrophic mouse model of Duchenne muscular dystrophy.

There are a large number of potential derivatives or prednisone or methyl-prednisolone, and other steroids that may have similar effects; (e.g. anabolic steroids are known to increase muscle mass in conjunction with a positive nitrogen balance (protein) and ongoing muscle activity (training)). These compounds are contemplated within the scope of the present invention.

In a preferred embodiment, NO, NO donor, inhibitor of NO activity or a regulator of NO production is used to augment the beneficial effects of glucocorticoids and could thereby be used to decrease the effective dose of deflazacort or other emerging glucocorticoids. In a most preferred embodiment, the NO, NO donor, inhibitor of NO activity or a regulator of NO production is used with deflazacort.

VII. MUSCLE DISEASE AND CONDITIONS:

The NO-related treatments of the present invention are applicable to any condition where regeneration or growth of muscle is desired.

In one embodiment, the invention may be used as part of pre- or post-surgical procedures, to promote, encourage or allow optimal or efficient repair of muscle damage by muscle regeneration rather than formation of scar tissue and fibrosis.

In another embodiment, the invention may be used as part of rehabilitation procedures by stimulating muscle formation, and thereby increasing muscle function after muscle disuse or wasting, e.g. after bedrest or confinement, stroke or coma induced incapacitation, arthritis, casting, peripheral nerve section and regrafting) and in anticipation of a requirement to prevent permanent atrophy using rehabilitation strategies in anticipation of secondary or curative surgical or medical/pharmacologic treatment.

The NO-related treatments of the present invention are useful particularly in the treatment of diseases and conditions in which muscle disease-specific processes frustrate muscle regeneration (e.g. genetic mutations of pathways involving the genes for muscle regulatory proteins (MyoD, myf5, myogenin, MRF4), growth factors (e.g. basic fibroblast growth factor, hepatocyte growth factor/scatter factor, insulin-like growth factors, insulin, and their relevant receptors), and in conditions characterized by muscle fiber instability or rigidity or loss of or excessive adhesion between the satellite cell and the fiber (e.g. originating from genetic mutation or toxic exposure). As an example, important linkages may be weakened a) between the fiber cytoskeleton, sarcolemma and extracellular matrix/external lamina, b) between the sarcolemma, M-cadherins and other adhesion proteins and satellite cells, c) between fusing muscle precursors, d) between extracellular matrix and growth factors, and e) between enzymes/proteins and extracellular matrix or sarcolemma.

Specifically, NO-related treatments of the present invention are useful for regenerating damaged muscle tissue, in particular in dystrophic muscles such as Duchenne, Becker, Emery-Dreifuss, Landouzy-Dejerine, Scapulohumeral of Seitz, Limb-girdle (Erb), von Graefe-Fuchs, Oculopharyngeal, Myotonic (Steinert) and Congenital dystrophies or any condition where atrophy and/or fiber loss are prevalent and contributory to decreased functional capacity.

In another embodiment, the NO-related treatment of the present invention can be used to increase muscle mass in normal muscle, e.g. during aging and athletic activity in humans or animal species (e.g. horse, dog). The manipulation of muscle precursor cell activation may be directed differentially to different muscles which are distinctly susceptible to various conditions such as injury, disease, functional demands, muscle-specific endurance training and individual use.

Practice of the invention will be more fully understood from the following examples, which are presented herein for illustration only and is not intended to limit the invention in any way.

EXAMPLE 1

Preliminary Procedures for Manipulating NO Level

Male normal mice (C57BL/6 and B6, 129SF (Jackson Laboratories)), mdx mutant mice (C57BL/10 ScSn, Central Animal Care Services, University of Manitoba) and NOS-I knockout mice (B6,129S-Nos1$^{tm/plh}$, Jackson Laboratories), 6–8 weeks-of-age were treated double-blind, in order to guidelines of the Canadian Council on Animal Care (reference #R-99–003). Studies were designed to determine the effects of manipulating NOS activity on the number and myogenic nature of cells isolated from muscles with and without injury, and examine longer term effects of NOS inhibition.

NOS activity was influenced by an intra peritoneal (ip) injection (80–100 $\mu$l by Hamilton syringe) exactly 30 min. before crush to the right tibialis anterior (TA) muscle of mice rested at least a week after transport from the breeding facility. Mice were injected with saline or saline containing one of three drug treatments as follows: the NOS inhibitor N$\omega$-nitro-L-arginine methyl ester (L-NAME, 7.5, 10, or 15 mg/kg), the NO donor L-arginine (L-Arg, 225 mg/kg) or combined L-NAME (7.5 mg/kg) plus L-Arg. Fifteen min.

later, animals were anesthetised (ketamine:xylazine ip). The crush injury was delivered to the right TA muscle (RTA) using a hemostat clamp closed for 3 sec (McIntosh et al. 1994. Muscle Nerve 17:444–453). Skin was held closed or sutured for longer recovery (see below). The time course study from 0–30 min. after injury was completed in one day for each treatment group, treatments were coded, and each set of experiments were carried out by the same individual(s).

The time course of treatment effects was determined at two intervals; during the early response 0, 5, 10 and 30 min after injury, and over the longer term after 6 days recovery. Short term experiments were repeated at least twice. The longer term animals were maintained either on plain drinking water or water containing fresh L-NAME at 12.5 mg/100 ml (30 mg/kg/day), based on an intake of 6–7 ml/day/mouse (McIntosh et al., 1994. 17:444–453). In the longer term repair studies, there were 4 normal mice in each of saline- and L-NAME-treated groups. An additional 2 normal and 2 mdx mice were injected once before injury with L-NAME and given plain water for 6 days.

Tissues were rapidly harvested within 1–2 min. after cervical dislocation under anesthesia. Whole muscles were carefully dissected from animals in order: RTA, left TA (LTA), left extensor digitorium longus (LEDL), left (LSOL) and right soleus (RSOL), and weighed (TAs and RSOL). Muscles were used to determine cell yield or embedded for cryosectioning (7 µm thick) to examine morphology.

Cell yield was determined immediately after tissue collection. Satellite cells from RTA, LTA (representative fast-twitch muscles) and RSOL (a representative slow-twitch muscle) were isolated by standard procedures (Allen et al., 1998 Methods Cell Biol. 52, 155–162) modified for brevity and to collect only the cells available for harvest after a short digestion. Briefly, connective tissue was removed, muscles were minced to a slurry in phosphate-buffered saline (PBS), and digested for 1 hr. (37° C.) in 1 ml of 0.125% protease XIV (Sigma, St. Louis Mo.) with inversion every 15 min. Samples were triturated for 1 min. and enzyme action was stopped by adding 10 ml growth medium (DMEM containing 15% fetal bovine serum, 1% antimycotic, 0.5% gentamycin, and 2% chick embryo extract; GibcoBRL, Grand Isl., NY). Cells were pelleted by centrifugation (1500g for 4 min.) and the supernate discarded. Cells were resuspended in 15 ml warm PBS, filtered through Nitex gauze and centrifuged (150 g for 4 min.). The pellet was resuspended in 500 µl sterile PBS. A 100 µl aliquot of cell suspension was diluted in 10 ml isotone for Coulter counting. The number of cells isolated per muscle (cell yield) was calculated and plotted over time. In three preliminary experiments, cells were counted using a hemocytometer, to ensure that they were nucleated cells and not isolated myonuclei or red blood cells.

In order to characterise the cell yield from each muscle, remaining cells were plated on 35 mm petri dishes pre-coated with polylysine and fibronectin, and cultured in growth medium for 1–5 days under 95%: 5% $CO_2:O_2$ at 37° C. Some cultures were incubated for the final 30 min. with bromodeoxyuridine (BrdU, 1 mg in 2 ml medium) to label DNA synthesis. After washing in PBS, cells were fixed (10 min.) in 1% paraformaldehyde in PBS and blocked (10% horse serum plus 1% bovine serum albumin in PBS) prior to routine immunostaining (Tatsumi et al. (1998) Dev. Biol. 194: 114–128) using antibodies against BrdU (diluted 1:1, 000, Sigma) or c-met receptor protein (diluted 1:400, Santa Cruz Laboratories). Negative control slides were incubated in blocking solution without primary antibody. Appropriate peroxidase-conjugated secondary antibodies (diluted 1:250–1:400) and DAB/CoNi visualization (Dimension Laboratories) were used to determine the relative myogenicity (c-met+ staining) and level of proliferation (BrdU+ staining).

In the same experiments (n=8 animals, repeated twice) the LSOL and LEDL were embedded for cryosectioning to monitor effects of treatment or remote injury on tissue histology, as visualized by fresh hematoxylin and eosin staining (H&E) and immunostaining for c-met and m-cadherin (see below).

In the longer term study of NOS inhibition during repair, saline and L-NAME-treated normal mice recovered for 6 days. Two mice per group were injected 2 hr before sacrifice with BrdU (i.p., 1.6 mg in 0.4 ml saline) and sections were immunostained using anti-BrdU antibodies as above.

A separate experiment was conducted to study the immediate effects of injury on muscle and satellite cell histology. LTA and RTA were collected immediately at 0 and 10 min. after crush from normal mice after saline or L-NAME pretreatment (total n=4). Muscles were bisected longitudinally, and half of each muscle was frozen in OCT. for cryosectioning. Sections were stained with H&E or immunostained using primary antibodies to c-met (1:400), HGF/SF (1:1000, R&D Systems) or developmental myosin heavy chain (devMHC, 1:250, Novocastra Laboratories) as reported (Permitsky et al. (1996) Exp. Cell Res. 22: 214–222; Tatsumi et al. (1998) Dev. Biol. 194: 114–128) or against m-cadherin (1:50, Santa Cruz). The other half of each muscle was fixed in 2.5% glutaraldehyde in 0.1M cacodylate buffer, pH 7.35, post-fixed in osmium tetroxide and embedded in methacrylate resin.

Sections (0.5m thick) were collected on glass slides and stained with toluidine blue. The inhibition of NOS enzyme activity by L-NAME treatment 30 min. before crush was confirmed using NADPH-diaphorase enzyme histochemistry on frozen sections with jejunal epithelium as the positive control, according to Beesley (1995) Histochem. J. 27: 757–769.

Sections and cultures were viewed on an Olympus microscope equipped with epifluorescence and phase contrast optics. Observations were based on systematic viewing of 2–4 longitudinal sections per muscle (separated by >100m). In the case of muscle regenerating from crush injury, observations (without knowledge of treatment group) were made in pre-set fields of muscle from the central crush region, the adjacent regenerating region and the surviving region as reported (McIntosh et al. (1994) Muscle Nerve 17: 444–453). Representative photographs of muscle fibers and satellite cells were taken on over 700 frames of ASA 400 Fuji Sensia slide film. Where stated, the number of satellite cells observed in each category, group or condition was estimated from photographed slides rather than from direct counts made during observations under oil immersion. Selected slides were scanned (Olympus Film Scanner ES-10, Olympus Optical Co., Tokyo), formatted into plates with little or no enlargement and printed (Freehand 8.0, Macromedia Inc.).

EXAMPLE 2

Effects of NOS Manipulation in Normal Mice

The myogenic nature of cells isolated from muscles in the 0–30 min. time course was confirmed by counting the proportion of c-met+cells 12–24 hr. after plating. Myogenic cells formed the large majority of cells isolated from the normal LTA (83–94%) and RTA muscles (86–92t) (n=997 cells). After 24 hours in culture, cells were typically round or elongated, and 10–25% had nuclei that were intensely positive for BrdU incorporation. After 4–5 days in culture, dark c-met staining was present in single cells and in small multinucleated myotubes. Cultured cells from different treatments, recovery times and muscles were identical in appearance despite differences in cell yield (see below).

Muscle weight as a proportion of body weight (FIGS. 1A–D) was used to monitor edema secondary to tissue damage. The weight of muscles dissected from saline-treated normal mice showed a 10–15% increase in RTA over LTA that began immediately after injury. During L-NAME treatment RTA weight increased only at 10 min. relative to LTA while L-Arg and combined L-NAME plus L-Arg treatment produced little or no change in muscle weight profile. Since the profile of RTA weight differed over time and among the four normal treatment groups, cell yield was expressed as cells per muscle, based on the assumption that LTA and RTA in one normal animal have similar-sized populations of myogenic precursors. Other observations made during tissue collection suggested that RTA haemorrhage at the crush site in the L-NAME-treated animals appeared later and at 30 min. was subjectively more pronounced than in the other three groups.

Cell yield in the time course 0–30 min. after injury in normal mice changed dramatically with treatment and differed between LTA and RTA (and RSOL) muscles (FIGS. 1E–H). After saline treatment, the LTA released $2.0 \times 10^5$ cells at 0 min. (herein referred to as basal LTA level). In marked contrast, the crushed RTA from the same mouse yielded two-fold more cells at 0 min. The RTA cell yield dropped briefly from 5–10 min. and then rose again. Surprisingly, at 10 min. the LTA yield doubled over the basal yield (LTA at 0 min.), and then declined below basal by 30 min. The yield from RSOL (an uninjured slow-twitch muscle ipsilateral to RTA, and included for comparison with fast-twitch TA) was lower than from LTA on a per muscle basis (although 2–7-fold higher expressed as cells/mg), and did not change over the 30 min. time course. The data compiled from three repeat experiments on normal mice treated with saline (including C57BL/6 and B6, 129SF mice) are presented as the ratio of cell yield in RTA/LTA (mean±SEM) in FIG. 2 and demonstrate the consistent large immediate rise in cell yield at 0 min.

L-NAME treatment (7.5 mg/kg) substantially changed the time course of cell yield, preventing the initial injury-induced rise in RTA yield (FIG. 1F) and delaying the increased cell yield until 10 min. after injury. The yields from LTA and RSOL were lower at 0 min. than in the saline-treated mice (15 and 50%, respectively). Notably, 30% fewer cells were isolated at 0 min. from RTA than LTA. By 10 min., yields from RTA and LTA were higher (3.5 and 2-fold, respectively) than at 0 min. By 30 min., cell yield from both RTA and LTA had dropped once again. This time course was consistent, as shown by a plot of relative cell yield (RTA/LTA ratio, mean±SEM) from 3 experiments on normal muscle (FIG. 2) showing the prevention of immediate cell release from RTA relative to LTA at 0 min. L-NAME treatment at flanking doses indicated that the delayed peak RTA yield could be shorter (3 mg/kg) or longer (10 or 12.5 mg/kg) than 10 min. after injury (one experiment at each dose) without the high RTA yield at 0 min. Interestingly, while peak cell yield in RTA was delayed (not reduced) by L-NAME, the peak in cell yield from LTA (at 10 min.) was reduced but not delayed after L-NAME treatment.

In the time course of cells isolated from mice treated with L-Arg, the basal yield of LTA was similar to that after saline, then rose and stayed high until 30 min. The RTA yield rose sharply at 5 min., and also stayed high. RSOL counts were unchanged.

Combined treatment with L-NAME and L-Arg increased the yield in LTA and RTA by 50% at 0 min. compared to saline-treated mice. While LTA yield gradually fell over 30 min., RTA yield at 5 min. was the highest yield observed from a normal TA ($6.0 \times 10^5$ cells/muscle) and dropped again by 10 min. The RSOL yield after combined treatment showed the only changes of any group of normal RSOL muscles. A sharp 80% rise between 0 and 5 min. after RTA injury was followed by a decrease to the level at 0 min.

EXAMPLE 3

Effects of NOS Inhibition in MDX Dystrophic Muscle Vs. NOS-I Knockout in Muscle

Since satellite cells are intimately contoured to fibers and often stay attached to the external lamina as the sarcolemma buckles after injury (Schultz and McCormick, 1994 Rev. Physiol. Biochem. Pharmacol. 123, 213–257), they are ideally positioned to be "first responders" to a shear-induced release of NO from the subjacent NOS-I$\mu$. As activation would increase the harvest of myogenic cells from a single muscle by reducing their adhesion to fibers and lamina, and would also affect subsequent muscle repair, the release of myogenic cells from single crush-injured muscles was used as an index of the collective process in muscle. Experiments were carried out in normal mice pretreated to inhibit or augment NOS activity, and one tibialis anterior (TA) muscle was crush-injured 30 min. later. Cell yields from injured and undamaged muscles were determined over 30 min. immediately after crush, and longer term repair was also examined.

The mdx mutant of the C57BL/10ScSn strain of genetically dystrophic mouse has been proposed as an animal model applicable to the study of hereditary X-linked human muscular dystrophies (Bulfield, G., W. G. Siller, P. A. L. Wight, and K. J. Moore (1984). Proc. Natl. Acad. Sci. U.S.A. 81: 1189–1192). Skeletal muscle from these mice has been characterized morphologically to show a rapid, early limb muscle destruction prior to 4 weeks of age, which is accompanied by inflammation and prominent features of muscle regeneration (Dangain and Vrbova (1984). Muscle Nerve. 7:700–704). The prevalence of such necrosis in muscle may be dependent on the strictly homozygous nature of a particular colony (Bridges, L. R. (1986). J. Neurol. Sci. 72: 147–157). In addition, foci of myocardial necrosis in mdx mice have been noted (ibid, Anderson et al., Muscle Nerve 1994) and are similar in appearance to the cardiac involvement in some human dystrophies (Adams, R. D. (1975). Harper and Row, Hagerstown, Md., p. 289).

The mdx mouse displays X-linked dystrophin-deficient myopathy. In mdx mice, fiber injury in the limb muscles is followed by dramatic repair of muscle structure (e.g. Anderson, J. E. et al. (1987) Anat. Rec. 219: 243–257) and largely successful recovery of limb muscle function (e.g Anderson, J. E. et al. (1988) J. Muscle Res. Cell Motil. 9: 499–515) compared to DMD. However, the diaphragm muscle of mdx mice shows severe damage, fibrosis and poor repair very similar to DMD (Stedman, H. H. et al. (1991) Nature 352: 536–538; Dupont-Versteegden, E. E., and R. J. McCarter (1992) Muscle Nerve 15: 1105–1110). (Petrof, B. J. et al. (1993) Proc. Natl. Acad. Sci. USA 90: 3710–3714). The mdx diaphragm is the obvious comparison with DMD tissue, but quite difficult to sample as systematically as limb muscles, considering muscle architecture and the huge number of small, short fibers in various orientations (Anderson JE et al. (1998) Muscle Nerve 21: 1153–1165). However, there is a repair response in the diaphragm: myoblasts are dividing, and new muscle fibers (called myotubes) are present. If a drug did improve repair, more new muscle fibers (marked by developmental myosin and containing central nuclei) should form, possibly by increased recruitment and proliferation of myoblasts cells.

A number of morphological similarities to human Duchenne-type muscular dystrophy have been observed in the mdx model. In human DMD, early focal and segmental degeneration in skeletal muscles have been described (Fardeau, M. (1969) Muscle Diseases. J. N. Walton, N. Canal, and G. Scarlato, eds. International Congress, Excerpta Medica, Milan, pp. 99–108). Injured fibers exhibit misaligned and nonpolarized myofibrils with differential Z/I or A-band loss, hypercontraction (Cullen, M. J., and F. L. Mastaglia. (1980) Br. Med. Bull. 36: 145–152), dilation of the sarcoplasmic reticulum (Mair, W. G., and F. M. S. Tome. (1972). Churchill Livingstone, Edinburgh), and plasma membrane defects (Mokri, B., and A. G. Engel (1975) Neurology 25: 1111–1120). Cardiac muscle involvement has also been noted (Adams, R. D. (1975). Harper and Row, Hagerstown, Md., p. 289). The resistance of small skeletal muscle fibers to necrosis (Karpati, G., S. Carpenter, and S. Prescott (1982). Muscle Nerve 5: 369–372; Karpati, G., S. Carpenter, and S. Prescott (1986) Neurology 36(Suppl. 1): 240 Abstract) and concurrent early spontaneous regeneration are, however, ineffective in preventing fiber loss during the dystrophic process. Duchenne dystrophy progresses with abortive regeneration by forked or branched muscle fibers (Mastaglia, F. L., and B. A. Kakulas (1969) Brain 92: 809–818; Mastaglia, F. L., J. M. Papadimitriou, and B. A. Kakulas (1970) J. Neurol. Sci. 11: 425–444) and increased numbers of myosatellite cells (Wakayama, Y. (1976) J. Neuropathol. Exp. Neurol. 35: 532–540). Indeed, membrane defects, fibrosis, and adipose tissue proliferation seen in Duchenne dystrophy were hypothesized prior to discovery of the dystrophin gene, to be primary abnormalities or to be causative of impaired regeneration in the human disease (Mendell, J. R., R. Higgins, Z. Sahenk, and E. Cosmos (1979) Ann. N.Y. Acad. Sci. 317: 409–430; Sweeny, P. R., and R. G. Brown (1981). Comp. Biochem. Physiol. [B] 70: 27–33). The minimal extent of fibrosis, the normal or above-normal number of fibers, and the absence of adipose connective tissue deposits in the large muscles of the mdx mouse are where this model most notably diverges from the morphological characteristics of the progression of human dystrophy.

Genetically the mdx mouse is similar to humans with Duchenne muscular dystrophy (DMD) in that muscles in both lack dystrophin, (Hoffman E P, Brown R H Jr, Kunkel L M. (1987) Cell 51: 919–928) which is crucial to muscle integrity. However, mdx limb muscles respond to muscular dystrophy with an active myoproliferative response (Anderson J E, Ovalle W K, Bressler B H. (1987) Anat. Rec. 219: 243–257; Grounds Md., McGeachie J K. (1989) Cell Tissue Res 255: 385–391) which appears to stabilize the number of fibers in limb muscles. (Anderson J E, Ovalle WK, Bressler B H. (1987) Anat Rec 219: 243–257; Matsumura K, Ervasti J M, Ohiendieck K, Kahl S D, Campbell KP. (1992). Nature 360: 588–591). Although the level of active dystrophy and repair in mdx limb (Anderson J E, Ovalle W K, Bressler B H. (1987) Anat Rec 219: 243–257; Anderson J E, Bressler B H, Ovalle W K. (1988) J. Muscle Res. Cell Motil. 9: 499–516; Anderson J E, Lui L, Kardami E. (1991) Dev Biol 147: 96–109; Dangain J, Vrbova G. (1984). Muscle Nerve. 7:700–704; Karpati G, Carpenter S, Prescott S. (1988). Muscle Nerve. 11:795–803) and cardiac. (Anderson J E, Lui L, Kardami E. (1991). Dev. Biol. 147:96–109; Bridges L R. (1986). J Neurol Sci. 72:147–157) muscles gradually decreases with age, it is not precisely known what permits dystrophin-deficient mdx muscle to respond so well to dystrophy. Some small caliber myofibers, such as extraocular fibers, are spared from DMD and mdx dystrophy, (Karpati G, Carpenter S, Prescott S. (1988). Muscle Nerve. 11:795–803) possibly due to substitution by utrophin. (Matsumura K, Ervasti J M, Ohiendieck K, Kahl S D, Campbell K P. (1992). Nature. 360:588–591). However, the absence of utrophin from large mdx limb muscles, except at neuromuscular junctions, (Matsumura K, Ervasti J M, Ohiendieck K, Kahl S D, Campbell K P. (1992). Nature. 360:588–591) does not account for the successful recovery of limb muscles from dystrophy, in contrast to the progression of DMD.

Muscle in mdx mice lacks subsarcolemmal NOS-I$\mu$and shows rapid repair and precursor cycling (McIntosh et al., 1994. Muscle Nerve 17:444–453; McIntosh and Anderson, 1995. Biochem. Cell Biol. 73:181–190; Permitsky and Anderson, 1996. Exp. Cell Res. 22:214–222), while NOS-1 knockout mice have complete loss of NOS-I expression (Huang et al., 1993. Cell 75:1273–1286). Therefore the effects of low or absent NOS expression (similar in outcome to NOS inhibition) on cell yield in mdx and NOS-I knockout mice, and on mdx satellite cells and muscle repair were examined (Examples 1 to 7). The rapid activation of satellite cells by injury, shown by increased myogenic cell release and morphological changes, was delayed by NOS inhibition induced pharmacologically by L-NAME and by primary and secondary defects in NOS-I gene expression. Activation was transiently observed with a slower time course in intact contralateral muscles and NOS inhibition negatively affected muscle regeneration.

Figure 1I:
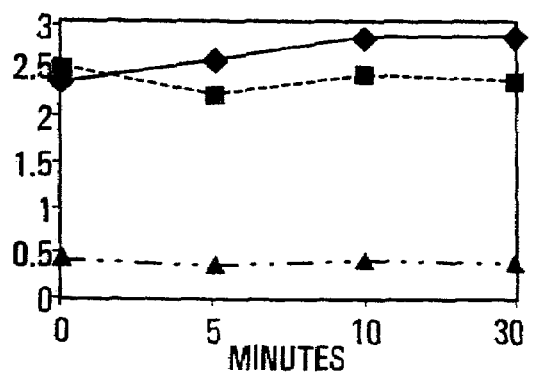
Figure 1J:
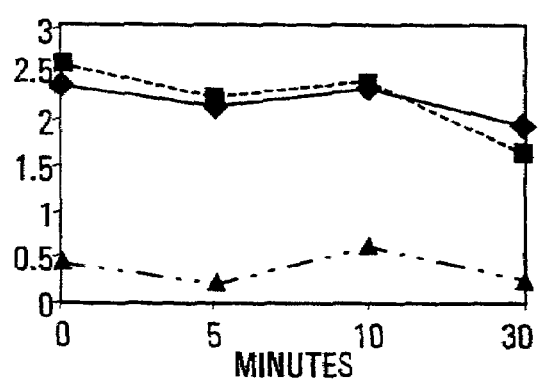

The myogenic proportions of cells isolated from mdx muscles were very high in LTA and RTA (95% and 96% respectively, 295 cells counted) and likely included both satellite cells from fibers and myoblasts from the interstitium of dystrophic muscles. Muscle weight as a proportion of body weight had a different profile in mdx than in normal mice (FIG. 1I). RTA weight increased later (after 5 min) and was maintained over 30 min. in saline-treated mdx mice, while L-NAME abolished the increase in RTA weight for 30 min. (FIG. 1J). During tissue collection, mdx RTA muscles were subjectively less hemorrhagic after L-NAME than after saline treatment.

Figure 1K:
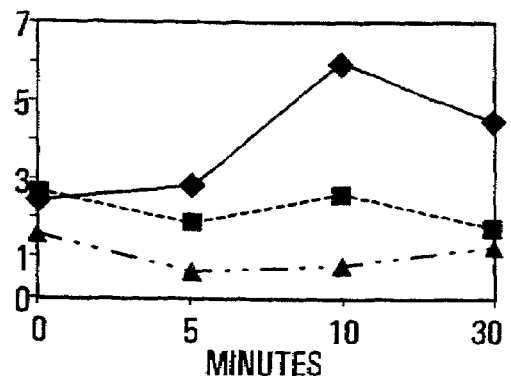

The time course of cell yield from saline-treated mdx mice (FIG. 1K) showed five major distinctions from that in saline-treated normal mice, and more closely resembled the profile of the normal muscle yield after NOS inhibition. First, the basal level of LTA yield was about 30% more in mdx than normal mice. In mdx mice, RTA yield did not show an immediate rise at 0 time. Instead, counts for LTA and RTA were similar. Over 10 min., the RTA yield doubled and then levelled off somewhat. The cell yield from LTA did not change over time, while RSOL yields dropped by half from 0–10 min.

Figure 1L:
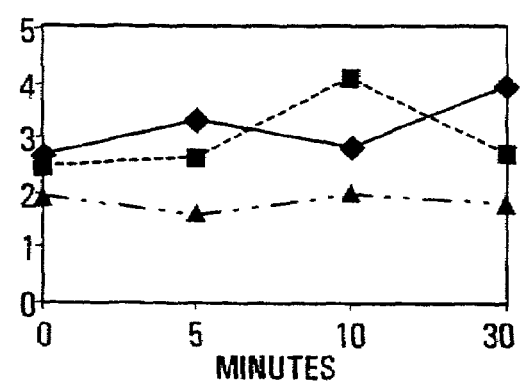

The cell yields of LTA and RTA from L-NAME-treated mdx mice at 0 min. were similar to yields from saline-treated mdx mice, and again higher than in normal mice (FIG. 1L). LTA yield increased by 50% at 10 min. and returned to basal yield by 30 min. (as in normal mice after L-NAME). RTA yield rose slowly over the 30 min. time course. After L-NAME, the cell yield from mdx RSOL did not change over time. Thus NOS inhibition in mdx mice increased cell yield from uninjured LTA. NOS inhibition also decreased and further delayed the peak of myogenic cells isolated from the injured mdx RTA muscle compared to saline treatment in mdx mice.

Figure 2:
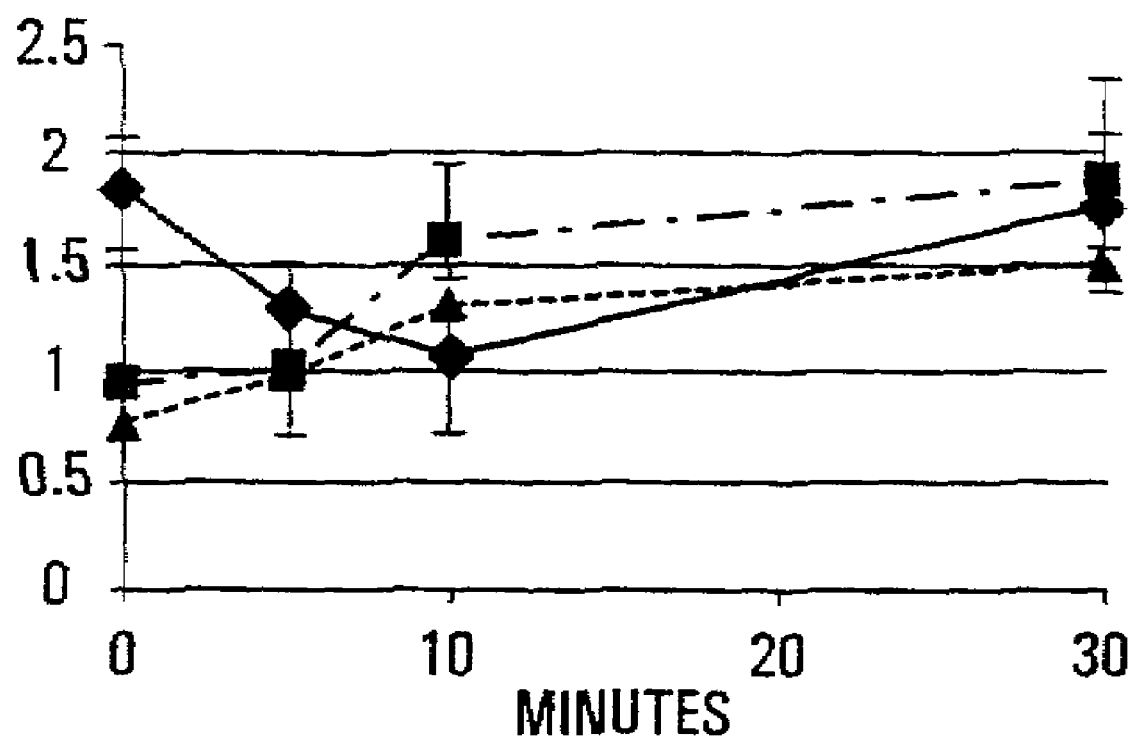
FIG. 2: Time course of cell yield (cells/muscle) expressed as the ratio of RTA:LTA (mean±SEM) for normal mice (C57BL/6 and B6,129SF, 3 experiments, ▼), normal mice treated with with L-NAME (C57BL/6, 3 experiments, ▲) and "NOS mutant" mice including mdx and B6, 129S-Nos1$^{tm/plh}$ (NOS-I knockout) mice (3 experiments, ■). Satellite cell activation (cell yield ratio of RTA:LTA) in normal mice begins at 0 min. and is significantly greater than in mice with NOS inhibition as a result of pharmacological treatment (by L-NAME), a primary gene defect (NOS-I knockout mice) or secondary to dystrophin deficiency (mdx mice).
Figure 3B:
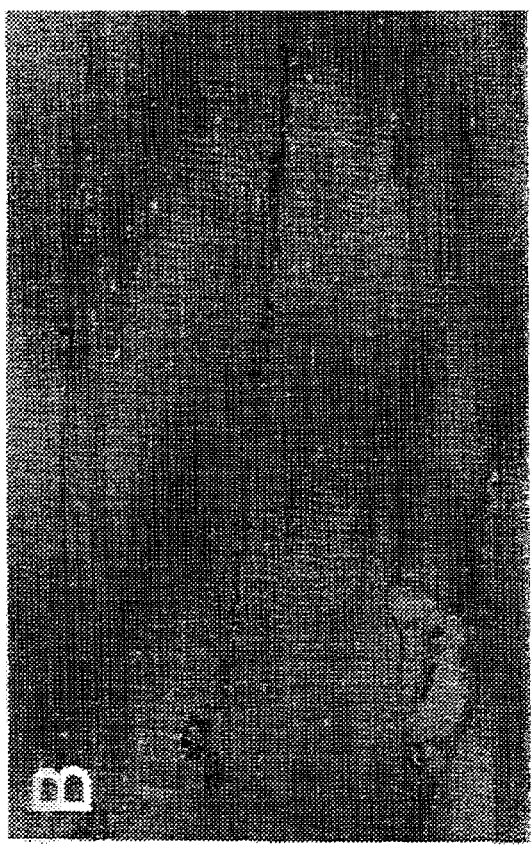
FIG. 3: Representative effects of crush in normal muscle at 0 min. (A, B) and 10 min. (C-E) after injury and after saline (A, B, E) or L-NAME (C, D) pre-treatment. (A) LTA section shows normal undamaged muscle. (B) RTA section at 0 min. after crush injury. (C) At low magnification, a dark band of hypercontraction in fiber segments (to the left) and extravasated blood cells between fibers are thin and retracted to the light of the hypercontracted region. (D) Two delta lesions in a fiber after L-NAME and 10 min. after crush. (E) Higher magnification view of muscle 10 min. after injury showing extravasated blood cells between hypercontracted and retracted fiber segments and segments with early sarcomere disruption. Original magnification A, B, D, E, X132; C X33.
Figure 3C:
Figure 3A:
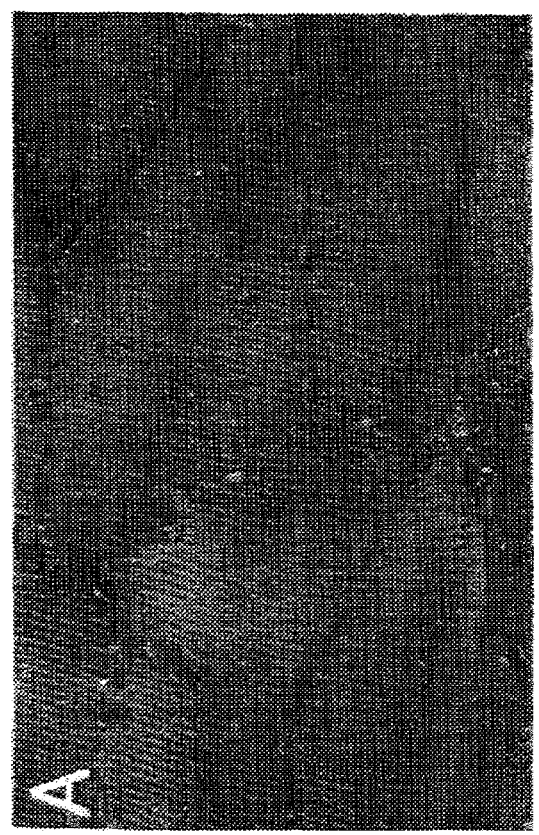
Figure 3E:
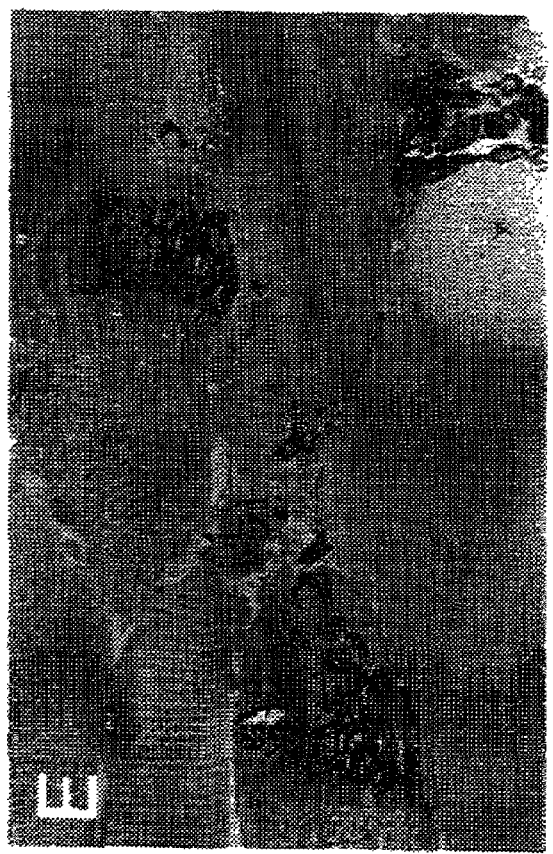
Figure 3D:
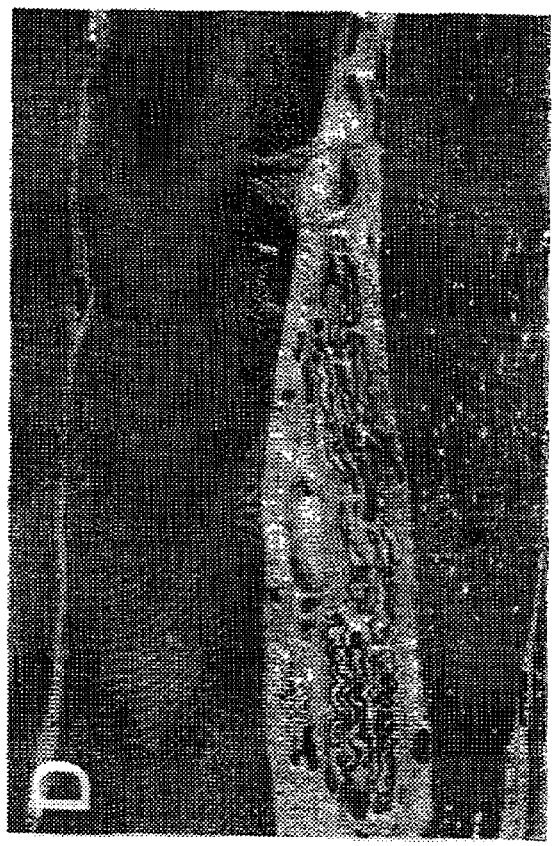

NOS-I knockout mice showed a time course of cell yield from LTA, RTA and RSOL that was very similar to that in mdx mice, summarized in FIG. 2 (3 experiments, pooled data from mdx and NOS-I knockout mice). The time course of cell yield in mdx and NOS knockout mice, expressed as the ratio of RTA/LTA yields, showed no difference from the profile of cell yield in L-NAME treated normal muscle. The immediate increase in cell yield in RTA of normal mice was absent in RTA muscle of both mdx and NOS-I knockout mice.

EXAMPLE 4

Effects of NOS Inhibition on Early Muscle and Satellite Cell Responses to Injury All the RTAs collected immediately after injury showed a crush site at 0 min. that was very similar to uncrushed muscle (FIG. 3, data from n=4). After only 10 min. however, overt microscopic damage was present in the crushed region of all RTA sections of both saline and L-NAME-treated mice, including transverse bands of fiber hypercontraction, delta lesions and empty or disrupted external lamina directly at the crushed site.

Histology and immunostaining showed that normal rapid changes in satellite cell size and position were consistently delayed and restricted after L-NAME treatment (FIG. 4, data from n=10–12, except n=2 per group for resin sections). NADPH-diaphorase staining experiments on sections from the same mice confirmed that pre-treatment with L-NAME inhibited NOS activity, detected as a thin outline located just inside the sarcolemma of all muscle fibers from saline-injected animals. The identity, position and configuration of approximately 300 satellite cells observed on fibers were confirmed by m-cadherin and c-met staining. M-cadherin was interposed between fibers and all satellite cells observed in undamaged muscle, and typically surrounded large satellite cells on fibers in saline-treated RTA at 0 and 10 min. (FIG. 4A). At 10 min., large m-cadherin+cells were very often observed on the empty external lamina sheaths present after fiber retraction (FIG. 4B). Interestingly satellite cells were easily visible on nearly every fiber by H&E staining at 0 min. at the RTA fiber periphery (FIG. 4C) and were often prominent in the RSOL, LEDL, LTA and RTA at 10 min., since they contained large vesicular nuclei and many crimson cytoplasmic granules, likely mitochondria (FIG. 4D). After saline treatment, c-met staining of LTA at 0 time consistently showed typical attenuated satellite cells very close to fibers. However, RTA at 0 min. showed many large satellite cells (approximately 50 of 65 satellite cells, and a higher proportion in the crushed regions) that were c-met+ and HGF/SP+ (FIG. 4E) and had a higher ratio of cytoplasm to nucleus than satellite cells in the contralateral LTA. Those enlarged satellite cells often bulged from the fiber contour even at a distance from the crush region in RTAs. The same features were more pronounced at 10 min. after crush in RTAs (FIG. 4F), although 15–20% of satellite cells were small and attenuated, positive for m-cadherin or c-met in their location on some undamaged fibers at the edge of the crushed region.

Figure 4E:
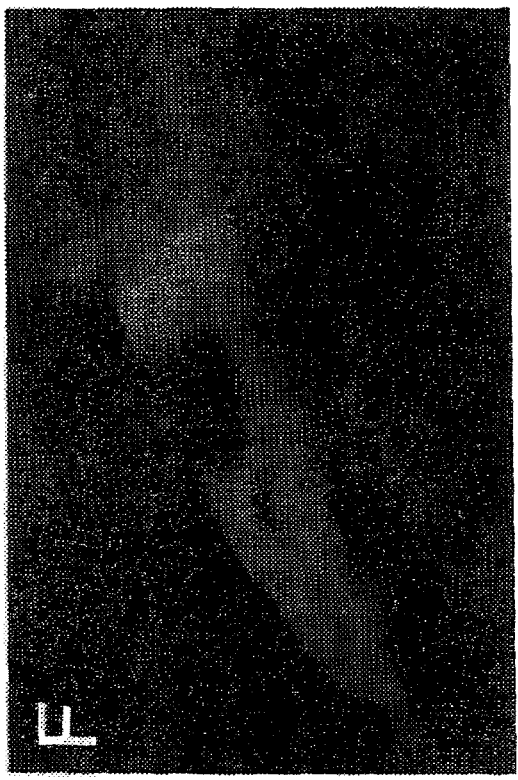
FIG. 4: Satellite cell changes in vivo are delayed by NOS inhibition in normal mice treated with saline (A–H) or L-NAME (I–P). (A) M-cadherin outlines a large satellite cell at 0 min. after injury. (B) Large m-cadherin+ satellite cell on the external lamina 10 min. after injury. (C) H&E-stained satellite cells (arrows) in low magnification RTA fibers at 0 min. (D) At high magnification, hypertrophic satellite cells on fibers in RSOL (and RTA, not shown) at 10 min. (E&F) Large satellite cell shows co-localized (yellow) staining for HGF/SF (Texas-red) and c-met (FITC) at 0 min. (E) and 10 min. (F). (G) Two resin sections (stained with toluidine blue) show large satellite cells (between arrowheads) at 0 min. in RTA. (H) At 10. min. in RTA, satellite cells (arrows) with granulated cytoplasm and euchromatic nuclei are partially lifting off adjacent fibers.
Figure 4F:
Figure 4G:
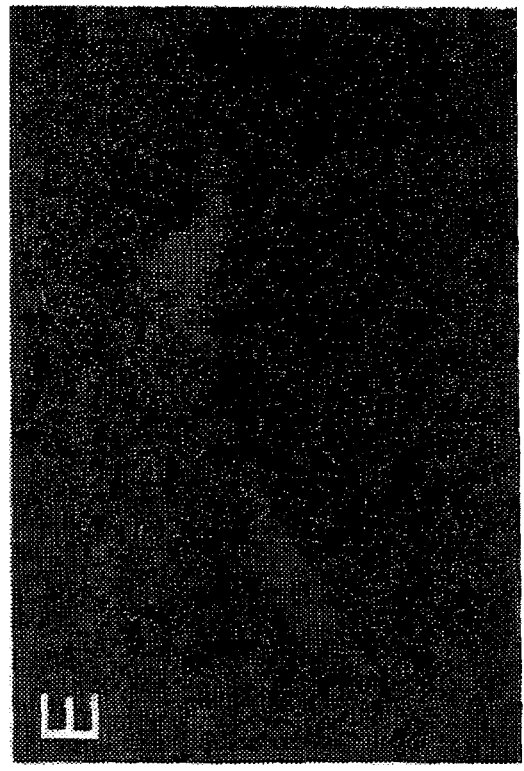
Figure 4H:
Figure 4J:
Figure 4L:
Figure 4I:
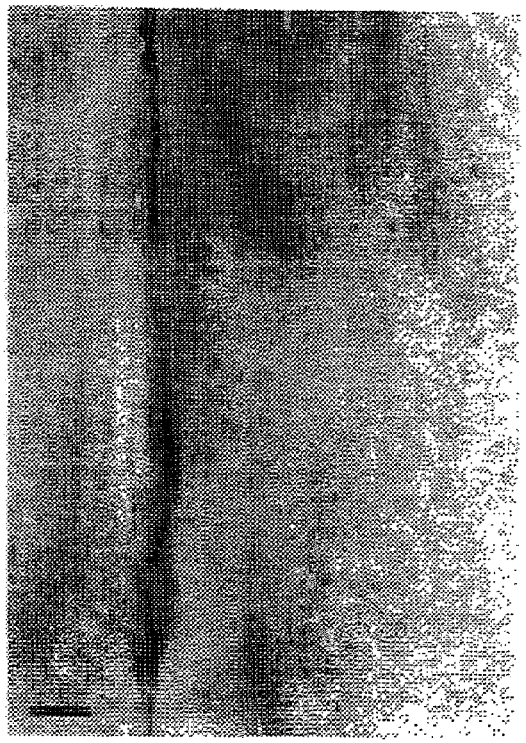
Figure 4K:
Figure 4M:
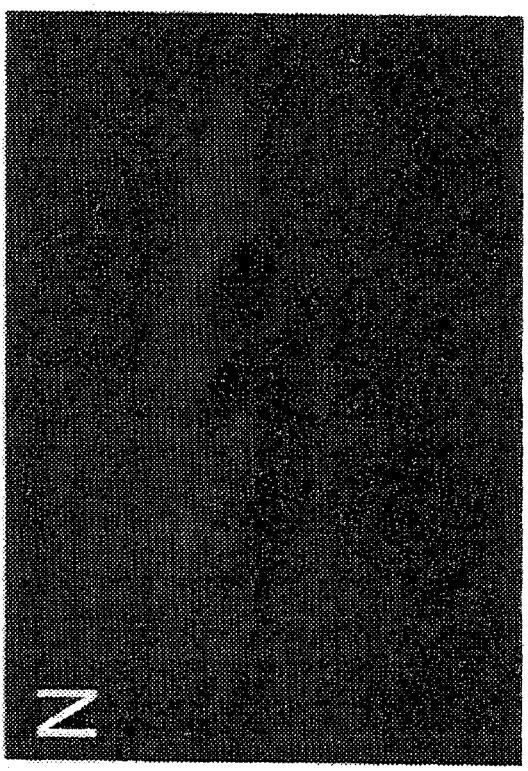
Figure 4N:
Figure 4O:
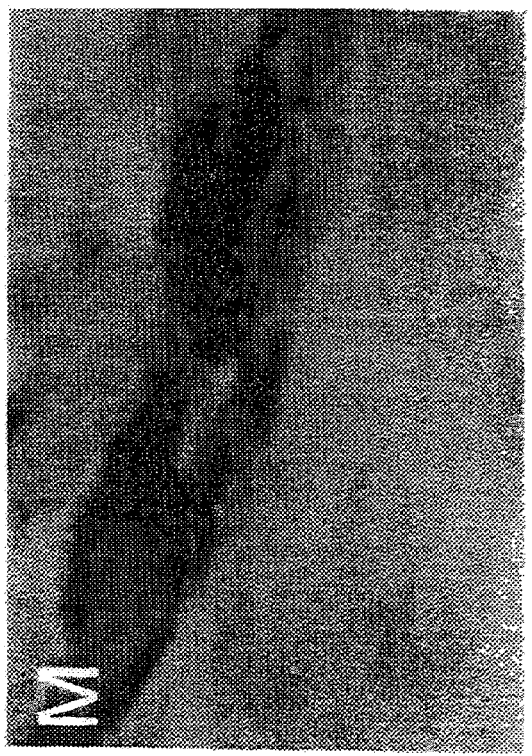

By contrast in L-NAME-treated mice, the large majority of satellite cells (85% of more than 70 satellite cells identified by either m-cadherin+ or c-met+staining) were thin and attenuated in both the RTA and LTA at 0 min. (FIG. 4I), were not prominent by H&E staining) (FIG. 4J) or were c-met+but did not stain for HGF/SF (FIG. 4N). However, by 10 min. there were typically large m-cadherin+satellite cells on many fibers in every section (FIG. 4M) and c-met and HGF/SF were co-localized in at least 70% of satellite cells (25–30 were clearly observed per longitudinal section) bulging from fibers (FIG. 4O) or at the external lamina. These features of cell enlargement and c-met/HGF co-localization were also less frequent after L-NAME than saline treatment, in observations made at the surviving ends of the RTA fibers not directly injured by the crush.

Figure 4P:
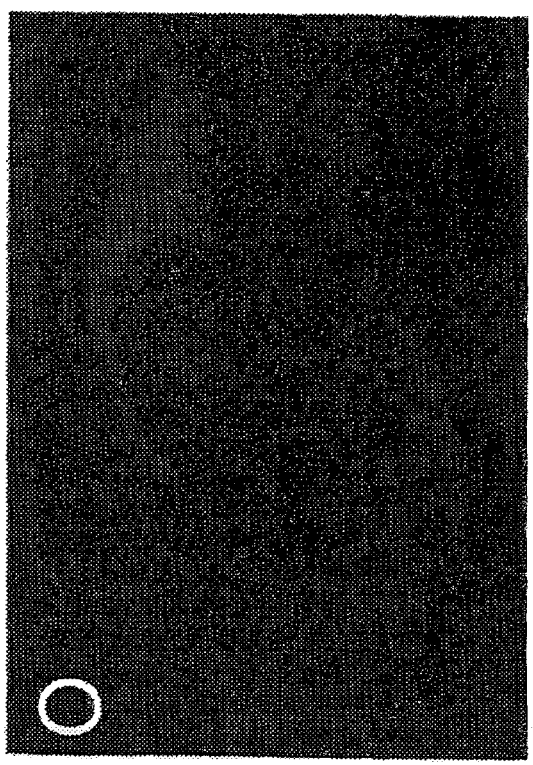

Resin sections showed details of more than 50 cells in the satellite position on fibers, and later confirmed by electron microscopy as satellite cells and containing a nucleus. Large satellite cells were only present at 0 time in the injured region of RTAs from saline-treated mice (FIG. 4G). They were demarcated from the subjacent fibers, contained large vesicular nuclei with prominent nucleoli, and had many dark cytoplasmic granules identical to typical mitochondria between fibrils and at the fiber periphery (FIG. 4G). By 10 min. in RTA from a saline-treated mouse, the large satellite cells were often present, and similarly were observed lifting from fibers (FIG. 4H). By comparison, nuclei and cells in the satellite position of LTA and in the RTA from an L-NAME-treated mouse at 0 time were typically thin, nearly agranular and their nuclei could seldom be distinguished from internal myonuclei as the cells were in tight apposition to fibers (FIG. 4K). At 10 min. after injury, many myonuclei inside fibers had a folded nuclear membrane on the aspect adjacent to hypercontracted fibrils (FIG. 4L), and were easily distinguished from the smoothly contoured nuclei of enlarged satellite cells at the fiber periphery (FIG. 4P).

EXAMPLE 5

Effects of NOS Inhibition on Longer Term Repair in Normal Muscle

Figure 5A:
Figure 5B:
Figure 5C:
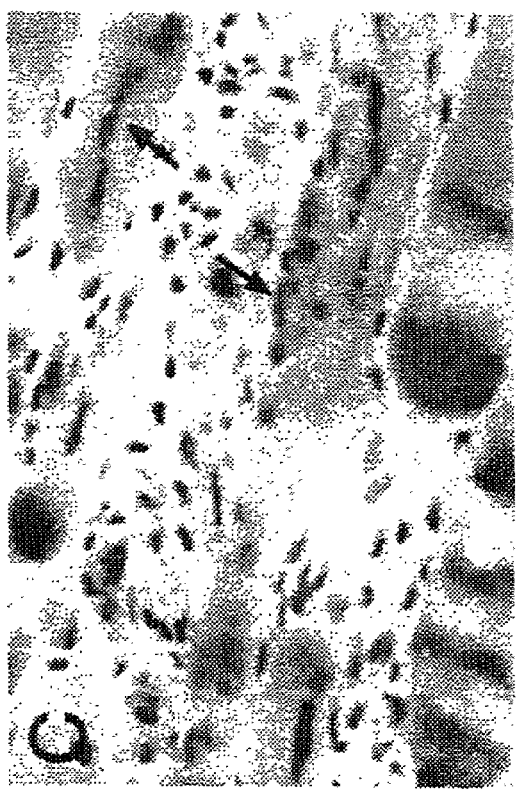

After 6 days recovery from injury, normal mice treated with a saline injection and plain drinking water (n=4) had RTAs with a small characteristic central necrotic crush site flanked by small myotubes (FIGS. 5A–C). In systematic observations of adjacent and surviving regions (McIntosh et al., 1994 1994 Muscle Nerve 17, 444–453) of 4 different sections per muscle, adjacent regions contained many mononuclear cells and capillaries between the long myotubes. Surviving tissue at the ends of RTA contained fibers interspersed or continuous with new myotubes. Many mononuclear cells (over half of 20–30 satellite cells clearly identified per section) stained for both c-met and HGF/SF, while myotubes did not stain for either protein.

Figure 5E:
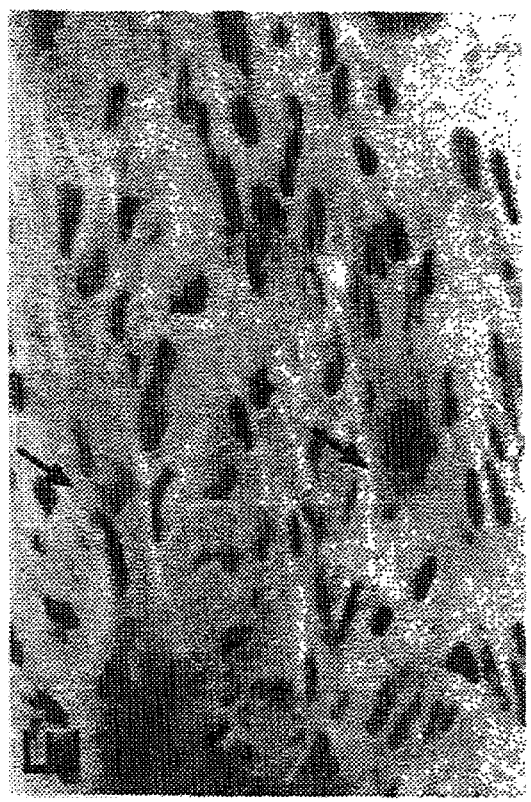
Figure 5D:
Figure 5F:

By contrast, muscle regeneration was reduced by exposure to L-NAME over the 6 days of repair (n=4) (FIGS. 5D–F). Outside a large central crush site, persistent necrotic fiber segments contained macrophages and some calcifed fiber segments which were infrequent in RTAs of saline-injected mice. Many mononuclear cells surrounded the thin basophilic (immature) myotubes which in addition, were seen at much lower density per field compared to myotubes in similar RTA fields from saline-treated mice. New myotubes were also infrequent among surviving fibers at the ends of RTA after L-NAME. The prevalence and size of new myotubes were confirmed by devMHC-positive immunostaining.

Interestingly, a single injection of L-NAME before injury had also produced subtle effects on muscle regeneration after 6 days (n=2) (FIG. 6). RTAs had small remnant crush lesions, mononuclear cells in the adjacent regions, numbers and size of myotubes, similar to normal regenerating muscle, and many mononuclear cell nuclei were BrdU+ (FIG. 6G). However, in regions of surviving segments, large cells in the satellite cell position (m-cadherin+) had granular cytoplasm and were connected directly with long, thin myotubes while still resident on fibers within the external lamina. This feature was observed at least once in every 40× field containing surviving fiber segments in the region adjacent to the crush site. A small number (estimated at 5–10%) of myotubes appeared to be incompletely fused blocks of eosinophilic (FIG. 6F) or devMHC+ cells, especially notable with phase contrast optics. New, small devMHC+ myotubes were continuous with larger myotubes formed since the injury (FIG. 6H) or were located among mononuclear cells adjacent to the injury site. Four m-cadherin+ satellite cells were seen on new myotubes (FIG. 6L). Satellite cells were always very intensely stained in the spindle fiber complexes (FIG. 6M), and in undamaged EDL or SOL from the same mice, satellite cells were very prominent and intensely eosinophilic on many fibers (FIGS. 6J, K).

EXAMPLE 6

Effects of NOS Inhibition on Longer Term Repair in Dystrophic Muscle

Figure 6A:
Figure 6B:
Figure 6C:
Figure 6D:
Figure 6E:
Figure 6F:
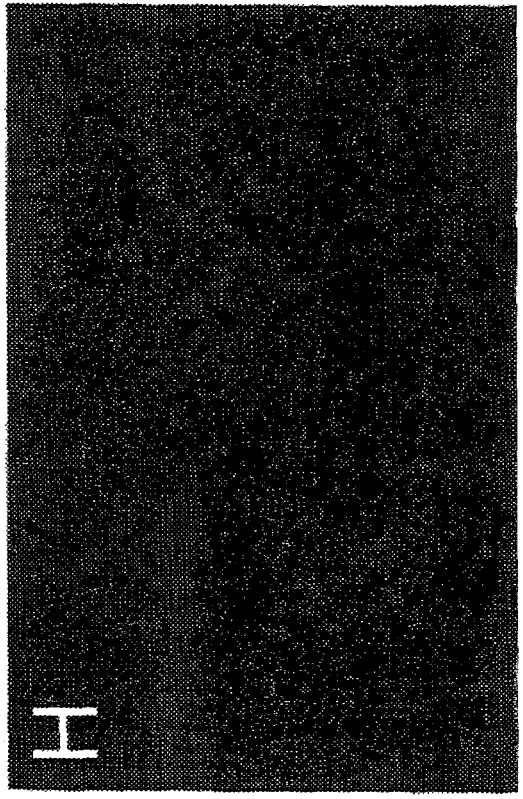
Figure 6G:
Figure 6H:
Figure 7A:
Figure 7B:
Figure 7C:
Figure 7E:
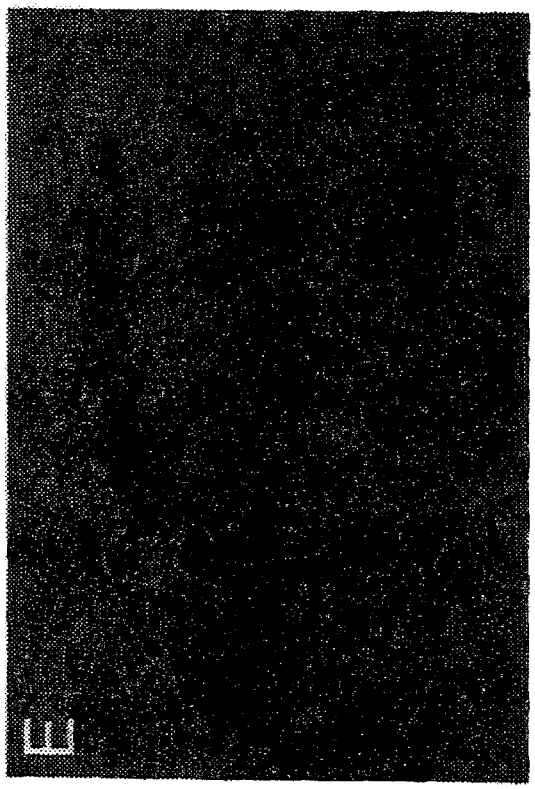
Figure 7D:
Figure 7F:
Figure 7H:
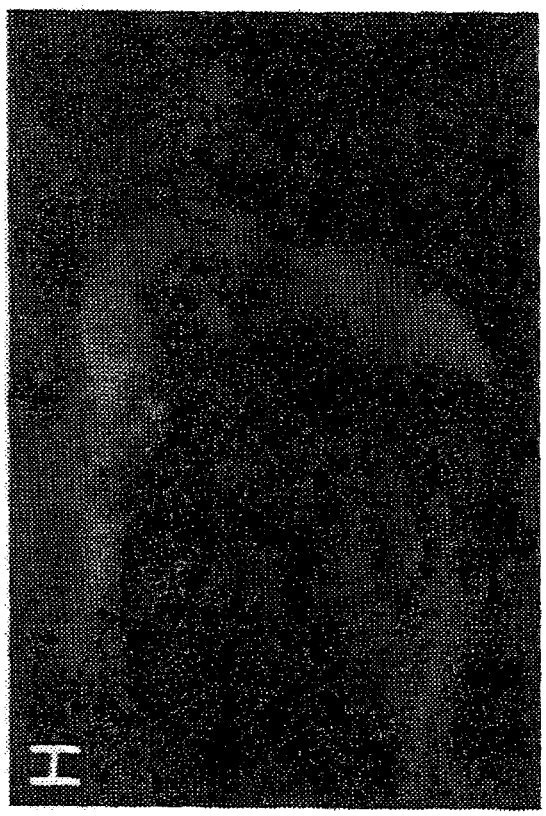
Figure 7G:
Figure 7I:
Figure 8A:
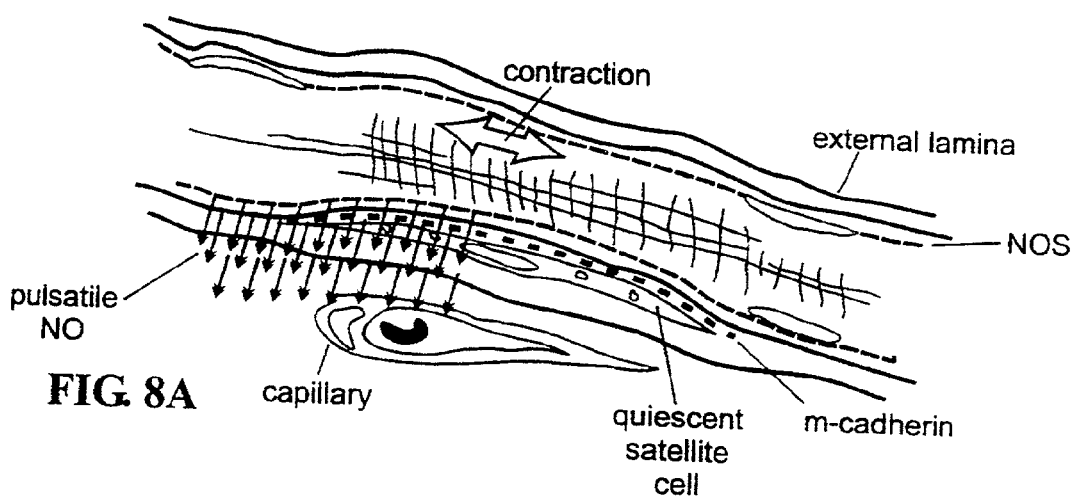
Figure 8B:
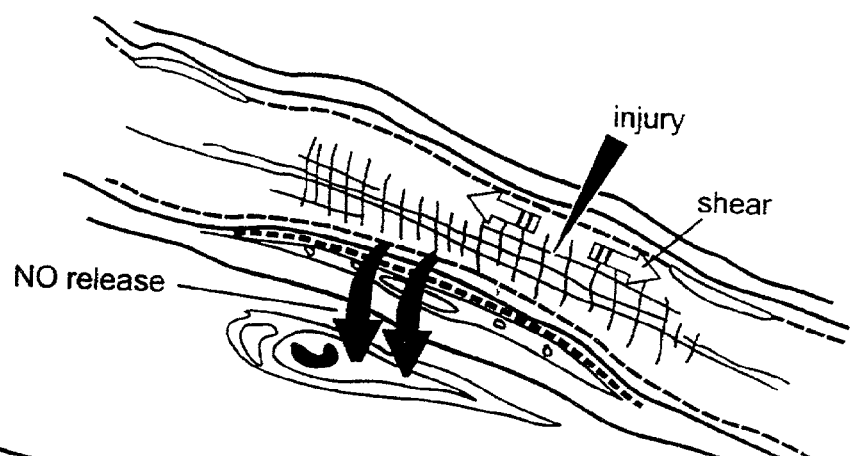
Figure 8C:
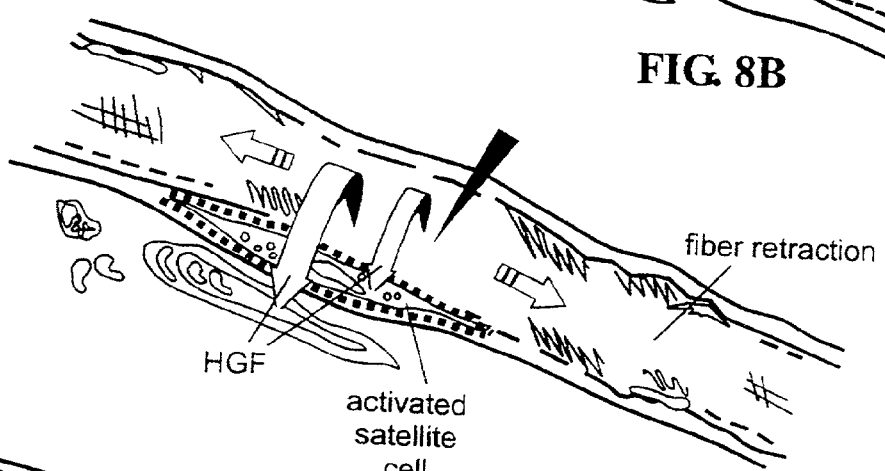
Figure 8D:
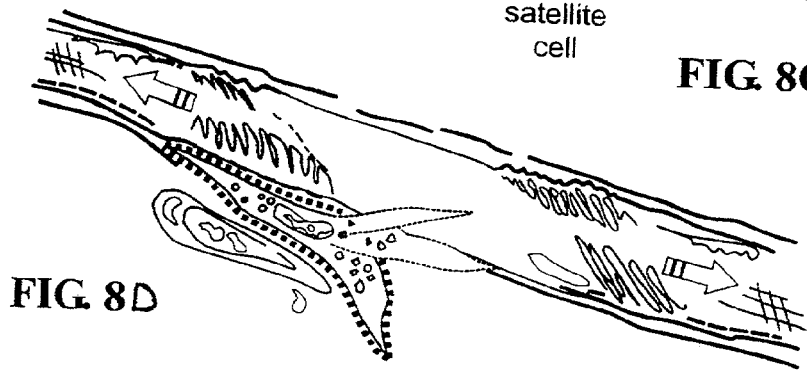

A single L-NAME injection also produced subtle changes in regenerating mdx muscles over 6 days (n=2) (FIG. 7). In regenerating muscles of L-NAME-treated mice, many large new myotubes extended from a small necrotic crush site, through the adjacent region and between the fiber segments that survived the injury (FIG. 7A). More large myotubes were present compared to normal regenerating muscle, as previously reported for mdx mice (McIntosh et al., 1994 1994 Muscle Nerve 17, 444–453; McIntosh and Anderson, 1995 1995 Biochem. Cell Biol. 73, 181–190), and many satellite cells, elongated mononuclear cells and new myotubes were m-cadherin+(FIG. 7C). In one field, a binucleate satellite cell was lifted off the fiber sarcolemma (FIG. 7D). DevMHC was expressed by new myotubes (FIG. 7E), and BrdU+ nuclei were found in nearby mononuclear cells and in some muscle precursor cells close to surviving fiber segments and new myotubes (FIG. 7F). Three fields of regenerating muscle (in the two animals) also contained small collections of intensely BrdU+ nuclear fragments in myotubes (FIG. 7G). As in normal mice treated once with L-NAME, satellite cells (outlined by m-cadherin) were observed in continuity with the new myotubes that were anchored inside external lamina sheaths on remnant fiber segments (roughly 5% of new myotubes, not shown here). Satellite cells in mdx LTA were very large and c-met+(FIG. 7H) as were satellite cells in NOS-1-knockout LTAs although their extensive cytoplasm was not as granulated or as distinct from fiber sarcoplasm by H&E staining as in normal undamaged muscles after L-NAME treatment (FIG. 7I, compare with FIGS. 6J, 6K).

Prior to identifying HGF/SF as an activator of satellite cells, the nature of activation was elusive as it was studied with later markers, such as regulatory gene expression or DNA synthesis. The present demonstration in satellite cells of a rapid shift by HGF/SF to its "mitogenic and motogenic" receptor (Rong et al., 1994. Proc. Natl. Acad. Sci. USA 91:4731–4735) upon activation confirms a previous report (Tatsumi et al., 1998. Dev. Biol. 194:114–128).

EXAMPLE 7

Satellite Cell Morphology From Mice 0 and 10 Minutes After Crush Injury and After Pretreatment With Saline or L-NAME Measurements of cell area (size increases in activated cells), nucleus-to-cytoplasm ratio (a measure that decreases with activation), and cytoplasmic density (a measure that decreases in activation with the increase in cell size, despite the hypertrophy of cytoplasmic organelles) were made from electron micrographs without knowledge of their source. Two investigators had to agree on the satellite cell identification before cells were included in the study, with the stipulation that cell profiles had complete nuclei and cell membrane visible in a photograph or montage (all photographs taken at identical magnification of 10,000×) Satellite cells originated from the central crush-injured region of muscles collected from each mouse (n=4). Cytoplasmic density was determined as [the integrated cell density minus the integrated nuclear density] divided by [cell area minus nuclear area]. A computer was used to scan micrograph negatives, and digital images were analyzed using the program NIH Image for morphometry.

TABLE 1

| group & time post-crush | cell area (arbitrary units) | nucleus: cytoplasm ratio (%) | cytoplasmic density (arbitrary units) |
| --- | --- | --- | --- |
| L-NAME treated | | | |
| 0 minutes (n = 8) | 9.0 ± 1.6 | 70.2 ± 1.7 | 91.7 ± 5.8 |
| 10 minutes (n = 3) | 6.3 ± 1.1* | 52.0 ± 8.7* | 66.2 ± 2.1* |
| Saline treated | | | |
| 0 minutes (n = 8) | 9.6 ± 1.7 | 72.3 ± 1.9 | 125.0 ± 7.7◊ |
| 10 minutes (n = 6) | 9.8 ± 2.5◊ | 60.8 ± 3.4◊* | 122.7 ± 5.2◊ |

*indicates a significant difference from the same group at 0 minutes post-crush injury.
◊ indicates a significant difference from saline-treated group at same time post-crush injury.

By classical morphologic criteria, satellite cells in saline-treated mice were activated at 10 minutes (increased cell size, decreased nucleus:cytoplasm ratio, decreased cytoplasmic density). L-NAME inhibition of NOS activity maintained quiescence over 10 minutes (only nucleus:cytoplasmic area decreased, but significantly less than in saline-treated mice). Results from electron microscopy of resin sections are consistent with these conclusions, i.e, quiescence at 0 min with L-NAME and activation at 0 and 10 min with saline; activation being delayed to 10 min with L-NAME Treatment.

EXAMPLE 8

Role of NO in Satellite Cell Activation

Results from the preceding Examples show that satellite cell activation occurs immediately upon muscle injury, is mediated by NO release, is briefly transmitted to distant muscles and is prevented under pharmacologic and genetic conditions that reduce the activity or expression of NOS-I. Time-course studies of myogenic cell yield and morphology showed two aspects of activation, namely altered adhesion and morphological changes. Prior to identifying HGF/SF as an activator of satellite cells, the nature of activation was elusive as it was studied with later markers, such as regulatory gene expression or DNA synthesis. The present demonstration in satellite cells of a rapid shift by HGF/SF to its "mitogenic and motogenic" receptor (Rong, S., Segal, S., Anver, M., Resau, J. H., and Vande Woude, G. F. (1994). Proc. Natl. Acad. Sci. USA 91, 4731–4735) upon activation confirms a previous report (Tatsumi, R., Anderson, J. E., Nevoret, C. J., Halevy, O., and Allen, R. E. (1998). Dev. Biol. 194, 114–128), and their disposition between fiber and lamina sheath suggested that the physical signal of injury was rapidly transduced from a fiber to activate its satellite cells. In vivo studies on myogenesis after injury demonstrated that pharmacologic inhibition of NOS activity was detrimental to the outcome of muscle regeneration. Interestingly, two mutants with decreased or absent NOS-I expression show enhanced activation in situations when normal muscle is quiescent, and show very effective repair after an imposed injury. Together these acute and chronic experiments strongly indicate a pivotal role for NO in transducing activation, satellite cell adhesion and repair.

For the first time the nature and possible impact of injury-induced activation were expressly addressed. Data from the preceding Examples showed that reduced NOS activity, either by inhibition with L-NAME in normal muscle, from complete genetic loss of NOS-I expression (in NOS-I knockout mice) or secondary to dystrophin deficiency in mdx muscle, prevented the immediate rise in myogenic cells isolated from injured muscle. Rapid changes in the nuclear profile, cytoplasmic granularity and the ratio of cytoplasm to nucleus were consistent with the known hypertrophic alterations of satellite cells as they become activated, and were also inhibited by L-NAME. That NOS inhibition thereby delayed and restricted injury-induced satellite cell activation, defined by changes in adhesion, cell yield, morphology and in cells expressing two satellite cell markers, c-met and m-cadherin. Studies of non-injured normal muscles showed a surprising albeit short-lived rise in LTA cell yield after 10 min., coincident with hypertrophy of a proportion of those satellite cells, and suggest that a circulating factor can at least transiently activate satellite cells in intact distant muscles. In regenerating muscle, longer term NOS inhibition (by L-NAME in drinking water) delayed removal of debris, decreased the formation of new myotubes and confined them closer than usual to the site of injury. While more subtle changes in repair resulted from a single event of NOS inhibition at the time of injury, the appearance of fiber duplication found inside the persistent external lamina on damaged fibers appeared to divert repair toward fiber branching. The apoptotic nuclear fragmentation (Blandino, G., and Strono, S. (1997). J. Exp. Clin. Cancer Res. 16, 3–10; Evan, G., and Littlewood, T. (1998). Science 281:1317–1322) that was present in regenerating muscles after briefly perturbing activation, could reduce the number of nuclei in new fibers and potentially affect myotube domains and the stability of repair. These data enable more focussed examination of activation and the potential applications of NO manipulation.

A model is presented in FIG. 8 for the hypothesis that NO release mediates satellite cell activation by a mechanism consistent with mechanisms described in other systems (Traub and Berk, 1998. Arterioscler. Thromb. Vasc. Biol. 18:677–686; Dimmeler et al., 1999 Nature 399: 601–605). This working hypothesis broadens the field of NO signalling in muscle (reviewed by Grozdanovic, Z., and Baumgarten, H. G. (1999). Histol. Histopathol. 14, 243–256). The time course of satellite cell release and the onset of organelle hypertrophy were very rapid, occurring by 35–45 s. after injury (from the time of euthanasia to collection and freezing tissue was under 2 min.). No other reports to date show such rapid transduction of morphological or adhesion changes after injury or in repair. Normal cyclic loading of muscle produces pulsatile NO release (Tidball, J. G., Layergne, E., Lau, K. S., Spencer, M. J., Stull, J. T., and Wehling, M. (1998). Am. J. Physiol. 275, C260–266) by the rapid diffusion of NO down it's concentration gradient, and maintains satellite cell quiescence. By contrast, a large release of NO would move as a wave front across the narrow clefts between a fiber and it's satellite cells. The following lapse in NO release would constitute a powerful primary signal, a "nitric oxide transient" in physiological terms. Teleologically, the external lamina wrapping fibers may provide the potential for satellite cells to respond to shear between the sarcolemma and lamina. Satellite cells hug fibers across an even 15 nm cleft without junctional complexes, and they associate closely with external lamina (Bischoff, R. (1990a). J. Cell Biol. 111, 201–207; Schultz, E., and McCormick, K. M. (1994). Rev. Physiol. Biochem. Pharmacol. 123, 213–257). Thus satellite cells have the ideal topography to detect a rapid peak of NO release from underlying fibers after shear and also to be kept quiescent by normally continuous small pulses of NO from the fiber. The speed of the NO-mediated signal for activation suggests that an initiating event such as mechanical shear forces acts on constitutive NOS-I, since the response time is too short to induce expression or increase activity (McCall, T. B., et al., (1991). Eur. J. Immunol. 21, 2523–2527; Rubinstein, I., et al., (1998). J. Clin. Invest. 101, 1325–1333). Effects of L-NAME on edema (and hemorrhage) were congruent with NO effects on vascular tone (Busse, R., and Fleming, I. (1998). J. Vasc. Res. 35, 73–84). Taken together, the time course of cell yield after injury and its change by NOS inhibition suggest that a large NO release is the primary signal that mediates or directly triggers activation. The transient decline in RTA yield at 10 min. in saline-treated normal mice suggests that secondary signals are then needed to maintain or complete activation. The nature of those additional signals was suggested by the brief, delayed increase in LTA yield at 10 min. in both saline- and L-NAME-treated normal mice. Since HGF/SF is released from crushed muscle and activates muscle precursors in vivo and in vitro (Tatsumi, R., et al., (1998). Dev. Biol. 194, 114–128), HGF/SF or other factors may become activated themselves, and circulate from RTA to initiate activation of satellite cells located outside the damaged muscle. Without the NO-mediated signal, however, normal fibers would repress activation and satellite cells would return to quiescence. By contrast, satellite cells in RTA, having received the secondary circulating signal in addition to the primary signal would complete the activation sequence. Combined treatment with an NO donor and a NOS inhibitor partly reversed effects of NOS inhibition on RTA yield and prevented the temporary increase in LTA yield. Therefore, signals involved in fully activating precursor cells likely include both NO-mediated and NO-independent mechanisms.

Shear produced by layers that shift laterally against each other would be strong during segmental retraction within the external lamina. Compared to myoblast transfer and according to the model, intramuscular injection of muscle fibers and their adherent satellite cells is a form of shear which could maximize shear-induced satellite cell activation and supply crushed muscle extract containing (HGF) directly to the site of fiber implantation. This hypothesis therefore can integrate diverse topics of NO physiology, mechanical force transduction, cell signalling, dystrophy and repair. In that context, NO manipulation of satellite cell activation can dramatically improve muscle repair using fiber injection. Transient precursor proliferation in denervation, and persistent proliferation after trauma or segmental disease can be explained by applying the idea of NO-mediated, shear-induced satellite cell activation upon total synchronized nerve and fiber depolarization and then loss of membrane potential. Interestingly, intense m-cadherin+satellite cells in muscle spindles suggest high shear responsiveness may accompany the spindle function as a length-tension receptor. There is also a potential for NO interaction with m-cadherin in mediating loss of adhesion during activation and the ratio of RTA/LTA being less than one at 0 min during NOS inhibition or decreased NOS-I expression (FIG. 2) suggests that reduced NO may mediate an increase in satellite cell adhesion to the fiber-lamina complex.

Until now, satellite cell activation was defined structurally as cytoplasmic and organelle hypertrophy and dynamically as recruitment to cycle. The close adherence of satellite cells to parent fibers must decrease during activation for satellite cells to move through the external lamina to form new fibers. Therefore the loss-of-adhesion feature was used as a simple index of activation. The ability to isolate myogenic cells after brief standard digestion was a conservative estimate of available satellite cells and not an estimate of total myogenic cells. (Additional myogenic cells are found in the material collected on the Nitex filter during cell isolations.) NO is known to modulate leukocyte and platelet adhesion (Kubes et al 1991 Proc. Natl. Acad. Sci. USA. 88, 4651–4655; de Graaf et al 1992 Circulation 85, 2284–2290) and m-cadherin mediates muscle precursor adhesion to fibers. So it is also possible that changes in adhesion during activation, and the m-cadherin molecule itself in repair may be affected by NO. The present data also suggests that specifically manipulating satellite cell activation via changes in NOS-I$\mu$ activity or shear, rather than giving systemic alkali dietary supplements to stimulate bone formation and indirectly stimulate muscle fibers (Landauer and Burke, 1998. Aviat. Space Environ. Med. 69:699–702) could directly prevent muscle atrophy in microgravity.

NO has a broad impact on glucose uptake, insulin resistance, exercise, blood flow and contractility (Balon and Nadler, 1994. J. Appl. Physiol. 77:2519–2521; 1997 J. Appl. Physiol. 82:359–363; Shen et al., 1995. Med. Sci. Sports Exerc. 27:1125–1134; Joyner and Dietz. 1997. J. Appl. Physiol. 83:1785–1796; Kapur et al., 1997. Diabetes 46:1691–1700; Chen et al., 1998. Am. J. Physiol. 274 (Regulatory Integrative Comp. Physiol. 43), R822–R829; Young and Leighton, 1998. Biochem. J. 329:73–79). NO also mediates denervation responses, inflammatory myopathy, aging and neuromuscular transmission (Tews et al., 1997. J. Neuropathol. Exp. Neurol. 56:1283–1289; Tews et al., 1997. Exp. Neurol. 146:125–134; Capanni et al., 1998. Biochem. Biophys. Res. Commun. 245:216–219; Ribera et al., 1998. J. Neurosci. Res. 51:90–102; Tews and Goebel, 1998. Clin. Immunol. Immunopathol. 87:240–247). Therefore, the collective effects of No have a significant impact on muscle pathophysiology. One study of rat muscle after crush injury showed that L-NAME could prevent traumatic shock by inhibiting NOS-II and NOS-III. However, no change in NOS-I activity was reported. Moreover, satellite cells and repair were not examined (Rubinstein et al., 1998. J. Clin. Invest. 101:1325–1333).

An unexpected result from the experiments described above was that short-lived satellite cell activation occurred in normal undamaged fast-twitch muscle, according to dual criteria of hypertrophy in vivo and loss of adherence in cell yield studies. The consistency of the findings was emphasized by comparison with cell yield studies in the slow SOL muscle that expresses less NOS-I$\mu$ (Kobzik et al., 1994. Nature 372:546–548). While the idea that circulating HGF/SF can activate satellite cells in intact muscle needs to be tested, it recalls a report that serum collected after partial hepatectomy-induced shear will stimulate proliferation of liver cells (Wang and Lautt, 1999. Can. J. Physiol. Pharmacol. 76:1–8) which stain intensely for c-met. Distant activation may also involve NO interactions, possibly with a converting enzyme that activates HGF or other factors (Lowenstein et al., 1994. Ann. Int. Med. 120:227–237; Miyazawa et al., 1996. J. Biol. Chem. 269:8966–8970). While the pharmacology of NOS is complex (Reid, 1998. Acta Physiol. Scand. 162:401–409; Nathan and Xie, 1994. Cell 78:915–918), the data for uninjured muscles do suggest that manipulation of NO (through combinations of raised and lowered NO) can prevent or treat muscle atrophy (as from disuse, age or zero gravity) and to promote hypertrophy and new fiber growth (as in meat production, athletic training, animal raising) in otherwise healthy muscle. It also suggests that activation may require an initiating step (e.g. injury-induced NO release) and then need a second step to be fully maintained or completed. That second phase of activation could involve factors activated by NO or released by damaged muscle (such as HGF/SF in crushed muscle extract) to act directly on injured muscle fibers, and indirectly and transiently on uninjured muscles. Results from studies in isolated fiber culture model using DNA synthesis as the marker of completed activation indicate that manipulation of NO is a viable treatment option. Interestingly, in situ hybridization experiments show that satellite cells themselves express NOS-I$\mu$. This suggests that satellite cells may direct (in an autocrine fashion) their own activation by shear or other stimuli, in addition to receiving paracrine signals from fibers.

The present results address for the first time the initial steps of satellite cell activation. A single exposure to NOS inhibition had subtle effects on myotube formation that echo NO-stimulated myoblast fusion in vitro. Longer NOS inhibition reduced the effectiveness of repair and restricted its distribution, in agreement with the idea that shear-induced responses become attenuated longitudinally away from the injury. The significant negative effect of pharmacologic NOS inhibition on myogenic repair reported here was further extended by the recent preliminary studies on repair in NOS-I knockout mice (n≈2), and during longer term NOS inhibition in mdx mice (n≈22). Bearing in mind that L-NAME non-specifically inhibits all NOS activity including vascular smooth muscle and endothelial responsiveness, and will have a broad impact, 3 weeks of systemic L-NAME treatment appeared to increase the severity of dystrophy in diaphragm, SOL, EDL, and TA in young mdx animals.

A model proposes the hypothesis that NO mediates rapid satellite cell activation, including hypertrophy and altered adhesion inside the fiber-lamina complex, and that distant muscle precursors may be transiently activated by circulating factors released from injured muscle. Perhaps the largest insights of this model are the rapidity of activation, and the notion that immediate satellite cell responses to muscle injury may be contributed by the physical character of the external lamina and mechanical shear. The signalling mechanism underlying NOS-I activity in response to shear can also be determined, and may involve Akt/PKB-dependent phosphorylation of NOS-I as recently reported for NOS-III (eNOS, Dimmeler et al., 1999. Nature. 399:601–605). With these signals better defined, new strategies can be devised to promote and regulate the action of satellite cells in disease and repair.

EXAMPLE 9

Role of NO in Satellite Cell Activation in Relation to Duchenne Dystrophy

The marked difference in activation time course between normal and mdx muscle is entirely congruent with the different locations of NOS-I$\mu$ in the two types of muscle, as is the similarity between RTA:LTA yield ratios in muscles from mdx, NOS-I knockout and L-NAME treated normal mice. NOS-I$\mu$ is subsarcolemmal and in mdx muscle is reduced and displaced to the cytosol due to the absence of dystrophin. Mdx muscle pathology was recently reported to be independent of nNOS(NOS-I) perturbation (Chao et al., 1998. J. Neurochem. 71:784–789; Crosbie et al., 1998. Hum. Mol. Genet. 7:823–829). The authors hypothesized that displaced NOS-I contributed free radial NO damage to the sarcoplasm of fibers and would exacerbate dystrophy. However, the idea was rejected, since total removal of NO by NOS-I knockout in mdx mice did not reduce dystrophy. An alternative explanation derives from the present data. Cytoplasmic NOS-I in mdx muscle would act as a diffuse areal source of NO rather than the nearby linear source, typically subjacent and parallel to satellite cells found in normal muscle fibers. The normally steep NO gradient across the cleft between fiber and satellite cell would therefore become more shallow, diffuse more slowly, and the small NO transient would be manifest as an attenuated responsiveness to shear forces. If normal pulsatile NO acts to maintain quiescence, a smaller gradient in dystrophy from the pulsatile NO of cytoplasmic origin, could release mdx satellite cells from what is normally full quiescence, and account for the greater proliferative activity and larger satellite cells in mdx muscle and primary cultures (McIntosh and Anderson, 1995. Biochem. Cell Biol. 73:181–190; Permitsky and Anderson, 1996. Exp. Cell Res. 22:214–222; Moor et al., 2000. J. Microsc. Res. Tech.). Rapid repair by mdx muscle is consistent with the notion that mdx satellite cells are partly activated or on 'standby'. As well, it would follow that acute injury would not necessarily augment immediate activation for mdx and NOS-I knockout mice, as reported here in cell yield studies. By that reasoning, repair after imposed injury in the NOS-I X mdx double mutant should be less effective and/or delayed compared to mdx muscle repair. As well, dystrophy in that double mutant may be more severe than in mdx mice if it were assessed in younger mice (<12 months), before the index of repair (central nucleation) has reached its theoretical plateau. In addition, since human fibers are bigger than mdx fibers, cytoplasmic NOS-I in human fibers would serve as an even smaller non-linear NO source than in mdx muscle. The resulting very shallow gradient or physiological NO transient across satellite cells could partly account for the severity of Duchenne dystrophy, almost as if the standby activation (like a "hair trigger") contributes to overly enthusiastic successive repair events and early senescence (Decary et al., 1996. Human Gene Therapy 7:1347–1350; Decary et al., 1997 Human Gene Therapy 8:1429–1438). It is now clear that satellite cell activation needs to be considered separately from dystrophy.

Three observations are consistent with the cytosolic location of NOS-I$\mu$ and standing activation of mdx satellite cells. Hypertrophic c-met+ satellite cells are typical in mdx muscles without injury (here; Anderson, 1998. Biochem. Cell Biol. 76:13–26). Adult mdx muscle yields high density myoblast cultures that rapidly begin to proliferate (Permitsky and Anderson, 1996. Exp. Cell Res. 22:214–222; Moor et al., 2000. J. Microsc. Res. Tech), and mdx muscle is more effective than normal in myogenic repair (Zacharias and Anderson. 1991. J. Neurol. Sci. 104:190–194; McIntosh et al. 1994. Muscle Nerve 17:444–453, McIntosh and Anderson, 1995. Biochem. Cell Biol. 73:181–190; Permitsky et al., 1996. Biochem. Cell Biol. 74:315–324). Normal quiescence of mdx satellite cells should be restored along with subsarcolemmal NOS-I after mini-dystrophin gene transfer (Decrouy et al., 1998. Gene Therapy. 5:59–64). The general inhibition of the delayed activation seen in injured and intact mdx muscles after L-NAME suggests that activation could still be modulated pharmacologically via NO, possibly in combination with deflazacort (glucocorticoid) treatment to improve repair (Anderson et al., 1996. Muscle Nerve. 19:1576–1585; Anderson et al., 2000. Cell Transplantation (in press)). Other studies on longer term L-NAME exposure of regenerating mdx and normal muscle in vivo showed a high prevalence of branched myotubes, emphasizing the distinct role of NO in fusion (Lee et al., 1994. J. Biol. Chem. 269:14371–14374) separate from activation. Indeed deflazacort may itself affect activation, since another glucocorticoid, dexamethasone, is a specific inhibitor of inducible NOS-II (McCall et al., 1991. Eur. J. Immunol. 21:2523–2527). Experiments on single fiber cultures in vitro indicate that L-arginine can further augment mdx muscle satellite cell activation in vivo (see Example 10). Other data demonstrated that regenerating muscle in NOS-I knockout mice (n=2) had extensive myotube formation over 6 days following injury, similar to mdx mice (e.g. McIntosh et al., (1994). Muscle Nerve 17, 444–453; McIntosh and Anderson, (1995). Cell Biol. 73, 181–190). Interestingly, NOS-I knockout mice also had a modest focal myopathy (segmental muscle fiber damage and inflammation) in TA and diaphragm. That myopathy was not present in the control strain (B6, 129SF), and may relate to the absence of NOS-I expression in the nervous system or a constitutive heightening of satellite cell activation. Together, the mdx and NOS-I knockout experiments suggest that increased satellite cell activation from reduced or absent NOS expression may benefit myogenesis in the short term (and through a few cycles) by facilitating standing activation and precursor recruitment to cycle. However, in the longer term, that standby activation appears to be detrimental. Accordingly, dystrophy may be reduced by either increasing the local (not systemic) pulsatile NO release in intact mdx muscle fibers and/or increasing the bolus of NO that activates satellite cells after fiber injury, which may be achieved by inhibiting NOS activity except after shear-induced release (allowing a larger bolus of NO). And we can now test whether human muscular dystrophy is more severe than mdx dystrophy due to even greater attenuation of the typical NO gradient through the large fibers, over-recruitment of satellite cells and accelerated precursor senescence.

EXAMPLE 10

Isolated Fiber Studies of Satellite Cell Activation on Regenerating Muscle

I. Method of Using an isolated Fiber to Study Satellite Cell Activation

Single intact fibers can be used to examine the dynamic time course of gene expression by satellite cells on fibers in culture (e.g. Bischoff, (1986a) Dev. Biol. 115:140–147; Yablonka-Reuveni, Z, and Rivera, (1994) Dev. Biol. 164: 588–603; Yablonka-Reuveni, Z, Seger R. and Rivera A J. (1999). Cytochem. 47:23–42). Fiber preparations are used to model aspects of development (Cornelison DD, and Wold BJ. (1997). Dev. Biol. 19:270–283) and recruitment-repair sequences, through study of gene transcripts or labelled products that mark recruitment to cycle (PCNA), activity (MAPK), and myogenic specification (muscle regulatory genes, MRFs, c-met). To date, the best and absolute marker of prior satellite cell activation is DNA synthesis, that begins 18–24 hr after an inducing signal or injury on single fibers (Bischoff, 1986. Dev. Biol. 115: 140–147; 1986. Dev. Biol. 111:129–139; Yablonka-Reuveni, Z, Seger R, and Rivera A J. (1999). J. Histochem. Cytochem. 47:23–42). Isolated fibers retain the external lamina as we recently confirmed by E M (Anderson, unpublished observations). However, various reports used intact (Yablonka-Reuveni and Rivera AJ. 1994. Dev. Biol. 164:588–603; Bischoff R. (1990a). J. Cell Biol. 111:201–207) or damaged and hypercontracted fibers (Cornelison DD, and Wold BJ. (1997). Dev. Biol. 19:270–283), so complete characterization of the "intact" fiber model is needed prior to examining activation.

Proliferation of satellite cells, marked by DNA synthesis using tritiated thymidine, is visible after 24 hours (Grounds, M. D., McGeachie, J. K. (1987). Cell Tissue Res. 250: 141–148). Several factors involved in the specification and commitment of satellite cells are known, including members of the myogenic regulatory factor (MRF) family: MyoD, myf5, myogenin, and MRF4 (Biben, C. (1993). Bull. Inst. Pasteur. 91: 161–171; Cornelison, D. D. W., and Wold, B. J. (1997). Dev. Biol. 191:270–283). The mRNAs of c-Fos and c-Jun have been detected as early as 3 hours after injury (Kami, K., Noguchi, K., Senba, E. (1995). Cell Tissue Res. 280:11–19). As well, hepatocyte growth factor/scatter factor (HGF/SF), when colocalized with its receptor, c-met, marks activated cells in vivo. HGF/SF was previously shown to activate quiescent satellite cells in vitro (Allen, R. E., Sheehan, S. M., Tayler, R. G., Kendall, T. L., Rice, G. M. (1995). J. Cell. Phys. 165:307–312).

Preliminary results show that structural damage after crush injury is not apparent for 10 minutes, but satellite cells in vivo change structure and adhesiveness within 1 minute after injury. A method is herein described for using isolated muscle fibers to determine the mechanism of satellite cell activation within the first 30 minutes after injury. Cultured intact muscle fibers have been used to track the time course of MRF expression (Yablonka-Reuveni, Z., Rivera, A. (1994). Dev. Biol. 164:588–603) and proliferation by satellite cells (Bischoff, R. (1986). Dev. Biol. 115:129–139). This technique allows for the tracking of individual satellite cells, as well as populations of cells, under closely monitored conditions away from fibroblasts and inflammatory cells—each sources of cytokines and growth factors also affecting repair. To properly use the isolated fiber to characterize satellite cell activation, we must 1) positively distinguish satellite cells from myonuclei and 2) determine the exact time of fiber death under known conditions. Once these are determined, experiments can be devised to monitor the action of satellite cells immediately after their activation.

1. Isolation of Individual Intact Muscle Fibers (Yablonka-Reuveni, Z., Rivera, A. (1994). Dev. Biol. 164:588–603)

Flexor digitorum brevis (FDB) muscles from normal C57 mice were dissected from the foot, and connective tissue, vessels and nerves were cleaned off the muscle. Following a 3 hr collagenase digestion (0.2% in DMEM), and viewed on a dissecting microscope, the muscle was separated into three bundles and the overlying connective tissue was peeled off the bundles using sharp forceps. The individual fibers were then teased off the remnant tendon and into smaller bundles. Bundles were gently triturated to separate single fibers using a wide mouth glass pipette with a polished end. The fibers were plated onto vitrogen-coated 35 mm dishes and grown in 1.5 ml of DMEM+10% Horse Serum (HS) +1% antimyotics+0.1% gentamycin.

2. Identifying Satellite Cells on Intact Muscle Fibers

To positively identify satellite cells on the fibers, an antibody against c-met, the receptor for hepatocyte growth factor, was used (Cornelison, D. D. W., and Wold, B. J. (1997). Dev. Biol. 191: 270–283). Freshly plated fibers were fixed in ice cold methanol for 10 minutes and rinsed at least 24 hours in Tris Buffered Saline+1% Horse Serum (TBS-HS) at 40C. Plates were then rinsed 3 times with TBS-Tween 20 (0.05%) at room temperature and incubated in c-met primary antibody (1:75 dilution in TBS-HS, Santa Cruz) at room temperature for 1 hour, then overnight at 4° C. Negative controls lacked the primary antibody. The plates were then rinsed 3 times with TBS-Tween 20 and incubated with secondary anti-rabbit FITC (1:200 dilution in TBS-HS) for 2 hours at room temperature. Bis-benzimide (Hoescht 33258), a vital stain for nuclei, was then added for 30 seconds and the plates were then rinsed 5 times and mounted with aqueous mounting medium.

3. Identifying Time of Cell Death Using Marcaine and Ethidium Bromide Staining

Marcaine, an anaesthetic, was previously used to kill live fibers by adding it to a dish for 20–30 minutes (Cornelison, D. D. W., and Wold, B. J. (1997). Dev. Biol. 191:270–283) but the exact time of fiber death was never identified. Ethidium bromide (EtBr) is a fluorescent chemical which intercalates into the DNA of dead cells but is not taken up into live fibers. Media was mostly decanted from freshly plated fibers and the fibers were located using a microscope. 2–3 drops of either EtBr (2.5 µg/ml) in DMEM or Marcaine (0.05%)+EtBr (2.5 µg/ml) in DMEM were then added to the dish under continuous observation. Fiber hypercontraction was observed using a phase lens and the time course of EtBr nuclear staining was observed under UV light using a red filter. Photographs (ASA400 Fuji Colour Film) were taken to record staining of live, fixed, EtBr and Marcaine treated fibers and nuclei.

Summary of Results for EtBr/Marcaine Staining:

1. Addition of EtBr in DMEM to Fiber Cultures

Ethidium bromide stained the nuclei of both fixed fibers and hypercontracted fibers, but did not stain the nuclei of live fibers. Here the fixed fibers with immediate staining of myonuclei, act as the positive control, as do fibers that hypercontracted during a rough preparation, while live fibers immediately after isolation do not have EtBr-fluorescent myonuclei (even after 30 minutes incubation).

2. Addition of EtBr+Marcaine in DMEM

Marcaine had an immediate affect on the fibers and hypercontraction occurred within 5–10 minutes. The nuclei of "live" fibers stained within 60–90 seconds after Marcaine, even if the fiber had not hypercontracted. Therefore Marcaine must allow EtBr to permeate into the cell, though membrane damage must be selective or only gradually allow overt hypercontraction. However, there was no way to differentiate satellite cells from myonuclei using only this method.

Based on the preceding description and results, the following conclusions are reached.
1. Cultures of muscle fibers without connective tissue were obtained from flexor digitorum brevis. Approximately 10–15% of the fibers were damaged during isolation, such that fibers were hypercontracted by 12 hr after plating.
2. Satellite cells were identified on intact fibers and were distinguished from myonuclei using c-met antibody. Appearance by phase contrast was not always reliable in separating satellite cells from myonuclei.
3. Addition of EtBr stains nuclei in hypercontracted fibers immediately, but nuclei in live fibers do not stain at all, even after a 30 minute incubation with EtBr. However, when Marcaine is added in addition to the EtBr, the "live" fiber nuclei stain within the first 60–90 seconds, regardless of whether or not the fiber had hypercontracted. This suggests that Marcaine has a rapid effect on the fiber membrane and allows EtBr to permeate into the fiber, even though hypercontraction may not occur for up to 5 minutes.
4. Since the use of EtBr and phase contrast cannot distinguish satellite cells from myonuclei on live fiber preparations, the use of live/dead staining (Rotman, B., Papermaster, B. W. (1966). Biochemistry. 55:134–141) is required. On fixed fibers, satellite cells can be identified with c-met immunostaining.

Results confirm that fibers were indeed intact and that satellite cells were quiescent. Live fibers exclude Ethidium bromide (EtBr), but 5 minutes after adding a myotoxin called marcaine (Bischoff R. (1990b). Development 109: 943–952) to the medium, nuclei in fibers (and not in satellite cells) are fluorescent for EtBr. Hypercontraction occurs another 5–10 min later. Satellite cells exclude EtBr but take up an indicator of live cells, fluoresceine diacetate (FDA). Without this characterization, observations on satellite cells in a culture could include artefacts from membrane damage that initiates activation differently than any treatment under study. Satellite cells on our intact fibers were also quiescent after isolation. On fibers cultured for 48 hrs (>2 cell cycles after isolation, (Bischoff (1986a). Dev. Biol. 115:140–147) in controlled serum replacement medium (CSR, Sigma), very few satellite cell nuclei had incorporated bromodeoxyuridine (BrdU), a label of new DNA synthesis (only 0.2–0.4±0.04 per live fiber, n=4 experiments, each with >200 fibers). By comparison, satellite cells are significantly activated by crushed muscle extract (CME, Bischoff (1986). Dev. Biol. 115:140–147; 0.8–1.2±0.1BrdU+satellite cells per fiber) Therefore, fiber preparations are intact and most important, have quiescent satellite cells on them. This conclusion is critical to any studies that propose to examine activation signals and their regulation.

II. L-Arginine Treatment of Single Normal Muscle Fibers Increases Satellite Cell Proliferation and Mobility Experiments on activation (marked by DNA synthesis) using single fibers indicate that addition of the NO donor L-arginine stimulates activation in a dose-dependent manner, and also stimulates satellite cell migration away from fibers (FIG. 13). These effects appear to be counteracted by inhibiting NOS in culture.

EXAMPLE 11

Satellite Cell Activation and NOS-I$\mu$ Activity

Muscle repair can be manipulated by changes in NO synthase (NOS-I$\mu$) activity and/or expression that affect satellite cell activation and ultimately proliferation. In vivo, the time course and properties of activation in normal, dystrophic, NOS-I (−/−) and double mutant mdx X NOS-I (−/−) muscle are studied. In culture, single isolated fibers are used to see the effect of activation and satellite cell manipulation after NOS activity or NO concentration is manipulated.

In vivo studies of activation: Activation in vivo (cell release and hypertrophy) is monitored after 2 different stimuli to the tibialis anterior muscle. A traumatic injury (crush) is applied, and compared to activation that occurs after more physiologic injury from repeated electrical stimulation to fatigue (mimicking severe exercise). Another group of mdx mice (half pretreated with daily deflazacort for 3 weeks) receives either a traumatic or physiological stimulus. Activation of satellite cells from dystrophic muscle with and without deflazacort therapy are used to test whether the drug therapy modulates NOS activity/expression in concert with any effects on activation.

Normal C57BL/6 mice, 6–8 weeks of age are divided into three equal groups to receive electrical stimulus, traumatic stimulus or no injury/activating stimulus. The time course of cell yield (activation) has tissues collected at 0, 5, 10, or 30 min. after stimulus.

Based on early data where deflazacort altered NOS expression, the potential effects of deflazacort on activation and possible changes in NOS activity and/or expression are examined in dystrophic mice. mdx mice (3 wks old) are treated with deflazacort or placebo (for 4 wks, (Anderson J E, McIntosh L M, and Poettcker R. (1996). Muscle Nerve. 19:1576–1585) before activation studies.

To manipulate NOS activity, mice receive one of 4 treatments (by intra peritoneal (ip) injection) 30 min before stimulus: saline, the NOS inhibitor L-NAME (N$\omega$-Nitro-L-arginine methyl ester, 7.5 mg/kg), the NO donor L-Arginine (225 mg/kg), or L-NAME plus L-Arginine. These treatments 30 min before injury, alter NOS activity in tissues, assayed by NOS histochemistry (Beesley J E. (1995). Histochem. J. 27:757–769) or [NO]. Long term L-NAME decreases NOS activity and increases NOS-I$\mu$ expression. Dose may change for electrical stimulus. Mice are treated (ip) and are anesthetised and the right tibialis anterior (TA) muscle is prepared for surgery or electrical stimulus 30 min later. These treatments are coded and surgery is routine. The crush injury enables precise studies of a response like activation or repair since it is rapid and synchronized to all TA fibers. For electrical stimulus, the nerve is exposed and positioned over a silver electrode. Pulses are delivered (120 Hz for 5 min) to produce fused tetanic contractions to fatigue the fast muscle, as reported (Anderson, J. E. et al (1988). J. Muscle Res. Cell Motil. 9:499–515).

Assays: a) cell yield time course: Cells are isolated from muscles in time course experiments, each run in one day (4 mice). Mice are killed immediately (o min.) or at 5, 10, 30 min after injury or electrical (fatigue) stimulus, revealing time-dependent changes in cell yield and satellite cell hypertrophy (assays of activation). The very rapid rise in the cell yield ratio of RTA:LTA at 0 min. (typically within 1 min) is dramatic. Cell yield after brief digestion (after (Allen et al. (1998). Methods Cell Bio. 52:155–162) are determined by Coulter counting of cells per muscle, since treatments differentially affect muscle weight (edema) after injury. Logistically, including preparation, surgery and analyses, only 2–3 experiments per week of this type are possible. The RTA:LTA ratio of cell yield (+SEM) is calculated to find the effects of stimuli or treatment on activation.

b) morphologic changes results of satellite cell activation are assessed using tissues collected from stimulated and unstimulated Tas. Muscle sections are used to identify satellite cells, study NOS activity and expression and examine immediate early gene expression as follows.

i) satellite cells are identified and examined for hypertrophy and position using immunostaining for two c-met receptor, m-cadherin, neural cell adhesion molecule (N-CAM or leu19) and CD34, as markers of muscle satellite precursor cells (Irintchev A, Zeschnigk M. Starzinski-Powitz A, and Wernig A. (1994). Dev. Dynamics 199, 326–337; Belles-Isles M, Roy R, Dansereau G, Goulet M, Roy B, Bouhard JP, Tremblay JP. (1993). Eur. J. Histochem. 37:375–380). In other sections c-met and HGF colocalization are used to assess activation (after (Tatsumi R, Anderson J E, Nevoret C J, Halevy 0, and Allen R E. (1998). Dev. Biol. 194:114–128). Routine fluorescent or peroxidase-conjugated secondary antibodies are used to visualize labelled satellite cells.

ii) NOS activity are determined to assess the effect of treatments that manipulate NOS activity. The enzyme histochemistry method using NADPH-diaphorase staining (Beesley JE. (1995). Histochem. J. 27:757–769) is effective in confirming that L-NAME treatment decreases NOS activity for 40 min (after ip injection) and during 6 days recovery (in drinking water). This method is modified to study homogenized tissue NOS activity.

iii) NOS expression is determined using in situ hybridisation (and Northern blotting) with a riboprobe specific for NOS-I$\mu$ (the muscle isoform of NOS-I), made with custom primers (Kobzik L, Reid M B, Bredt D S, and Stamler J S. (1994). Nature. 372:546–548; Meltzer J C, Sanders V, Grimm P C, Stern E, Rivier C, Lee S, Rennie S L, Gietz RD, Hole A K, Watson P H, Greenberg A H, and Nance D M. (1998). Brain Res. Protocols 2:339–351). Since changes in NOS-I mRNA expression can be at variance with NOS activity or satellite cell activation, all three are assessed in every treatment.

iv) the expression of c-fos, an immediate early gene is determined by in situ hybridisation and Northern blotting. c-fos expression increases within 15 min. of liver injury or neurons (Meltzer J C, Sanders V, Grimm P C, Stern E, Rivier C, Lee S, Rennie S L, Gietz R D, Hole AK, Watson P H, Greenberg A H, and Nance D M. (1998). Brain Res. Protocols 2:339–351). Satellite cell c-fos expression after stimulus may corroborate activation.

v) parameters of dystrophy and repair including centronucleation index (the hallmark of regeneration), inflammation and myotube formation in different muscles are examined as previously reported (e.g. McIntosh LM, Permitsky A N, and Anderson J E. (1994) Muscle Nerve. 17:444–453; McIntosh L M, Baker R E, and Anderson, J E. (1998c) Biochem. Cell Biol. 76:532–541; Anderson J E, Garrett K, McIntosh L M, and Poettcker R. (1996). Muscle Nerve. 19:1576–1585).

Analysis of in vivo experiments: The assessments of cell yield (RTA:LTA time course) and morphology/gene expression (tissue sections) shows the extent satellite cells are activated by injury or physiologic stimuli. Results of NOS manipulation reveals the extent to which satellite cell activation (determined as loss of satellite cell adhesion, hypertrophy, colocalization of c-met/HGF, increased c-fos expression) is mediated by NOS activity at the time of injury in vivo.

In vitro studies of activation: Full or complete satellite cell activation is examined, namely by assaying DNA synthesis for proliferation, using single isolated fiber preparations.

Crushed muscle extract (CME, Bischoff R. (1986a). Dev. Biol. 115:140–147; Bischoff R. (1986b). Dev. Biol. 111: 129–139), marcaine (a myotoxic anesthetic), and HGF (Tatsumi R, Anderson JE, Nevoret CH, Halevy 0, and Allen RE. (1998). Dev. Biol. 194:114–128; Gal-Levi R, Y Leshem, S Aoki, T Nakamura, and Halevy O. (1998). Biochim. Biophys. Acta.1402:39–51) are used as potential activating stimuli. mdx or NOS-IKnockout X mdx double mutant mice are used as models of "inhibited" NOS expression.

Experimental Protocol: Fibers are isolated from flexor digitorum brevis (FDB) muscles on the plantar foot of 3 mice, then digested in collagenase (0.2% for 3 hr) and separated under a stereo microscope into small bundles (Yablonka-Reuveni, Z. and Rivera AJ. (1994). Dev. Biol. 164:588–603). Bundles are separated into single fibers by gentle trituration in Dulbecco's medium (DMEM, Gibco BRL) with a glass pipette, and cleaned of cell debris by gentle settling (by gravity) through columns of DMEM. Single fibers are then plated in small aliquots on Vitrogen 100 (collagen) in 35 mm petri plates and incubated in 1.5 ml of medium (see below) containing one or more treatments to regulate NOS activity and/or expression. Antibody detection of BrdU incorporated into satellite cell DNA during fiber incubation is a sensitive marker of activation, as reported for $^3$H-thymidine incorporation (e.g. Bischoff R. (1986a). Dev. Biol. 115:140–147). In occasional experiments autoradiography (McIntosh M+LM, and Anderson J E. (1995). Biochem. Cell Biol. 73:181–190) are used to enable double or triple immunostaining using fluorochrome-conjugated antibodies on the same fibers.

Fibers are incubated in 20% serum replacement medium (CSR; Yablonka-Reuveni, Z, and Rivera A J. (1994). Dev. Biol. 164:588–603). BrdU in the medium labels DNA synthesis. CSR and very gentle dissection minimize stimulation of satellite cells by serum factors or mechanical trauma, and are essential for studying activation. Therefore, fibers incubated only in CSR are the baseline, while other treatments manipulate NO levels. Incubations in medium+BrdU±activator±treatments allow effects on activation to accumulate to significant levels over 48 hr (after Bischoff R. (1986b). Dev. Biol. 111:129–139). Activation is measured by counting labelled satellite cells per fiber (150–250 fibers/dish). Fibers from 6 FDBs for one experiment yield 12–18 dishes, enough for 2–3 dishes/treatment.

Experiments include dishes incubated with crushed muscle extract (CME at 1 mg/ml) to maximally stimulate activation, since our CME is the same concentration (Biscoff R. (1986a). Dev. Biol. 115:140–147; Bischoff R. (1986b). Dev. Biol. 111:129–139; Tatsumi R, Anderson JE, Nevoret CJ, Halevy 0, and Allen RE. (1998). Dev. Biol. 194: 114–128). To find additional or synergistic effects on activation, CME at half-maximal concentration is used. L-NAME (100–400 nM) will inhibit NOS activity in vitro and is included during dissections to prevent pre-activation. NO levels will be increased by L-Arginine (50–1000 nM). Initial results show maximal activation at 500 nM. Longer in vivo manipulation (1 wk) of NOS or [NO] with L-NAME (12.5 mg/mL) or L-arginine (325 mg/mL) in water are examined for effects of treatment on full activation of satellite cells in vitro.

Different activators (CME, marcaine (to damage fibers) or HGF) are compared, since activation can be transient or low, and may not end in sustained recruitment (DNA synthesis assay) if fibers are intact. This also tests for a reinforcing signal that could follow the NO or HGF signals and produce full activation. Marcaine is present only for 10 min, then fresh medium is applied. Breach of fiber membranes is observable even before fibers hypercontract (5–10 min later) since fluorescent red myonuclei are stained by ethidium bromide (EtBr, 2.5% g/mL) in the medium. A live cell indicator, fluoresceine diacetate (FDA) added just before fixation, is seen only in live satellite cells. These studies determine whether or not hypercontraction-induced shear is important in mediating activation.

To characterize activation in muscles with displaced or no NOS activity, FDB fibers from mdx, NOS-I (−/−) mice (129S-NOSI$^{tm/plh}$homozygotes) their controls (B6–129SF) and mdx/NOS-I (−/−) double mutants are examined. mdx and NOS-I mutants are models of chronic NOS inhibition. NO levels are manipulated (L-Arginine, L-NAME) to restore activation to normal.

Analysis of in vitro studies: Fibers are fixed (methanol 10 min), blocked and immunostained for BrdU, the marker of DNA synthesis (proliferation) using DAB detection for stable, easy counting under a microscope. All non-hypercontracted (live) fibers are counted (<10% hypercontracted fibers is acceptable) and the number of BrdU+satellite cell nuclei per live fiber (mean±SD) from each treatment is plotted. BrdU+ cells are confirmed as satellite cells by staining for c-met (Santa Cruz, 1:75), N-CAM (leu19, Sigma), m-cadherin (Santa Cruz) and the live cell indicator (FDA) in marcaine experiments. Experiments include double fluorescence staining for pairs of myoD, c-fos, c-jun, myogenin, c-met, NOS, PCNA, HGF, and BrdU, and DAPI (to mark nuclei) to study the expression of muscle regulatory and early immediate genes in activated and quiescent satellite cells under different conditions.

EXAMPLE 12

Deflazacort Treatment and NO

In DMD patients, deflazacort improves muscle strength (Markham A, and Bryson HM, (1995). Drug Eval. 50:317–333; Reitter B. (1995). Brain Dev. 17 (suppl): 39–43) and delays loss of ambulation (Angelini C, Pegeraro E, Turella E, Intino M T, Pini A, and Costa C. (1994). Muscle Nerve. 17:386–391) while increasing muscle mitochondria and oxidative metabolism (Khan M A. (1993). J. Neurol. Sci. 120:8–14). Importantly it prevents loss of bone trabeculae in comparison to prednisone (LoCascio V, Ballanti P, Milani S, Bertoldo F, LoCascio C, Zanolin E M, and Bonucci E. (1998). Calcif. Tissue Int. 62:199–204). We studied deflazacort effects on muscular dystrophy and muscle repair in mdx mice, genetically homologous to DMD. Early treatment reduced tissue inflammation and increased fiber size in limb and diaphragm muscles (Anderson J E, McIntosh L M, and Poettcker R. (1996). Muscle Nerve. 19:1576–1585). In regenerating muscles (with repair synchronized by crush injury), the myoblast proliferation and fusion into new fibers were higher after deflazacort. Deflazacort also increased strength and laminin expression, advanced new fiber differentiation (marked by MM CK expression, Bischoff and Heintz, 1994 Dev. Dynamics 201: 41–54) and increased the numbers of c-met+satellite cells in regenerating muscle.

A study of 4 groups (n≈10/group) of mdx dystrophic mice treated with placebo, deflazacort, deflazacort plus L-NAME (a NOS inhibitor), or deflazacort plus L-arginine (a NOS donor). Deflazacort was given by daily injection (ip) and L-NAME and L-arginine were given systemically in the drinking water. (L-NAME given systemically by itself is harmful (data not shown); it makes dystrophy more severe and interfere with muscle repair. Presumably, this results from the combined effects on NOS from all sources such as brain, neurons, muscles of the vascular system etc.).

When a normal peripherally nucleated myofiber degenerates, muscle precursor cells proliferate to varying extents (Grounds Md., McGeachie J K. (1989). Exp. Cell Res 180:429–439) and fuse to form centrally nucleated myotubes. These myotubes grow, or even hypertrophy compared to the original distribution of fiber size in that muscle, and span the injured area, (Anderson J E, Ovalle W K, Bressler B H. (1987). Anat. Rec. 219:243–257; Anderson J E, Bressler B H, Ovalle W K. (1988). J. Muscle Res. Cell Motil. 9:499–515; Ontell M, Feng K C, Klueber K, Dunn R F, Taylor F. (1984). Anat. Rec. 208:159 174) but remain centrally nucleated; thus the central nucleation index (CNI) is a useful measure of accumulated damage and repair. (Karpati G, Carpenter S. (1988). Muscle Nerve. 11:795–803). The CNI is a measurement well known in the art (see Karpati and Carpenter. 1988. Muscle Nerve. 11:795–803 and Anderson et al. 1996. Muscle Nerve. 19:1576–1585).

CNI is the proportion of all fibers in a section or a muscle which show a centrally-located nucleus (often given as a percentage). Since muscular dystrophy causes ongoing damage of muscle fibers, the successful repair of those fibers is marked by centrally-nucleated fibers which accumulate as a proportion of total fibers. Unsuccessful repair can be viewed as a loss of fibers in a section of a whole muscle; this too can produce a change in the ratio of centrally nucleated to total number of fibers (expressed as a percentage).

In dystrophy in the mdx mouse, therefore, if central nucleation is high, then dystrophic damage was high; if CNI is lower, then the damage and the requisite subsequent repair are less. There is a theoretical maximum or plateau of CNI (since it is a ratio), which is determined by technical considerations (section thickness). The maximum of CNI is also determined by features of muscle cell biology in repair (e.g. whether a segment viewed in cross section has a central nucleus inside it (which is always a myonucleus, postmitotic) or a peripheral nucleus (which can be a postmitotic myonucleus, as in an uninjured (intact) fiber, or a satellite cell nucleus which can be seen at the periphery of the fiber by light microscopy and is usually considered indistinguishable from the normal myonuclei at the fiber periphery). Even a regenerated segment of a fiber will still have its satellite cell nuclei at the periphery, so classical CNI counts will have to count that segment as peripherally nucleated when a satellite cell is present and no myonuclei are seen (due to the section passing between myonuclei).

In this experiment, muscle tissues are collected from the treated animals. LTA and diaphragm muscles were sectioned, and counts of fibers with central nuclei and fibers with peripheral nuclei were performed. The largest diameter of the muscle section in each of the two sections of each muscle was used for counting, for 10 mice per group (2 muscles per mouse).

FIG. 14 shows that in the mdx mouse, the CNI in placebo-treated animals is about 0.6 (i.e. 60% of fibers) show a centrally located nucleus in a cross section of the muscle. This is similar for the tibialis anterior muscle (LTA) and diaphragm at the age shown in the graph (which is 8 weeks of age) and is reliably used to monitor the progressive effect of dystrophic fiber injury on a muscle over time as the disease progresses. CNI will increase with age in the mdx mice (until the plateau discussed above). Mice are treated from 4–8 weeks of age with placebo, Deflazacort, D+L-NAME or D+L-Arginine.

With deflazacort treatment for 4 weeks, the CNI is significantly less than in placebo-treated mdx LTA (down to 0.4 or 40%) in the left TA (LTA). The CNI in diaphragm (DIA) also decreases with deflazacort treatment (these are the LTAs and DIA muscles from the same animals) This means that deflazacort significantly improves the status of muscles in mdx mice, by sparing them from damage, which therefore reduces the requirement for repair, and reduces CNI as a result. DIA also shows a significantly lower CNI after deflazacort, but the decrease is much less than for LTA deflazacort vs. placebo.

L-NAME treatment (L-N) was then added to deflazacort to see if part of the effect of deflazacort was mediated by NO. The animals were given L-NAME in drinking water, at the same time as they got daily deflazacort injections, both over the 4 week treatment time. In these animals, the LTA CNI was no different than with deflazacort alone, which means the muscles with the less severe dystrophy were not affected by L-NAME treatment in combination with the full beneficial effect of deflazacort to reduce CNI. The DIA CNI was also not affected when deflazacort was given with L-NAME, which suggests that the DIA has more severe dystrophy and combining deflazacort and an inhibitor of NOS activity to depress NOS activity to a lower level than it already is does not increase that severity.

The addition of the NO donor to deflazacort (D+L-Arginine) caused an increase in LTA CNI from deflazacort alone; (though CNI in deflazacort treatment plus L-Arginine is still significantly lower than placebo treatment). However, the NO donor did decrease the CNI of DIA from the level seen with D+L-NAME (i.e. it increased the benefit of deflazacort treatment in the diaphragm). The difference between the D+L-N effect on LTA and DIA suggests that the in situ treatment paradigm for applying NO manipulation in muscle repair is required to optimize its effects, and also that it could be used to augment the effects of steroids like deflazacort. This demonstrates that manipulating NO-mediated activation by changing NOS activity can be most useful when applied in situ to muscles in vivo, since systemic effects can benefit one muscle type (one phenotype of dystrophy) differently (more or less) than in another muscle phenotype.

In summary, deflazacort did significantly reduce the CNI in both the LTA and diaphragm (DIA). The effect was counteracted by L-Arginine in LTA and increased by L-Arginine in DIA, indicating that the systemic effects of L-Arginine (e.g. on the vasculature) augmented the local effects on satellite cell activation. The effedct was counteracted by deflazacort in diaphragm, presumably because the persistent unregulated activation of satellite cells in mdx dystrophic muscle ("standby" mode) is reduced there by L-Arginine. As the mdx diaphragm is the mdx muscle with the most similar phenotype DMD, this result shows that L-Arginine or other No donors can augment the beneficial effects of a steroid such as deflazacort, especially if given locally.

What is claimed is:

1. A method for determining if a change in activation state of muscle precursor cells occurs as a result of a change in a muscle fiber state from the intact state, the method comprising the steps of:
    (a) contacting a DNA intercalator with muscle fibers associated with the precursor cells, and determining whether myonuclear DNA is intercalated; and
    (b) determining a change in activation state of the muscle precursor cells;
    wherein absence of myonuclear DNA intercalation in step (a) indicates that the fiber is intact and that the change in activation state of muscle precursor cells in step (b) occurs as a result of a change in a muscle fiber state from the intact state.

2. The method according to claim 1 wherein the change in activation state is a fiber hypercontraction-dependent change, and wherein step (b) comprises determining a change in activation state when the muscle fiber is contacted with a myotoxin compared to absence of the myotoxin.

3. The method according to claim 1 which is a diagnostic test.

4. A method for identifying a compound which effects a change in activation state of skeletal muscle satellite cells, comprising:
    a) contacting a DNA intercalator with a muscle fiber associated with the muscle satellite cells to determine whether myonuclear DNA is intercalated, wherein absence of myonuclear DNA intercalation indicates that the fiber is intact;
    b) determining the activation state of satellite cells in the absence of the compound; and
    c) determining the activation state of satellite cells treated with the compound;
    wherein the difference between the two activation states identify the compound as a compound which effects a change in activation state of skeletal muscle satellite cells.

5. A method for identifying a compound which effects a fiber hypercontraction-dependent change in activation state of skeletal muscle satellite cells, comprising:
    a) contacting a DNA intercalator with a muscle fiber associated with the muscle satellite cells to determine whether myonuclear DNA is intercalated, wherein absence of myonuclear DNA intercalation indicates that the fiber is intact;
    b) treating an intact fiber containing skeletal muscle satellite cells with a myotoxin and a DNA intercalator to effect fiber hypercontraction;
    c) determining the activation state of skeletal muscle satellite cells in the absence of the myotoxin, DNA intercalator and the compound; and
    a) determining the activation state of skeletal muscle satellite cells treated with the compound in the absence of the myotoxin and DNA intercalator;
    wherein the difference between the two activation states identify the compound as a compound which effects a fiber hypercontraction-dependent change in activation state of skeletal muscle satellite cells.

6. The method according to claim 1 wherein the DNA intercalator is ethidium bromide or propidium iodide.

7. The method according to claim 2 wherein the myotoxin is marcaine.

8. The method according to claim 5 wherein the DNA intercalator is ethidium bromide or propidium iodide.

9. The method according to claim 5 wherein the myotoxin is marcaine.

10. The method according to claim 8 wherein the myotoxin is marcaine.

11. The method according to claim 4 wherein the activation state of satellite cells is determined by determining the level of proliferation of satellite cells.

12. The method according to claim 5 wherein the activation state of satellite cells is determined by determining the level of proliferation of satellite cells.

13. The method according to claim 6 wherein the activation state of satellite cells is determined by determining the level of proliferation of satellite cells.

14. The method according to claim 7 wherein the activation state of satellite cells is determined by determining the level of proliferation of satellite cells.

15. The method according to claim 4 wherein the activation state of satellite cells is determined by monitoring new DNA synthesis in satellite cell nuclei.

16. The method according to claim 5 wherein the activation state of satellite cells is determined by monitoring new DNA synthesis in satellite cell nuclei.

17. The method according to claim 6 wherein the activation state of satellite cells is determined by monitoring new DNA synthesis in satellite cell nuclei.

18. The method according to claim 7 wherein the activation state of satellite cells is determined by monitoring new DNA synthesis in satellite cell nuclei.

19. The method according to claim 15 wherein new DNA synthesis is monitored by determining the incorporation of detectably labeled nucleotide analogues into DNA of satellite cell nuclei.

20. The method according to claim 16 wherein new DNA synthesis is monitored by determining the incorporation of detectably labeled nucleotide analogues into DNA of satellite cell nuclei.

21. The method according to claim 17 wherein new DNA synthesis is monitored by determining the incorporation of detectably labeled nucleotide analogues into DNA of satellite cell nuclei.

22. The method according to claim 18 wherein new DNA synthesis is monitored by determining the incorporation of detectably labeled nucleotide analogues into DNA of satellite cell nuclei.

23. The method according to claim 1 wherein the activation state of the muscle precursor cells is determined by determining the level of proliferation of the muscle precursor cells.

24. The method according to claim 2 wherein the activation state of the muscle precursor cells is determined by determining the level of proliferation of the muscle precursor cells.

25. The method according to claim 1 wherein the activation state of the muscle precursor cells is determined by monitoring new DNA synthesis in muscle precursor cell nuclei.

26. The method according to claim 2 wherein the activation state of the muscle precursor cells is determined by monitoring new DNA synthesis in muscle precursor cell nuclei.

27. The method according to claim 25 wherein new DNA synthesis is monitored by determining the incorporation of detectably labeled nucleotide analogues into DNA of muscle precursor cell nuclei.

28. The method according to claim 26 wherein new DNA synthesis is monitored by determining the incorporation of detectably labeled nucleotide analogues into DNA of muscle precursor cell nuclei.

* * * * *